US010040841B2

(12) United States Patent
Dranitzki Elhalel et al.

(10) Patent No.: US 10,040,841 B2
(45) Date of Patent: Aug. 7, 2018

(54) STABLE FORM OF SIGNAL CONVERTING PROTEIN FUSION PROTEINS, AND METHODS OF USE AND PREPARATION THEREOF

(71) Applicant: KAHR Medical Ltd., Jerusalem (IL)

(72) Inventors: Michal Dranitzki Elhalel, Shoresh (IL); Noam Shani, Zikhron-Yaakov (IL)

(73) Assignee: KAHR Medical Ltd., Jerusalem (IL)

( * ) Notice: Subject to any disclaimer, the term of this patent is extended or adjusted under 35 U.S.C. 154(b) by 0 days.

(21) Appl. No.: 14/655,752

(22) PCT Filed: Dec. 31, 2013

(86) PCT No.: PCT/IL2013/051098
§ 371 (c)(1),
(2) Date: Jun. 26, 2015

(87) PCT Pub. No.: WO2014/106839
PCT Pub. Date: Jul. 10, 2014

(65) Prior Publication Data
US 2015/0376260 A1    Dec. 31, 2015

Related U.S. Application Data

(60) Provisional application No. 61/748,079, filed on Jan. 1, 2013.

(51) Int. Cl.
*C07K 19/00* (2006.01)
*C07K 14/705* (2006.01)

(52) U.S. Cl.
CPC .. *C07K 14/70578* (2013.01); *C07K 14/70521* (2013.01); *C07K 14/70575* (2013.01); *C07K 2319/00* (2013.01)

(58) Field of Classification Search
None
See application file for complete search history.

(56) References Cited

U.S. PATENT DOCUMENTS

| 5,287,386 | A | 2/1994 | Wade et al. |
| 7,142,018 | B2 | 11/2006 | Masleid et al. |
| 7,279,925 | B1 | 10/2007 | Richmond et al. |
| 7,569,663 | B2 * | 8/2009 | Tykocinski ........ A61K 49/0008 |
| | | | 530/350 |
| 2013/0094307 | A1 | 4/2013 | Cheng |

FOREIGN PATENT DOCUMENTS

| WO | WO-2012/042480 | 4/2012 |
| WO | WO 2014/106839 | 7/2014 |

OTHER PUBLICATIONS

Holler et al, "Two Adjacent Trimeric Fas Ligands Are Required for Fas Signaling and Formation of a Death-Inducing Signaling Complex" Molecular and Cellular Biology, Feb. 2003, vol. 23 No. 4, pp. 1428-1440.
Huang et al, "CTLA-4-Fas ligand functions as a trans signal converter protein in bridging antigen-presenting cells and T cells" International Immunology, Jan. 2001, vol. 13 No. 4, pp. 529-539.
Orbach et al, "CD40_FasL and CTLA-4_FasL Fusion Proteins Induce Apoptosis in Malignant Cell Lines by Dual Signaling" The American Journal of Pathology, Dec. 2010, vol. 177 No. 6, pp. 3159-3168.
Herrero-Beaumont Gabriel et al, "Abatacept Mechanism of Action: Concordance With Its Clinical Profile", Reumatologia Clinic. Feb. 15, 2012; vol. 8 No. 2, pp. 78-83.
Arora Swati et al, "Belatacept: A new biological agent for maintenance immunosuppression in kidney transplantation", Expert Opinion on Biological Therapy, May 2012, vol. 12 No. 07, pp. 965-979.
Eisele et al, "APO010, a synthetic hexameric CD95 ligand, induces human glioma cell death in vitro and in vivo" Neuro-Oncology, Feb. 2011, vol. 13 No. 2, pp. 155-164.
Orbach et al, "Anti-Apoptotic Signals Activated T Cells by Interfering with CTLA-4 • FasL Induces Early Apoptosis of", the Journal of Immunology 2007, vol. 179 No. 11, pp. 7237-7294.
Zhang et al, "Intraarticular gene delivery of CTLA4-FasL suppresses experimental arthritis" International Immunology, Feb. 21, 2012, vol. 24 No. 6, pp. 379-388.
Jin et al, "Simultaneous stimulation of Fas-mediated apoptosis and blockade of costimulation prevent autoimmune diabetes in mice induced by multiple low-dose streptozotocin", Gene Therapy, 2004, vol. 11 No. 12, pp. 982-991.
Shi et al, "Prolongation of corneal allograft survival by CTLA4-FasL in a murine model" Graefe's Archive for Clinical and Experimental Ophthalmology, May 31, 2007, vol. 245 No. 11, pp. 1691-1697.
Feng et al, "CTLA4-Fas Ugand Gene Transfer Mediated by Adenovirus Induce Long-Time Survival of Murine Cardiac Allografts", Transplantation Proceedings, Jun. 2005, vol. 37 No. 5, pp. 2379-2381.
Tansey and Szymkowski, "The TNF superfamily in 2009: new pathways, new indications, and new drugs", Drug Discovery Today, 2009, vol. 14 No. 23-24, pp. 1082-1088.
Wyzgol et al, "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand1", the Journal of Immunology, 2009. vol. 183, pp. 1851-1861.
Antoniou et al, "Transgenes encompassing dual-promoter CpG islands from the human TBP and HNRPA2B1 loci are resistant to heterochromatin-mediated silencing", Genomics, 2003, vol. 82 No. 3, pp. 269-279.
Slavin et al, "Spontaneous murine B-cell Leukaemia", Nature, Feb. 1978, vol. 272, pp. 624-626.
Dranitzki Elhalel et al, "CD40_FasL inhibits human T cells: evidence for an auto-inhibitory loop-back mechanism", International Immunology, 2007, vol. 19 No. 4, pp. 355-363.

(Continued)

*Primary Examiner* — Michael Pak

(57) ABSTRACT

A stable fusion protein, wherein in solution, a majority of the fusion proteins are in the homo-hexamer form, which may be prepared for example as a CTLA4-FasL fusion protein.

10 Claims, 49 Drawing Sheets

(56) References Cited

OTHER PUBLICATIONS

Communication Pursuant to Article 94(3) EPC dated Jun. 1, 2017 From the European Patent Office Re. Application No. 13827047.5. (4 Pages).
Communication Pursuant to Article 94(3) EPC dated Sep. 26, 2016 From the European Patent Office Re. Application No. 13827047.5. (3 Pages).
Examination Report dated Jul. 11, 2017 From the Australian Government, IP Australia Re. Application No. 2013371826.(4 Pages).
International Preliminary Report on Patentability dated Jul. 16, 2015 From the International Bureau of WIPO Re. Application No. PCT/IL2013/051098. (14 Pages).
International Search Report and the Written Opinion dated May 15, 2014 From the International Searching Authority Re. Application No. PCT/IL2013/051098. (19 Pages).
Notification of Office Action and Search Report dated Dec. 15, 2017 From the State Intellectual Property Office of the People's Republic of China Re. Application No. 201380074192.4. (7 Pages).
Nalamalpu et al. "Booster for Driving Long Onchip Interconnects—Design Issues, Interconnect Synthesis, and Comparison With Repeaters", IEEE Transactions on Computer-Aided Design of Integrated Circuits and Systems, 21(1): 50-62, Jan. 2002.
Translation of Notification of Office Action and Search Report dated Dec. 15, 2017 From the State Intellectual Property Office of the People's Republic of China Re. Application No. 201380074192.4. (9 Pages).
Communication Pursuant to Article 94(3) EPC dated Feb. 6, 2018 From the European Patent Office Re. Application No. 13827047.5. (5 Pages).

\* cited by examiner

Figure 1A (SEQ ID NO:2)

MRALLARLLLCVLVVSDSKGAMHVAQPAVVLASSRGIASFVCEYASPGKATEVRVTVLRQADSQVTEVCAATYMMGNELTFLDDSICTGTSSGNQVNLTIQGLRAMDT
GLYICKVELMYPPPYYLGIGNGTQIYVIDPEPCPDSGSLEKQIGHPSPPPEKKELRKVAHLTGKSNSRSMPLEWEDTYGIVLLSGVKYKKGGLVINETGLYFVYSKVYFRGQS
CNNLPLSHKVYMRNSKYPQDLVMMEGKMMSYCTTGQMWARSSYLGAVFNLTSADHLYVNVSELSLVNFEESQTFFGLYKL

| CELL-LINE TYPE | CELL-LINE | KILLING EFFECT | ~ EC50 | INCUBATION TIME |
|---|---|---|---|---|
| HUMAN LIVER CANCER | Hep-G2 | POSITIVE | 1.0 nM | 24 HOURS |
| | SK-Hep1 | POSITIVE | 1.5 nM | 24 HOURS |
| | Huh-7 | NEGATIVE | >>120 nM | 48 HOURS |
| HUMAN LIVER CELLS (NON-MALIGNANT) | FH-B | NEGATIVE | 100 nM | 24 HOURS |
| HUMAN KIDNEY CANCER | A498 | POSITIVE | 1.0 nM | 24 HOURS |
| | Caki-1 | POSITIVE | 2.0 nM | 24 HOURS |
| | 786-O | POSITIVE | 1.0 nM | 24 HOURS |
| HUMAN KIDNEY CELLS (NON-MALIGNANT) | PCS-400-010 | NEGATIVE | 100 nM | 24 HOURS |
| | PCS-400-01Y | NEGATIVE | 100 nM | 24 HOURS |
| HUMAN LYMPHOMA (B CELLS) | Raji | POSITIVE | 0.02 nM | 24 HOURS |
| | JY | POSITIVE | 0.04 nM | 24 HOURS |
| HUMAN MULTIPLE MYELOMA | RPMI 8226 | NEGATIVE | >120 nM | 24 HOURS |
| HUMAN PROMYELOCYTIC LEUKEMIA | HL-60 | NEGATIVE | >>120 nM | 24 HOURS |

Figure 5

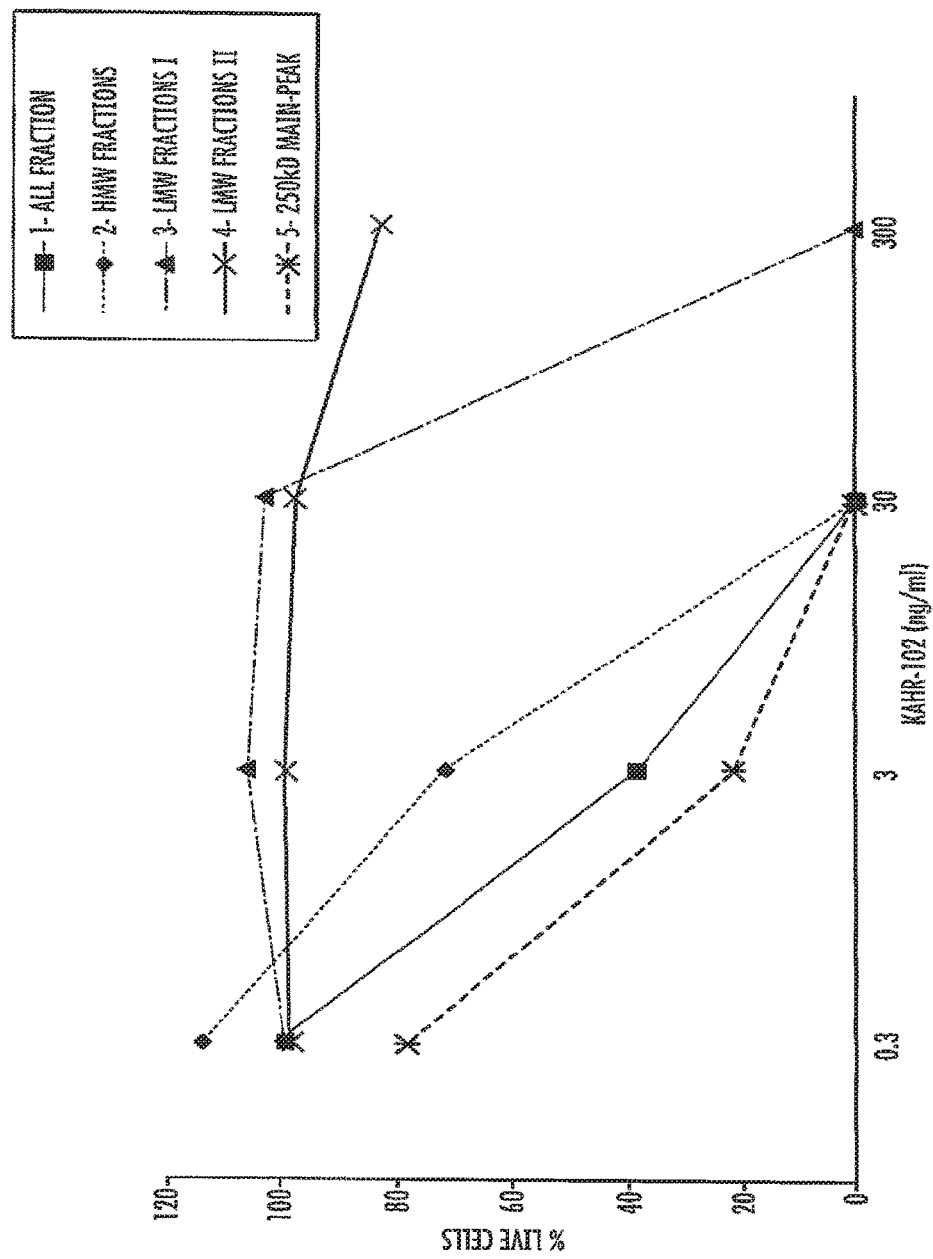

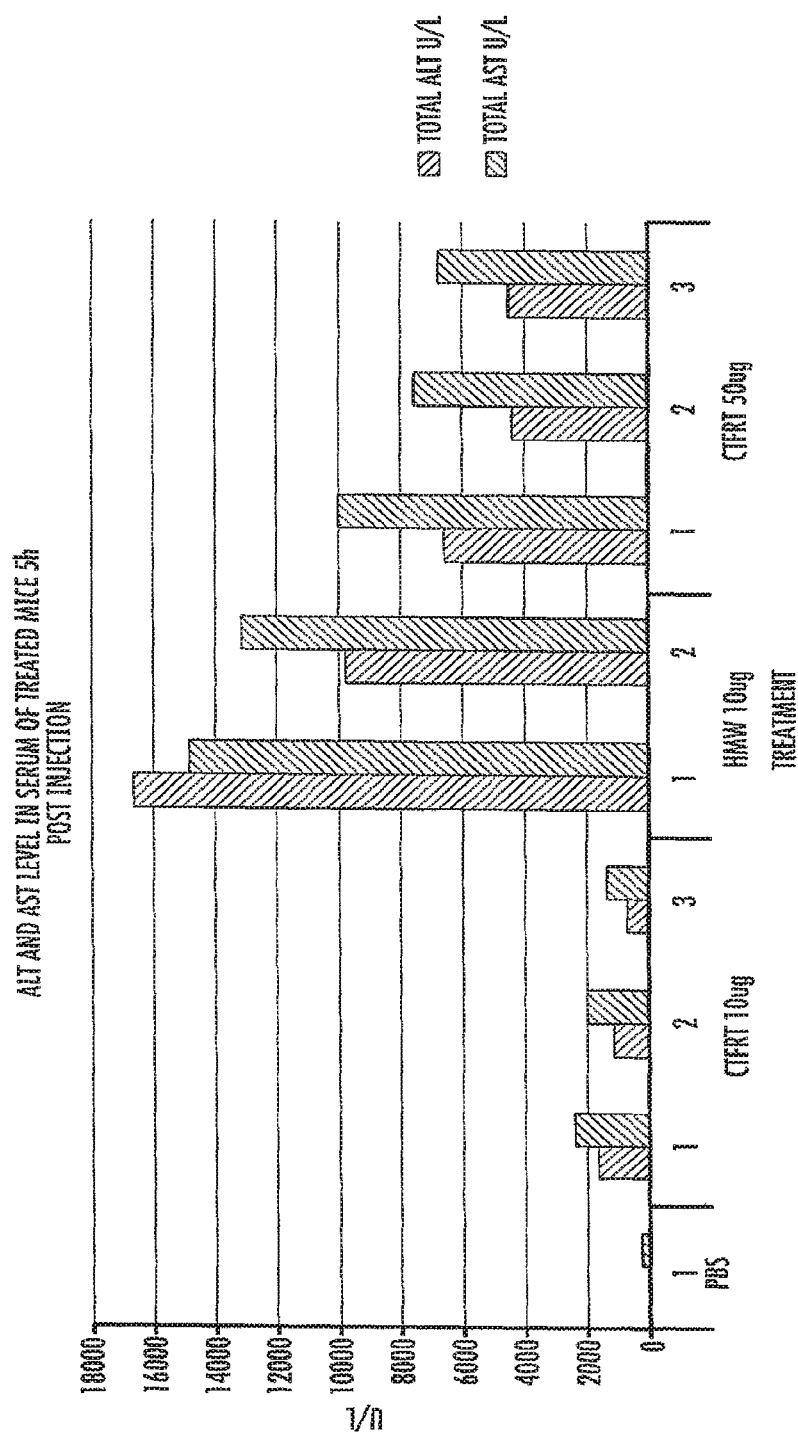

STABLE FORM OF SIGNAL CONVERTING PROTEIN FUSION PROTEINS, AND METHODS OF USE AND PREPARATION THEREOF

FIELD OF THE INVENTION

The present invention, in at least some embodiments, relates to a stabilized form of a SCP (Signal Converting Protein) fusion protein, and in particular, to a homohexamer form of such a fusion protein.

BACKGROUND OF THE INVENTION

Signal-Converting-Proteins (SCP) which are currently known in the art are bi-functional fusion proteins that link an extracellular portion of a type I membrane protein (extracellular amino-terminus), to an extracellular portion of a type II membrane protein (extracellular carboxyl-terminus), forming a fusion protein with two active sides (see for example U.S. Pat. No. 7,569,663). CTLA4-FasL is a SCP in which the N-terminal side is composed of the extracellular domain of CTLA-4, a Type-I membrane protein that binds with high affinity to B7 receptors, and the C-terminal side is composed of extracellular domain of Fas-ligand (FasL), a Type-II membrane ligand that induces cell apoptosis.

CTLA-4 (Cytotoxic T-Lymphocyte Antigen 4), also known as CD152, is a protein receptor that naturally down-regulates the immune system via inhibition of T-cell activation. T-cell activation requires co-stimulatory binding between the CD28 receptor to the CD80 and CD86 receptors, also called B7-1 and B7-2 respectively, on antigen-presenting cells. CTLA-4 is similar in function to CD28 in that they both bind to B7, however, whereas CD28 transmits a positive T-cell activation stimulatory signal, CTLA-4 binds B7 receptors at higher affinity but does not activate T-cells, thus, competing with CD28 and down-regulating the immune-system. The membrane-bound CTLA-4 is known to function as a homodimer that is interconnected by a disulfide bond.

CTLA4's strong binding affinity to B7 led to the design of protein-based therapeutics, linking the CTLA4 extracellular domain to an antibody Fc domain (CTLA4-Fc),that is already approved for use in autoimmune diseases and transplantation (Herrero-Beaumont G, Martinez Calatrava M J, Castañeda S. Abatacept mechanism of action: concordance with its clinical profile. Rheumatol Clin. 2012 March-April 2012; 8(2):78-83). In these chimeric constructs, both the CTLA4 and the Fc domains form a natural homo-dimer (Arora S, Tangirala B, Osadchuk L, Sureshkumar K K. Belatacept: a new biological agent for maintenance of immunosuppression in kidney transplantation. Expert Opinion on Biological Therapy. 2012; 12(7):965-979).

FasL is a Type-II membrane protein that naturally binds and activates Fas-receptors (FasR), which induce cellular apoptosis, or programmed cell death. FasL and FasR belongs to the tumor necrosis factor (TNF) family and FasL/FasR interactions play an important role in the regulation of the immune system and the progression of cancer. FasL, like other TNF super-family members, functions as a non-covalently bound homo-trimeric protein that signals through trimerization of FasR, which usually leads to apoptosis of the "target" cell. Upon FasL binding and trimerization of FasR, a death-inducing signaling complex (DISC) is formed within the target cell, and subsequently apoptosis is induced. Studies indicate that two adjacent trimeric FasL are required for efficient FasR signaling and the formation of DISC (Holler et-al, Molecular and Cellular Biology, February 2003, p. 1428-1440. Eisele et-al, Neuro-Oncology 13(2): 155-164, 2011).

Non-Hodgkin lymphomas (NHLs), as a disease set, is among the ten most prevalent malignant tumors, accounting for approximately 4% of all malignancies in both men and women. NHLs are of B or T-lymphocytes lineage with most (80-90%) of them being of B-cell origin. Though prognosis and treatment depend on specific type and stage, irradiation and chemotherapy have been proven effective in many NHL patients. New protein-based therapeutics, such as anti-CD20, have been recently added to the treatment toolbox. The overall 5-year survival rate has increased to approximately 50%, but there is still need for new effective treatment for the more aggressive and relapsing forms of the disease.

Activated B-cells are known to express high levels of B7 receptors, also known as CD80 (B7.1) and CD86 (B7.2), which are required for T-cell activation as part of a co-stimulatory signal between the T-cell CD28 receptor and the B7 receptors on antigen-presenting cells including B lymphocytes. Similarly to activated B-cells, B-cell lymphoma cells also express high levels of B7 molecules.

Signal-Converting-Proteins (SCP) are a novel type of bi-functional fusion proteins that are formed by directly linking an extracellular domain of a type I membrane protein (extracellular amino-terminus), to the extracellular domain of a type II membrane protein (extracellular carboxyl-terminus), creating a fusion protein with two active sides. CTLA4-FasL is one such SCP, in which the N-terminal side is the extracellular domain of CTLA-4 and the C-terminal side is composed of the extracellular domain of Fas-ligand (FasL) (J.H. H, M.L. T. CTLA-4-Fas ligand functions as a trans signal converter protein in bridging antigen-presenting cells and T cells. International Immunology. 2001; 13 (4): 529-539). Since CTLA4-FasL has the ability to bind to B7 molecules and to FasR, and in doing so, concurrently, to inhibit co-stimulation and induce apoptosis. CTLA4-FasL has been shown to efficiently induce apoptosis of activated T-cells (Orbach A, Rachmilewitz J, Parnas M, Huang J H, Tykocinski M L, Dranitzki-Elhalel M. CTLA-4. FasL induces early apoptosis of activated T cells by interfering with anti-apoptotic signals. J Immunol. December 2007; 179(11):7287-7294) and to function as a strong immuno-modulator in multiple autoimmune and transplantation animal models (Zhang W, Wang F, Wang B, Zhang J, Yu J Y. Intraarticular gene delivery of CTLA4-FasL suppresses experimental arthritis. Int Immunol. June 2012; 24(6):379-388; Jin Y, Qu A, Wang G M, Hao J, Gao X, Xie S. Simultaneous stimulation of Fas-mediated apoptosis and blockade of costimulation prevent autoimmune diabetes in mice induced by multiple low-dose streptozotocin. Gene Ther. June 2004; 11(12):982-991; Shi W, Chen M, Xie L. Prolongation of corneal allograft survival by CTLA4-FasL in a murine model. Graefes Arch Clin Exp Ophthalmol. November 2007; 245(11):1691-1697; Feng Y G, Jin Y Z, Zhang Q Y, Hao J, Wang G M, Xie S S. CTLA4-Fas ligand gene transfer mediated by adenovirus induce long-time survival of murine cardiac allografts. Transplant Proc. June 2005; 37(5):2379-2381). Recently, the present inventors have shown that CTLA4-FasL can induce robust apoptosis of B cell lymphoma cell lines by activating pro-apoptotic signals in parallel to abrogating anti-apoptotic ones (Orbach A, Rachmilewitz J, Shani N, et al. CD40•FasL and CTLA-4•FasL fusion proteins induce apoptosis in malignant cell lines by dual signaling. Am J Pathol. December 2010; 177(6):3159-3168).

SUMMARY OF THE PRESENT INVENTION

Unexpectedly, the present inventors found that CTLA4-FasL fusion proteins are more stable in solution as homo-hexamers, and that in fact the purification and production process for this fusion protein may optionally be adjusted so that the homo-hexamer form is the majority form of the fusion protein. Furthermore, the increased stability of such fusion proteins may be extended to other SCP (Signal Converting Protein) fusion proteins having properties as described below.

By "CTLA4-FasL fusion protein" it is meant a bi-component protein featuring a CTLA4 domain and a FasL domain as described herein which are linked covalently. This fusion protein is also referred to herein as "CTLA4-FasL". Optionally and preferably, the bi-component protein comprises the extracellular domain of CTLA-4 and the extracellular domain of Fas-ligand (FasL). Optionally and more preferably, the bi-component protein has an N-terminal side which is the extracellular domain of CTLA-4 and a C-terminal side which is composed of the extracellular domain of Fas-ligand (FasL).

Although this form is referred to as a homo-hexamer, it may optionally also be described as a multimer of approximately 250 kD. Without wishing to be limited by a single hypothesis, it is believed that two different types of homo-hexamer structures may optionally form in terms of the interactions, which may be covalent or non-covalent. In a first type, the homo-hexamer forms via interactions of and hence dimerization of two FasL trimers. In a second type, the homo-hexamer forms via interactions of and hence trimerization of three CTLA4 dimers. Of course these different types are presented as non-limiting examples only.

These findings (that CTLA4-FasL fusion proteins are more stable in solution as homo-hexamers) are particularly unexpected because nothing in the characteristics of either component of the fusion protein would have previously lead one of ordinary skill in the art to predict such an outcome. Fusion of a dimeric protein such as CTLA-4 to a trimeric TNF super-family member such as FasL opens up the possibility that oligomers may form. For example, covalently linked homo-dimers can form via the formation of the natural, disulfide-linked, dimer of CTLA-4, while homo-trimers can form via the natural requisite of FasL to trimerize. One article that studied this question by using chemical cross-linking and gel filtration analyses showed that CTLA4-FasL complexes do contain intermolecular disulfide-bridges but indicated a trimeric molecular stoichiometry (Huang and Tykocinski, Int Immuno 2001, vol 13, no 4, pp 529-539). The authors indicated that since the main structures they identified were homo-trimers and the formation of a homo-hexamer in solution is not likely, homo-hexamers might form on the surface of the target cell, inducing the extremely effective apoptosis they have recorded.

According to at least some embodiments of the present invention, there is provided a stable CTLA4-FasL fusion protein, wherein in solution, a majority of the fusion proteins are in the homo-hexamer form.

According to at least some embodiments of the present invention, there is provided a method for producing a stable CTLA4-FasL fusion protein, wherein the protein is characterized in that in solution, a majority of the fusion proteins are in the homo-hexamer form. Optionally and preferably, the homo-hexamer form is present as the majority form after initial harvesting, but before any purification methods have been applied to the protein.

By "initial harvesting" it is meant for example after cell media has been harvested, such that cells are removed from the media (optionally through centrifugation or filtration for example), as the protein is secreted into the cell media from the cells. The initial harvesting process is preferably performed such that the homo-hexamer form is present as the majority form in the cell media. Furthermore, the purification process is optionally performed so as to maintain the homo-hexamer form as the majority form during purification. By "majority form" it is meant that the homo-hexamer form is at least 51% of the fusion proteins. Unless otherwise indicated, percentages of the fusion protein are given with regard to the total fusion protein amount, and not necessarily with regard to the total protein content.

According to at least some embodiments, the homo-hexamer form is optionally at least 51%, preferably at least 60%, more preferably at least 70%, most preferably at least 80%, optionally and most preferably at least 90%, also optionally and most preferably at least 95%, 96% and so forth up to 100% of the total fusion protein; optionally any percentages between these amounts may also be contemplated within these embodiments.

According to at least some embodiments, the homo-hexamer form is optionally the majority form before purification and is preferably the majority form after purification. If the homo-hexamer form is not a majority form, then it is at least a significant minority (preferably at least 20%, more preferably at least 30%, most preferably at least 40% and optionally and most preferably 50%; optionally any percentages between these amounts may also be contemplated within these embodiments).

According to at least some embodiments, a dodecamer form is present, optionally before and/or during and/or after purification. Optionally the dodecamer form is the majority form during purification; optionally and preferably, regardless of whether the dodecamer form is the majority form during purification, the homo-hexamer form is the majority form at least after purification and optionally before purification. Although this form is referred to as a dodecamer, it may optionally also be described as a multimer of approximately 500 kD.

According to at least some embodiments, the dodecamer form is optionally no more than 5% of the total fusion protein. Preferably, the dodecamer form is no more than 4% of the total fusion protein. More preferably the dodecamer form is no more than 3% of the total fusion protein. Most preferably, the dodecamer form is no more than 2% of the total fusion protein. Optionally and most preferably, the dodecamer form is no more than 1% of the total fusion protein.

According to at least some embodiments, the above embodiments, regarding the amounts of the dodecamer and the amounts of the homo-hexamer, are optionally combined.

According to at least some embodiments, there is provided a stable homo-hexamer SCP (Signal Converting Protein) fusion protein in majority form. As used herein, the term "fusion protein" generally refers to a protein in which the N-terminal end forms a homodimer and has a specific biological function, and the C-terminal side forms a homotrimer and has a different biological function. The N-terminal end is referred to as the "component 1 protein" while the C-terminal end is referred to as the "component 2 protein."

According to at least some embodiments of the present invention, the fusion protein is a fusion of a Type-I protein and a Type-II protein, in which the Type-I is known to form a homodimer and the type-II is known to form a homotrimer.

Based on the data presented herein for CTLA4-FasL fusion protein, these fusion proteins should form homo-hexamers and offer improved activity.

The above description regarding purification of the stable homo-hexamer and the definition of majority form also apply to these general fusion proteins. Examples are given below for component 1 and component 2 proteins. It is understood that optionally a functional portion of the protein may be used to form the fusion protein, such as (where applicable) an extracellular portion of the protein.

For the first protein (component 1), non-limiting examples include many receptors or ligands that naturally form homodimers, optionally including disulfide-linked dimers, e.g., BTN3A1, CD27, CD80, CD86, ENG, NLGN4X, CD84, TIGIT, CD40, IL-8, IL-10, CD164, LY6G6F, CD28, CTLA4, TYROBP, ICOS, VEGFA, CSF1, VEGFB, BMP2, BMP3, GDNF, PDGFC, PDGFD, TGFB1, LY96, CD96 and GFER. Of these component 1 proteins, at least CD28, CTLA4, TYROBP, ICOS, VEGFA, CSF1, VEGFB, BMP2, BMP3, GDNF, PDGFC, PDGFD, TGFB1, LY96, CD96 and GFER are expected to form disulfide links to form the homodimers as part of the formation of the homo-hexamer, without wishing to be limited by a single hypothesis.

For the second protein (component 2), some non-limiting examples include all TNF-superfamily ligands, e.g., FasL, TRAIL, TNF-alpha, TNF-beta, OX40L, CD40L, CD27L, CD30L, 4-1BBL, RANKL, TWEAK, APRIL, BAFF, LIGHT, VEGI, GITRL, EDA1/2, Lymphotoxin alpha and Lymphotoxin beta (reference: Tansey and Szymkowski, Drug Discovery Today, 2009 December; 14(23-24)).

Optionally and preferably, the TNF-superfamily ligands for the component 2 protein form a non-covalent homotrimer as part of the formation of the homo-hexamer. Although it is well documented that TNF-superfamily ligands naturally form homotrimers, their most efficient activation receptor-activation structure seems to be as two adjacent trimers or as a homo-hexamer (Eisele et al, AP0010, a synthetic hexameric CD95 ligand, induces human glioma cell death in vitro and in vivo; Neuro-Oncology vol 13(2): pp 155-164, 2011; Wyzgol et al, Trimer Stabilization, Oligomerization, and Antibody-Mediated Cell Surface Immobilization Improve the Activity of Soluble Trimers of CD27L, CD4OL, 41BBL, and Glucocorticoid-Induced TNF Receptor Ligand, J. Immunol. 2009; vol 183; pp 1851-1861; and Holler et al, Two Adjacent Trimeric Fas Ligands Are Required for Fas Signaling and Formation of a Death-Inducing Signaling Complex, Mol. Cell. Biol. 2003, vol 23(4): pp 1428-1440).

According to at least some embodiments of the present invention, the component 1 protein is a type-I protein, while the component 2 protein is a type-II protein. Optionally and preferably for such embodiments, the bi-component protein comprises the extracellular domain of the type-I protein and the extracellular domain of the type-II protein. Optionally and more preferably, the bi-component protein has an N-terminal side which is the extracellular domain of the type-I protein and a C-terminal side which is composed of the extracellular domain of the type-II protein.

Exceptions to the above embodiment involving extracellular proteins may optionally include proteins which do not feature transmembrane domains, yet which may still function as component 1 or component 2 proteins. Non-limiting examples of such proteins for component 1 proteins include VEGFB, BMP2, BMP3, GDNF, PDGFC, PDGFD, TGFB 1, GFER and LY96. Non-limiting examples of such proteins for component 2 proteins include April and TNF-beta. Of course, other exceptions to the above embodiment may also occur and are encompassed within various embodiments of the present invention.

Non-limiting examples of disease indications and potential fusion protein combinations are given below, although of course other/different disease indications and/or fusion protein combinations are possible and are encompassed within various embodiments of the present invention. By "combination" as described herein with regard to fusion protein components, it is meant bi-component fusion proteins comprising a component 1 protein (or functional portion thereof) and a component 2 protein (or functional portion thereof).

1. For immune induction (e.g., for treatment of cancer, although optionally also for treatment of other diseases for which the subject would benefit from immune induction), combine component 1 homodimer candidates that may have immune-targeting or immune-induction activities (e.g., CD28, CSF1, LY96, CD96, BTN3A1, TIGIT, IL8, IL10, CD80, CD86, LY96), with component 2 homotrimer candidates that may induce the immune system and induce growth (e.g., TNF, OX40L, CD40L, CD27L, CD30L, 4-1BBL, TWEAK, APRIL, BAFF, LIGHT, GITRL).

2. For immune suppression and/or cancer cell apoptosis, combine component 1 homodimer candidates that may have immune-targeting or immune-inhibitory activities (e.g., CTLA4, CD40, TYROBP, CD27, ENG), with component 2 homotrimer candidates that may activate apoptosis or suppress growth (e.g., FasL, TRAIL, VEGI).

3. For induction of angiogenesis for treatment of any disease for which the subject would benefit from angiogenesis induction, combine component 1 homodimer candidates that may have angiogenic activities (e.g., VEGFA), with component 2 homotrimer candidates that may activate angiogenesis or activate growth (e.g., TWEAK, APRIL).

4. For inhibition of angiogenesis for treatment of any disease for which the subject would benefit from angiogenesis inhibition, combine component 1 homodimer candidates that may have anti-angiogenic activities (e.g., ENG), with component 2 homotrimer candidates that may suppress angiogenesis or activate apoptosis (e.g., FasL, TRAIL, VEGI).

5. For induction of bone formation, combine component 1 homodimer candidates that may have bone formation activities (e.g., BMP2), with component 2 homotrimer candidates that may activate cell growth and bone formation (e.g., TWEAK, APRIL).

6. For inhibition of bone formation, combine component 1 homodimer candidates that may have inhibitory bone formation activities (e.g., BMP3), with component 2 homotrimer candidates that may activate bone resorption, apoptosis or suppress growth (e.g., RNAKL, FasL, TRAIL, VEGI).

7. For liver regeneration for treatment of any disease for which the subject would benefit from liver regeneration, combine component 1 homodimer candidates that may have liver regeneration activities (e.g., GFER), with component 2 homotrimer candidates that may activate cell growth and (e.g.,TWEAK, APRIL).

BRIEF DESCRIPTION OF THE DRAWINGS

FIG. 1A shows the amino acid sequence of the CTLA4-FasL fusion protein; FIG. 1B shows the vector including the nucleic acid sequence for the fusion protein.

FIG. 2: Western Blot of reduced SDS-PAGE analysis of glycosylated and deglycosylated samples of CTL4-FasL expression in CHO-S cells. The Western blot was probed with anti-human CTLA-4 and developed using the colorimetric detection method. Lane 3 (marked deglycosylated) features the CTL4-FasL fusion protein deglycosylated with Peptide N-Glycosidase F that removes N-glycan chains from the protein.

FIG. 3: SDS-PAGE analysis of purified CTLA4-FasL fusion protein; samples were taken from different stages at the purification (SEC fractions) and compared to previously purified CTLA4-FasL fusion protein. Samples were either reduced (FIG. 3A) or non-reduced (FIG. 3B).

FIG. 4A shows iso-electric focusing at pH 3-10, while FIG. 4B shows iso-electric focusing at pH 3-7.

FIG. 5: Killing activity of purified CTLA4-FasL fusion protein on different malignant and non-malignant human cell-lines.

FIG. 6: Gel-filtration chromatography (Seperose-12 column) analysis of purified CTLA4-FasL fusion protein.

FIG. 7: shows the results of CTL4-FasL fusion protein analysis after SE-HPLC (FIG. 7A) and Native-PAGE (FIG. 7B); the different lanes show three different batches with two different amounts) for purified CTLA4-FasL. FIG. 7A-1 shows the fusion protein results while FIG. 7A-2 shows the results of standard proteins.

FIG. 8A shows SE-HPLC analysis of the production harvest (black line) with a purified fusion protein peak as an overlay (blue line); FIG. 8B shows Gyrolab quantification of the overall production harvest (red line) and CTLA4-FasL fusion protein of the chromatographic fractions of the growth media (green line).

FIG. 9A: SEC-HPLC analysis overlay of SEC chromatography fraction pools representing four different product types; 250 kD (green line), HMW (blue line), LMW1 (red line), and LMW2 (brown line) FIG. 9B. The killing activity of the four SEC fraction pools was quantified by a bioassay that measures killing of human cancer cells in-vitro FIG. 10: SE-HPLC analysis of purified CTLA4-FasL fusion protein following repeated (1×, 3×, 5×) freeze/thaw cycles.

FIG. 11: SE-HPLC analysis of purified CTLA4-FasL fusion protein following reduction with increasing concentration of glutathione (GSH, FIG. 11A) or oxidation with increasing amounts of copper sulphate (CuSO4, FIG. 11B).

FIG. 12: FACS was used to quantify the expression of the three target receptors of CTLA4-FasL, namely CD80 (B7.1), CD86 (B7.2) and CD95 (FasR), on the different human cancer cell lines, legend shown in FIG. 12B. The killing effect (EC50) of the fusion protein on these cell-lines, measured by bioassay, is indicated on the bottom of each graph. The cells tested were as follows: FIG. 12A, RPMI8226 (multiple myeloma); FIG. 12B, HL60 (APL (acute promyelocytic leukemia)); FIG. 12C, JY (B cell lymphoblastic cell line); FIG. 12D, Raji (B cell lymphoma); FIG. 12E, A498 (RCC); and FIG. 12F, SK-Hep1 (HCC (hepatocellular carcinoma)).

FIG. 13: FIGS. 13A-1 and 13A-2 show the effect of the addition of caspase inhibitors to CTLA4-FasL apoptotic activity on various cell lines. FIG. 13B shows that CTLA4-FasL has a robust effect as a fusion protein even in non-B7 expressing cells when compared to either CTLA4OIg sFasL or their combination. FIGS. 13C-13E are Western blots of whole cell lysates that show that CTLA4-FasL at low doses abrogates anti-apoptotic signals and activates the pro-apoptotic signals in B7 expressing cells (Raji cells (B-cell lymphoma)), but not in B7 negative cells A498 cells (renal cancer). At higher doses CTL4-FasL effectively activated pro-apoptotic signals in both cell lines.

Figure 16A:
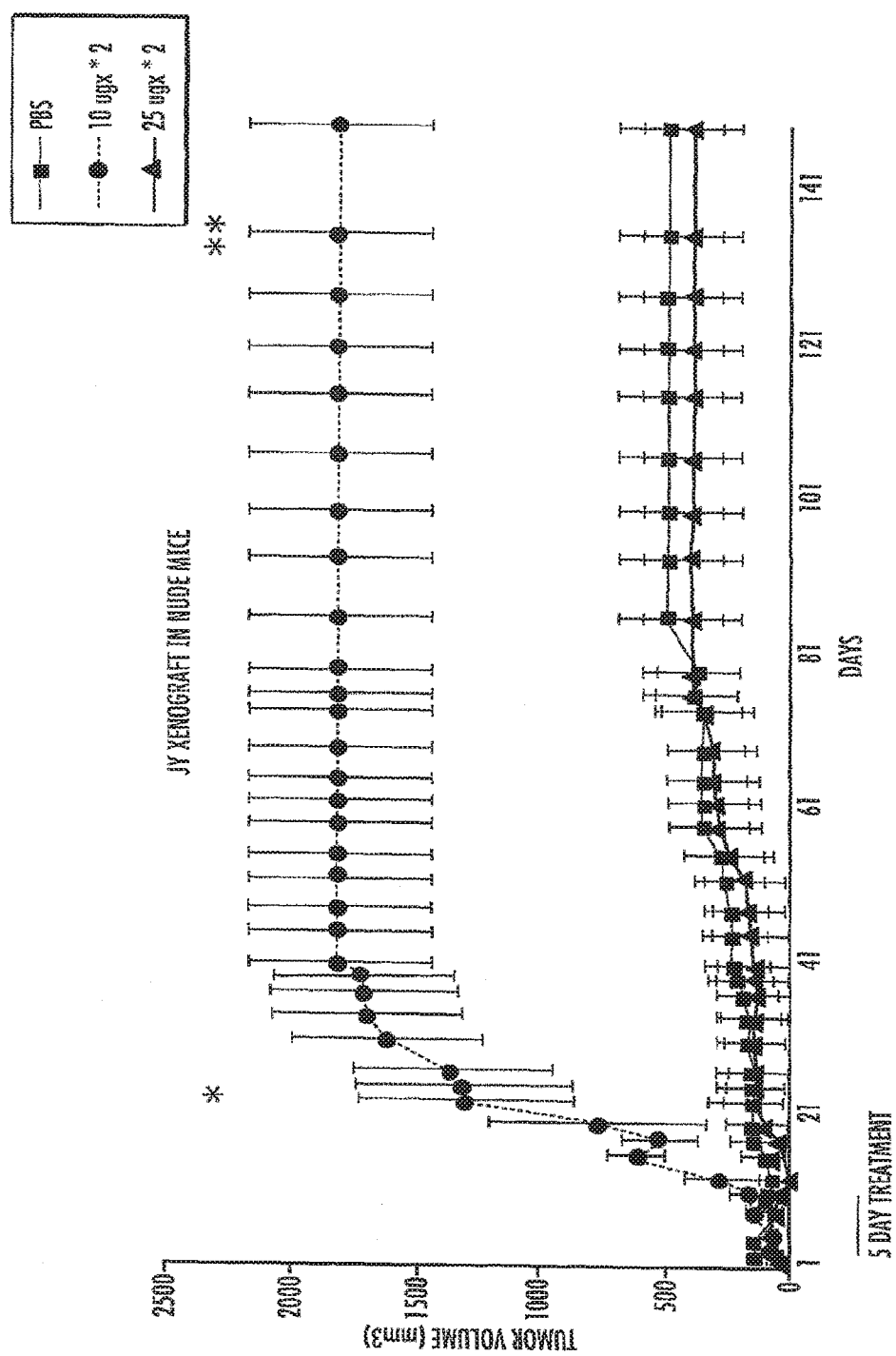
Figure 16B:
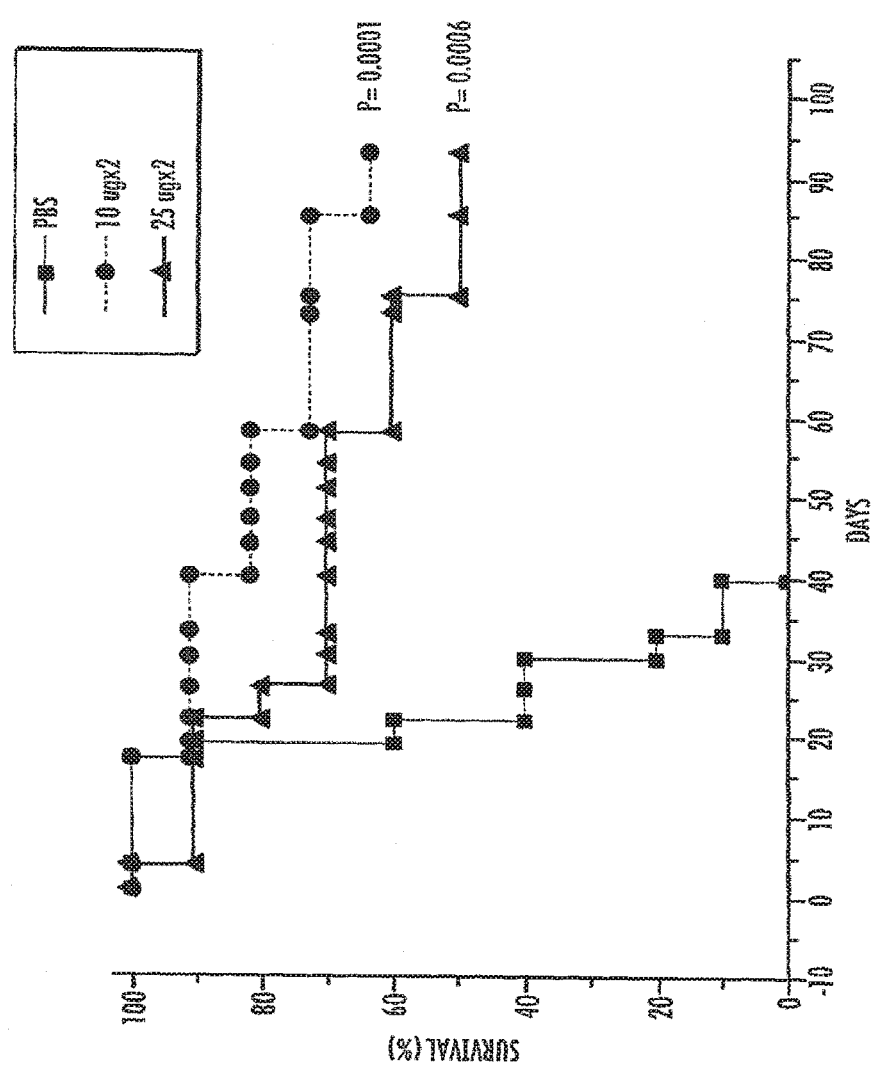

FIG. 16 shows that treatment with both 50 ug and 20 ug daily dosages of CTLA4-FasL for 4 days significantly inhibited the long-term growth of human JY xenograft tumors (FIG. 16A), and significantly improved the survival of the treated mice (FIG. 16B).

Figure 17A:
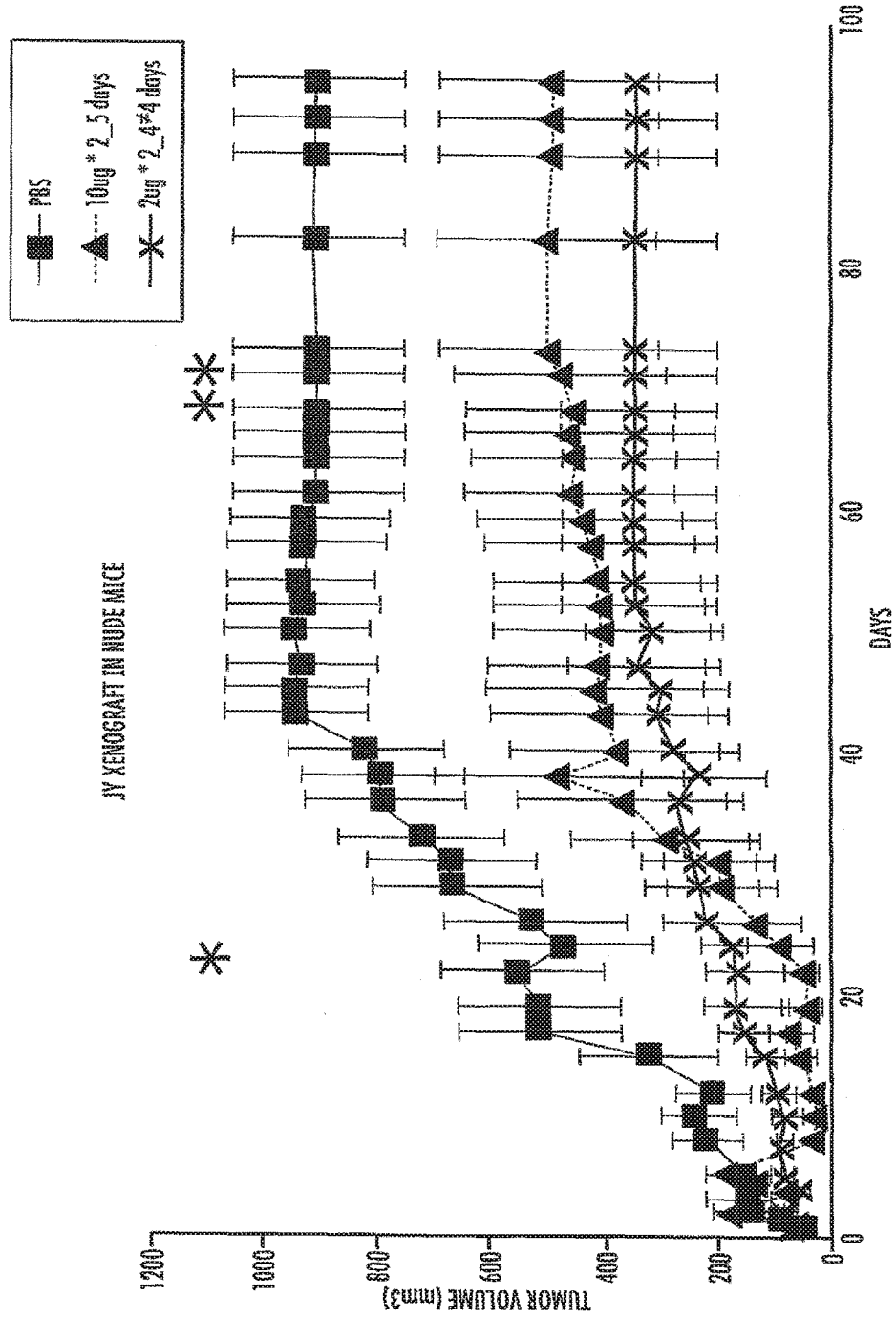
Figure 17B:
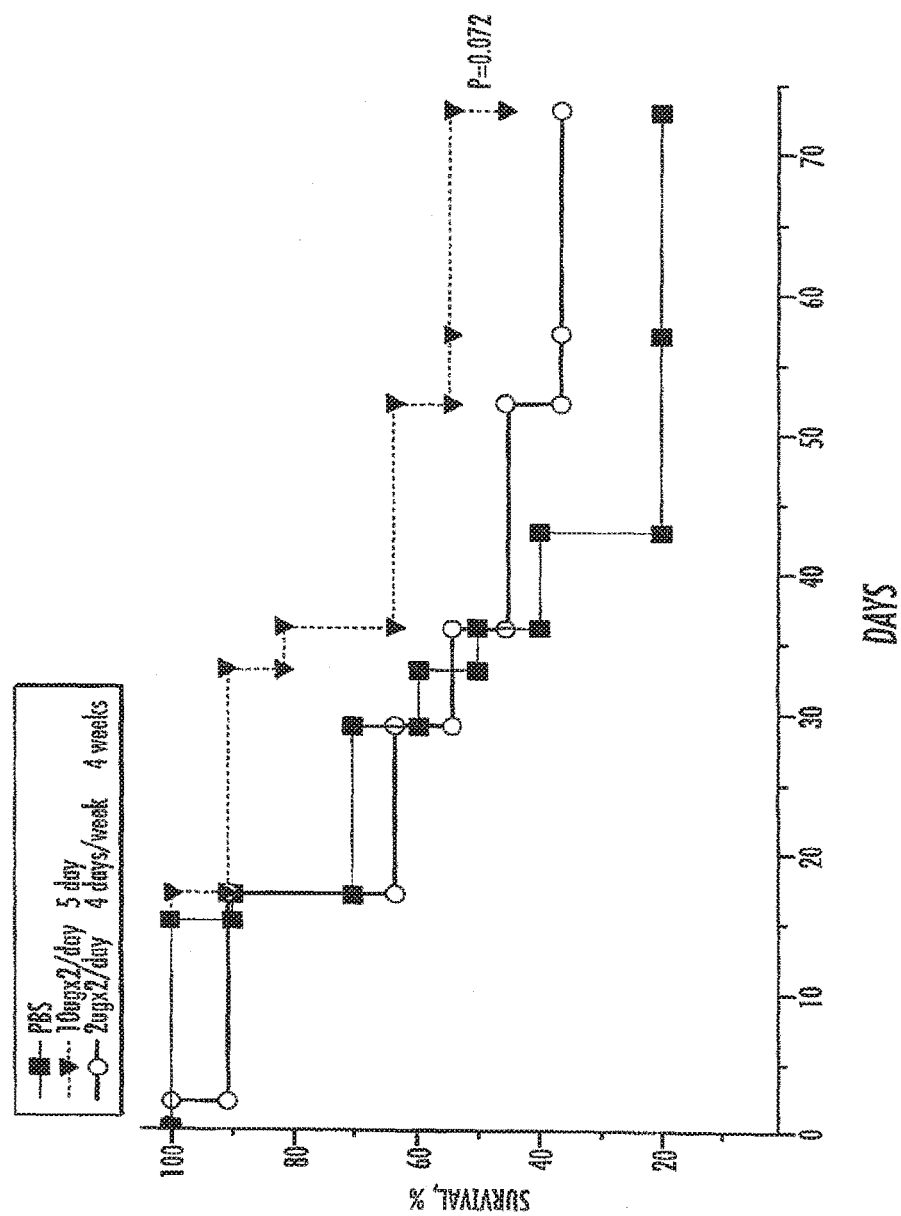

FIGS. 17A and 17B show the effect of lower dosages of CTLA4-FasL for 4 days, which significantly inhibited the long-term growth of human JY xenograft tumors (FIG. 17A), and significantly improved the survival of the treated mice (FIG. 17B).

Figure 18:
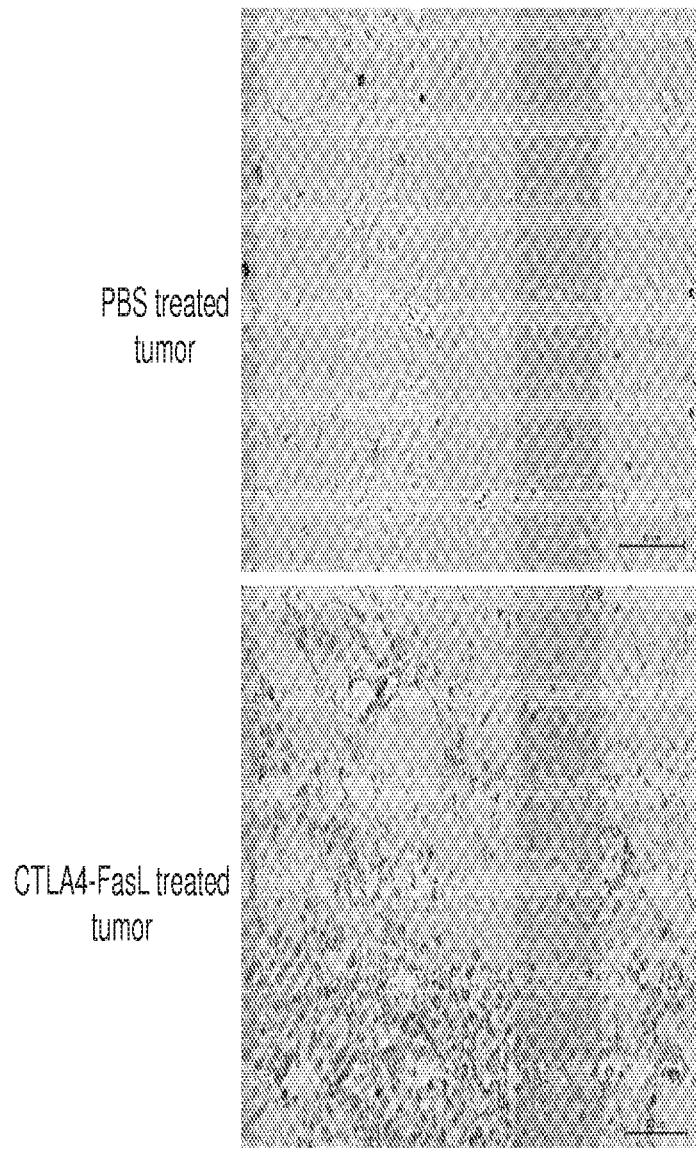
Figure 19:
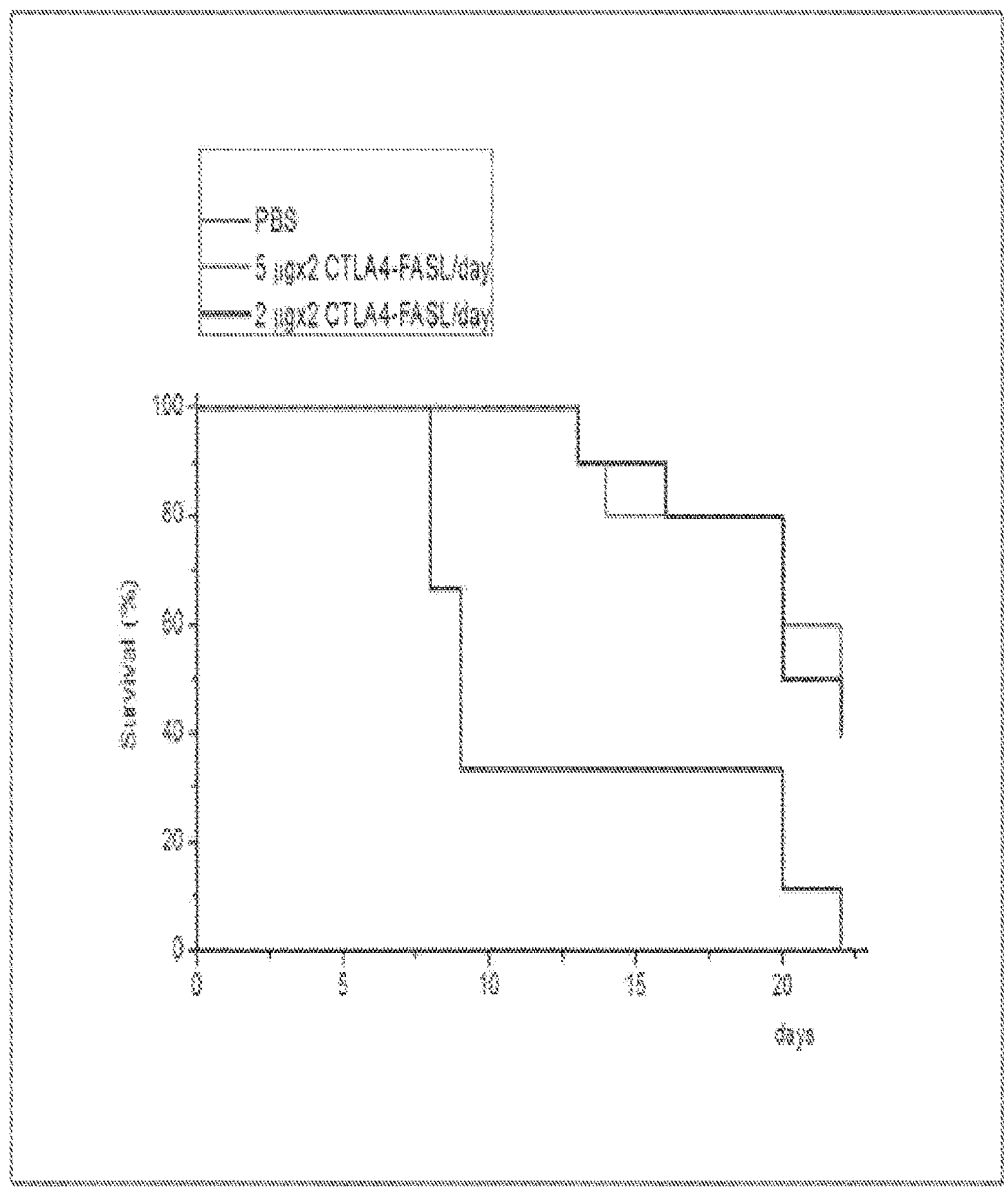
Figure 20:
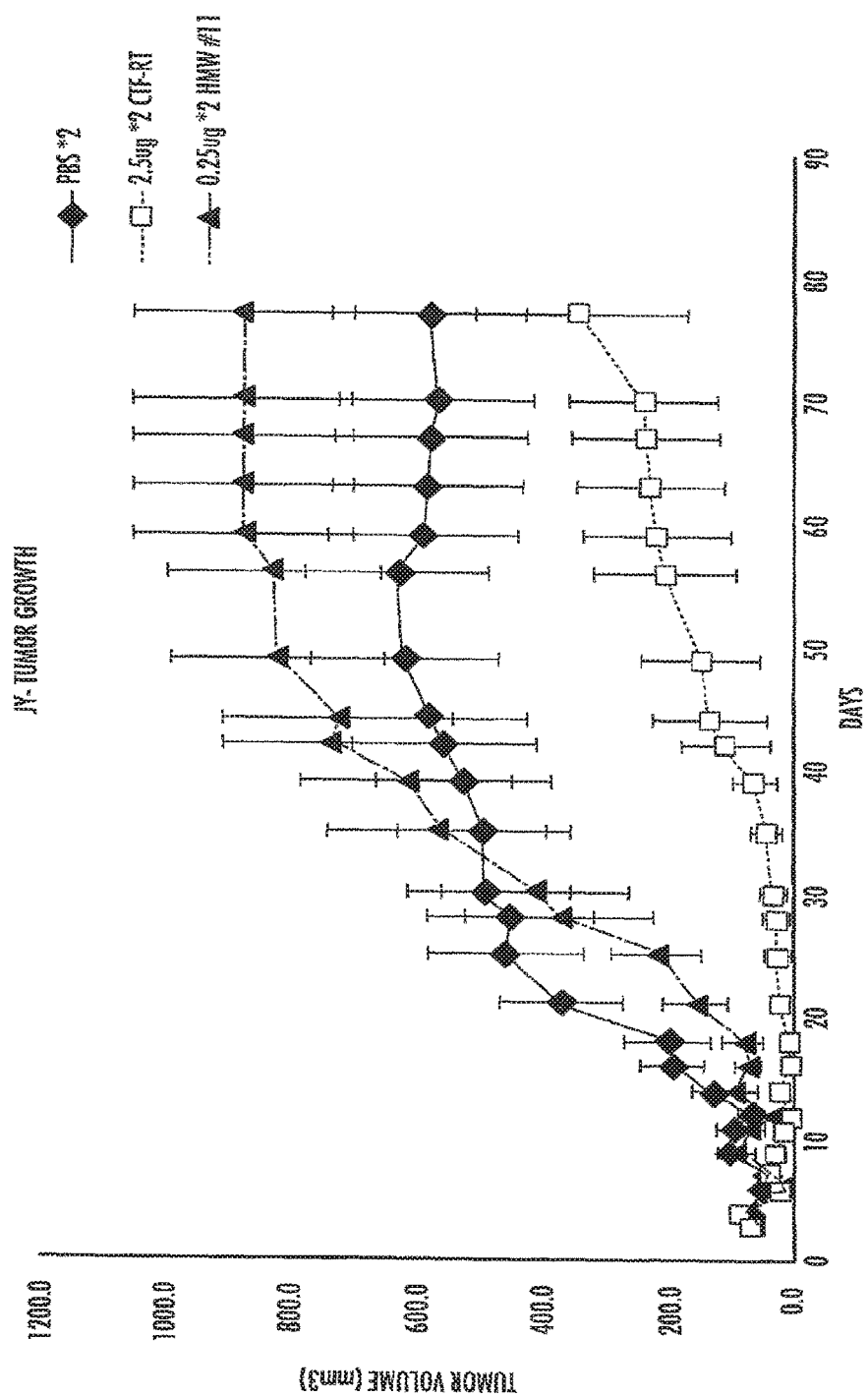
Figure 23:
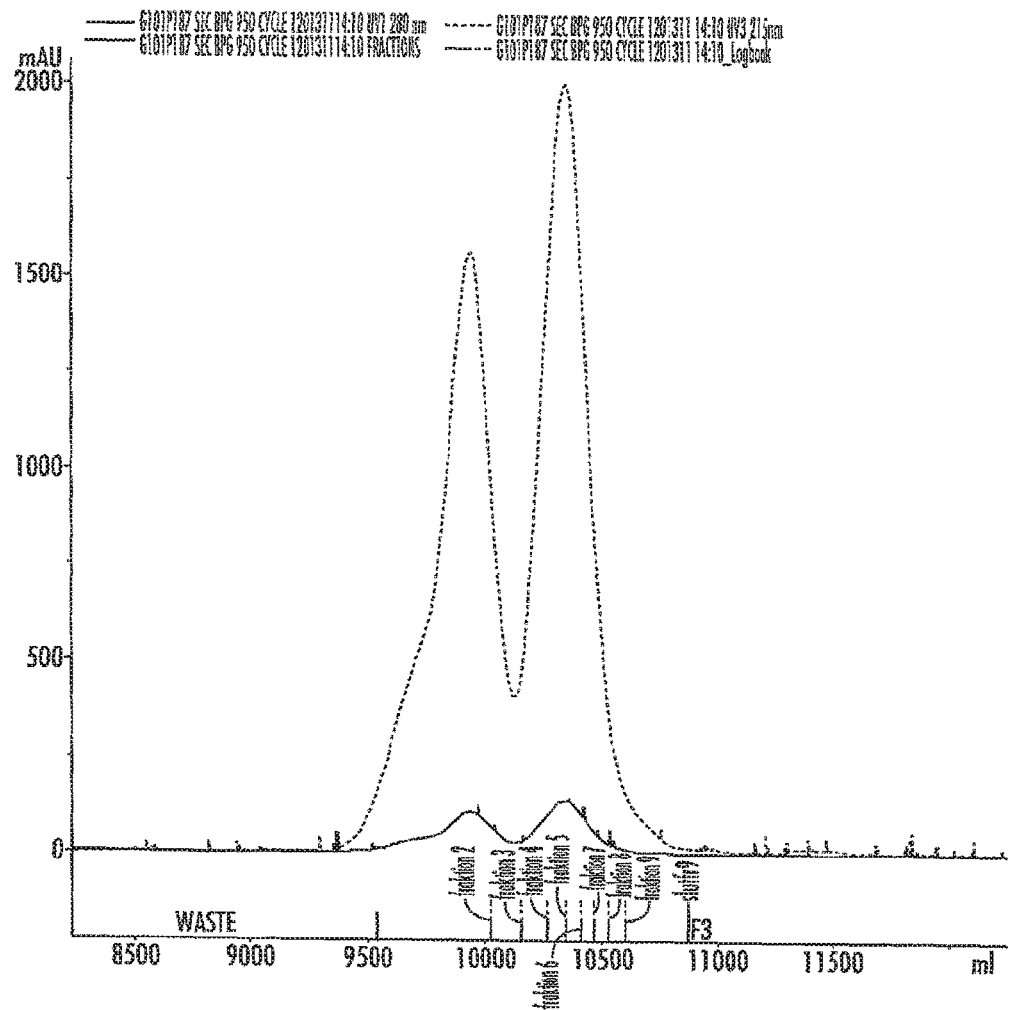
Figure 24:
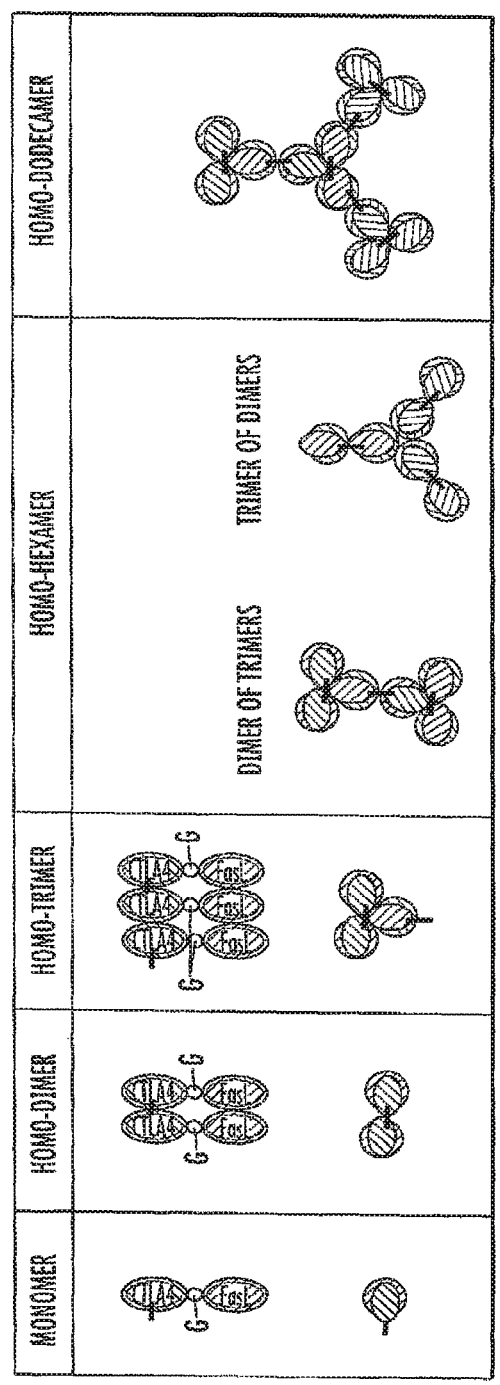

FIG. 18: shows histological analysis of JY tumors removed from the mice; immunostaining with anti-cleaved caspase 3 demonstrated that tumor cells in CTLA4-FasL treated mice (bottom) but not vehicle (PBS) treated mice (top) undergo apoptosis;

FIG. 19 shows the effect of CTLA4-FasL treatment on the survival of normal mice pre-injected with mouse BCL-1 mouse lymphatic cancer cells, showing that two doses per day of 5 ug or 2 ug of the fusion protein significantly increased mouse survival;

FIG. 20 shows the effect of the dodecamer as opposed to the hexamer on tumors in mice in-vivo, in which the HMW #11 fraction is the dodecamer, while the line marked "CTF-RT" is the purified (containing at least 90%) homo-hexamer preparation;

FIG. 21 shows the levels of ALT/AST enzymes in mice serum;

FIG. 22 shows cytokine levels in mice serum;

FIG. 23 shows the increased presence of the dodecamer form of CTLA4-FasL fusion protein during purification;

FIG. 24 shows a model of the fusion protein in various combinations; and

Table 11 shows some purification attempts and results (given in the Figures).

DESCRIPTION OF AT LEAST SOME EMBODIMENTS

According to at least some embodiments, the present invention relates to a stable homo-hexamer SCP fusion protein, comprising a Component 1 protein and a Component 2 protein. The Component 1 protein is optionally selected from the group consisting of many receptors or ligands that naturally form homodimers, especially disulfide-linked dimers, e.g., BTN3A1, CD27, CD80, CD86, ENG, NLGN4X, CD84, TIGIT, CD40, IL-8, IL-10, CD164, LY6G6F, CD28, CTLA4, TYROBP, ICOS, VEGFA, CSF1, VEGFB, BMP2, BMP3, GDNF, PDGFC, PDGFD, TGFB1, LY96, CD96 and GFER. Of these component 1 proteins, at least CD28, CTLA4, TYROBP, ICOS, VEGFA, CSF1, VEGFB, BMP2, BMP3, GDNF, PDGFC, PDGFD, TGFB1, LY96, CD96 and GFER form disulfide links to form the homodimers as part of the homo-hexamer formation process.

The Component 2 protein optionally comprises any TNF-superfamily ligand and is preferably selected from the group consisting of FasL, TRAIL, TNF-alpha, TNF-beta, OX40L, CD40L, CD27L, CD30L, 4-1BBL, RANKL, TWEAK, APRIL, BAFF, LIGHT, VEGI, GITRL, EDA1/2, Lymphotoxin alpha and Lymphotoxin beta (reference: Tansey and Szymkowski, Drug Discovery Today, 2009 December; 14(23-24)).

The homo-hexamer may optionally be formed through the formation of covalent bonds, non-covalent bonds or a combination thereof. Optionally, at least the following component 1 proteins form disulfide bonds as part of the homo-hexamer formation process: CD28, CTLA4, TYROBP, ICOS, VEGFA, CSF1, VEGFB, BMP2, BMP3, GDNF, PDGFC, PDGFD, TGFB1, LY96, CD96 and GFER.

Additional information with regard to component 1 proteins is provided in Table 1 below. This information includes details with regard to binding and interaction partners, the biological mechanisms associated with binding to and/or interacting with such binding and interaction partners, and tissue specificity. A similar table is provided for component 2 proteins as Table 2.

It should be noted that TYROBP is listed below (and for the above embodiments) with multiple types of functions, because it is a signaling adapter with dual functionality. Although in association with several receptors it can activate effector cell functions that play a critical role in mediating immune responses against bacterial and viral infections and tumors. TYROBP can also negatively regulate immune responses, including NK cells and macrophages and can play an important role in limiting cytokine production mediated by TLR and FcERIg pathways.

TABLE 1 component 1 protein interactions, function and tissue specificity

| Gene | Binding and interaction | Function | Tissue specificity |
|---|---|---|---|
| CD28 | Interacts with DUSP14. Binds to CD80/B7-1 and CD86/B7-2/B70. | Involved in T-cell activation, the induction of cell proliferation and cytokine production and promotion of T-cell survival. | Expressed in T-cells and plasma cells, but not in less mature B-cells. |
| CTLA4 | The affinity of CTLA4 for its natural B7 family ligands, CD80 and CD86, is considerably stronger than the affinity of their cognate stimulatory coreceptor CD28 | Inhibitory receptor acting as a major negative regulator of T-cell responses. | Widely expressed with highest levels in lymphoid tissues. Detected in activated T-cells where expression levels are 30- to 50-fold less than CD28, the stimulatory coreceptor, on the cell surface following activation. |
| TYROBP | Interacts with SIRPB1 and TREM1. Interacts with CLECSF5. Interacts with SIGLEC14. Interacts with CD300LB and CD300E. Interacts with CD300D . Interacts (via ITAM domain) with SYK (via SH2 domains); activates SYK mediating neutrophils and macrophages integrin-mediated activation. Interacts with KLRC2 and KIR2DS3. | Non-covalently associates with activating receptors of the CD300 family. Cross-linking of CD300-TYROBP complexes results in cellular activation. Involved for instance in neutrophil activation mediated by integrin | Expressed at low levels in the early development of the hematopoietic system and in the promonocytic stage and at high levels in mature monocytes. Expressed in hematological cells and tissues such as peripheral blood leukocytes and spleen. Also found in bone marrow, lymph nodes, placenta, lung and liver. Expressed at lower levels in different parts of the brain especially in the basal ganglia and corpus callosum |
| ICOS | Binds to ICOS ligand. ICOS is highly expressed on tonsillar T-cells, which are closely associated with B-cells in the apical light zone of germinal centers, the site of terminal B-cell maturation. | Enhances all basic T-cell responses to a foreign antigen, namely proliferation, secretion of lymphokines, up-regulation of molecules that mediate cell-cell interaction, and effective help for antibody secretion by B-cells. Essential both for efficient interaction between T and B-cells and for normal antibody responses to T-cell dependent antigens. Does not up-regulate the production of interleukin-2, but superinduces the synthesis of interleukin-10. Prevents the apoptosis of pre-activated T-cells. Plays a critical role in CD40-mediated class switching of immunoglobin isotypes | Activated T-cells. Highly expressed on tonsillar T-cells, which are closely associated with B-cells in the apical light zone of germinal centers, the site of terminal B-cell maturation. Expressed at lower levels in thymus, lung, lymph node and peripheral blood leukocytes. Expressed in the medulla of fetal and newborn thymus. |
| VEGFA | Binds to the FLT1/VEGFR1 and KDR/VEGFR2 receptors, heparan sulfate and heparin. NRP1/Neuropilin-1 binds isoforms VEGF-165 and VEGF-145. Isoform VEGF165B binds to KDR but does not activate downstream signaling pathways, does not activate angiogenesis and inhibits tumor growth. | Growth factor active in angiogenesis, vasculogenesis and endothelial cell growth. Induces endothelial cell proliferation, promotes cell migration, inhibits apoptosis and induces permeabilization of blood vessels | Isoform VEGF189, isoform VEGF165 and isoform VEGF121 are widely expressed. Isoform VEGF206 and isoform VEGF145 are not widely expressed. |
| CSF1 | Interacts with CSF1R | Cytokine that plays an essential role in the regulation of survival, proliferation and differentiation of hematopoietic precursor cells, especially mononuclear phagocytes, such as | CSF1R expressed in bone marrow and in differentiated blood mononuclear cells. |

TABLE 1-continued component 1 protein interactions, function and tissue specificity

| Gene | Binding and interaction | Function | Tissue specificity |
|---|---|---|---|
| | | macrophages and monocytes. Promotes the release of proinflammatory chemokines, and thereby plays an important role in innate immunity and in inflammatory processes. Plays an important role in the regulation of osteoclast proliferation and differentiation, the regulation of bone resorption, and is required for normal bone development. Required for normal male and female fertility. Promotes reorganization of the actin cytoskeleton, regulates formation of membrane ruffles, cell adhesion and cell migration. Plays a role in lipoprotein clearance | |
| VEGFB | VEGF-B167 binds heparin and neuropilin-1 whereas the binding to neuropilin-1 of VEGF-B186 is regulated by proteolysis. | Growth factor for endothelial cells | Expressed in all tissues except liver. Highest levels found in heart, skeletal muscle and pancreas. |
| BMP2 | Interacts with SOSTDC1. Interacts with GREM2, RGMA, RGMB and RGMC. Interacts with ASPN | Induces cartilage and bone formation. | Particularly abundant in lung, spleen and colon and in low but significant levels in heart, brain, placenta, liver, skeletal muscle, kidney, pancreas, prostate, ovary and small intestine. |
| BMP3 | | Negatively regulates bone density. Antagonizes the ability of certain osteogenic BMPs to induce osteoprogenitor differentiation and ossification. | Expressed in adult and fetal cartilage. Highly expressed in fracture tissue, particularly in osteoblasts, osteoclasts and chondroblasts. |
| GDNF | Induction by cAMP, 12-O-tetradecanoylphorbol-13-acetate (TPA) and FGF2 | Neurotrophic factor that enhances survival and morphological differentiation of dopaminergic neurons and increases their high-affinity dopamine uptake. | In the brain, predominantly expressed in the striatum with highest levels in the caudate and lowest in the putamen. Isoform 2 is absent from most tissues except for low levels in intestine and kidney. Highest expression of isoform 3 is found in pancreatic islets. Isoform 5 is expressed at very low levels in putamen, nucleus accumbens, prefrontal cortex, amygdala, hypothalamus and intestine. Isoform 3 is up-regulated in the middle temporal gyrus of Alzheimer disease patients while isoform 2 shows no change. |
| PDGFC | Interacts with PDGFRA homodimers, and with heterodimers formed by PDGFRA and PDGFRB. Interacts (via CUB domain) with PLAT (via kringle domain). Up-regulated by EWS-FLI1 chimeric transcription factor in tumor derived cells. Up-regulated in podocytes and interstitial cells after injury/activation of these cells. FGF2 activates PDGFC transcription via EGR1. Up-regulated by TGFB1 in concert with FGF2. | Growth factor that plays an essential role in the regulation of embryonic development, cell proliferation, cell migration, survival and chemotaxis. Potent mitogen and chemoattractant for cells of mesenchymal origin. Required for normal skeleton formation during embryonic development, especially for normal development of the craniofacial skeleton and for normal development of the palate. Required for normal skin morphogenesis during embryonic development. Plays an important role in wound healing, where it appears to be involved in three stages: inflammation, proliferation and remodeling. Plays an important role in angiogenesis and blood vessel development. Involved in fibrotic processes, in which | Expressed in the fallopian tube, vascular smooth muscle cells in kidney, breast and colon and in visceral smooth muscle of the gastrointestinal tract. Highly expressed in retinal pigment epithelia. Expressed in medulloblastoma. In the kidney, constitutively expressed in parietal epithelial cells of Bowman's capsule, tubular epithelial cells and in arterial endothelial cells (at protein level). Highly expressed in the platelets, prostate, testis and uterus. Higher expression is observed in uterine leiomyomata. Weaker expression in the spleen, thymus, heart, pancreas, liver, ovary cells and small intestine, and negligible expression in the colon and peripheral blood leukocytes |

TABLE 1-continued component 1 protein interactions, function and tissue specificity

| Gene | Binding and interaction | Function | Tissue specificity |
|---|---|---|---|
| | | transformation of interstitial fibroblasts into myofibroblasts plus collagen deposition occurs. The CUB domain has mitogenic activity in coronary artery smooth muscle cells, suggesting a role beyond the maintenance of the latency of the PDGF domain. In the nucleus, PDGFC seems to have additional function | |
| PDGFD | Interacts with PDGFRB homodimers, and with heterodimers formed by PDGFRA and PDGFRB | Growth factor that plays an essential role in the regulation of embryonic development, cell proliferation, cell migration, survival and chemotaxis. Potent mitogen for cells of mesenchymal origin. Plays an important role in wound healing. Induces macrophage recruitment, increased interstitial pressure, and blood vessel maturation during angiogenesis. Can initiate events that lead to a mesangial proliferative glomerulonephritis, including influx of monocytes and macrophages and production of extracellular matrix | Expressed at high levels in the heart, pancreas, adrenal gland and ovary and at low levels in placenta, liver, kidney, prostate, testis, small intestine, spleen and colon. In the kidney, expressed by the visceral epithelial cells of the glomeruli. A widespread expression is also seen in the medial smooth muscle cells of arteries and arterioles, as well as in smooth muscle cells of vasa rectae in the medullary area. Expressed in the adventitial connective tissue surrounding the suprarenal artery. In chronic obstructive nephropathy, a persistent expression is seen in glomerular visceral epithelial cells and vascular smooth muscle cells, as well as de novo expression by periglomerular interstitial cells and by some neointimal cells of atherosclerotic vessels. Expression in normal prostate is seen preferentially in the mesenchyme of the gland while expression is increased and more profuse in prostate carcinoma. Expressed in many ovarian, lung, renal and brain cancer-derived cell lines. |
| TGFB1 | Secreted and stored as a biologically inactive form in the extracellular matrix in a 290 kDa complex (large latent TGF-betal complex) containing the TGFB1 homodimer, the latency-associated peptide (LAP), and the latent TGFB1 binding protein-1 (LTBP1). The complex without LTBP1 is known as the 'small latent TGF-betal complex'. Dissociation of the TGFB1 from LAP is required for growth factor activation and biological activity. Release of the large latent TGF-betal complex from the extracellular matrix is carried out by the matrix metalloproteinase MMP3 By. May interact with THSD4; this interaction may lead to sequestration by FBN1 microfibril assembly and attenuation of TGFB signaling. Interacts with the serine proteases, HTRA1 and HTRA3: the interaction with either inhibits TGFB1-mediated signaling. The HTRA protease activity is required for this inhibition. Latency-associated peptide interacts with NREP; the interaction results in a decrease in TGFB1 autoinduction. Interacts with CD109, DPT and ASPN. | Multifunctional protein that controls proliferation, differentiation and other functions in many cell types. Many cells synthesize TGFB1 and have specific receptors for it. It positively and negatively regulates many other growth factors. It plays an important role in bone remodeling as it is a potent stimulator of osteoblastic bone formation, causing chemotaxis, proliferation and differentiation in committed osteoblasts. | Highly expressed in bone. Abundantly expressed in articular cartilage and chondrocytes and is increased in osteoarthritis (OA). Colocalizes with ASPN in chondrocytes within OA lesions of articular cartilage. |
| LY96 | Binds to the extracellular domains of TLR2 and TLR4. Ligand binding induces interaction with TLR4 and oligomerization of the complex. | Cooperates with TLR4 in the innate immune response to bacterial lipopolysaccharide (LPS), and with TLR2 in the response to cell wall components from Gram-positive and Gram-negative bacteria. Enhances TLR4-dependent activation of | |

TABLE 1-continued component 1 protein interactions, function and tissue specificity

| Gene | Binding and interaction | Function | Tissue specificity |
|---|---|---|---|
| CD96 | Interacts with PVR. | NF-kappa-B. Cells expressing both MD2 and TLR4, but not TLR4 alone, respond to LPS. May be involved in adhesive interactions of activated T and NK cells during the late phase of the immune response. Promotes NK cell-target adhesion by interacting with PVR present on target cells. May function at a time after T and NK cells have penetrated the endothelium using integrins and selectins, when they are actively engaging diseased cells and moving within areas of inflammation. | Expressed on normal T-cell lines and clones, and some transformed T-cells, but no other cultured cell lines tested. It is expressed at very low levels on activated B-cells. |
| GFER | | Isoform 2 Cytoplasm. Secreted: May act as an autocrine hepatotrophic growth factor promoting liver regeneration. | Ubiquitously expressed. Highest expression in the testis and liver and low expression in the muscle |
| BTN3A1 | | Plays a role in T-cell activation and in the adaptive immune response. Regulates the proliferation of activated T-cells. Regulates the release of cytokines and IFNG by activated T-cells. Mediates the response of T-cells toward infected and transformed cells that are characterized by high levels of phosphorylated metabolites, such as isopentenyl pyrophosphate. | Detected on T-cells, natural killer cells, dendritic cells and macrophages (at protein level). Ubiquitous. Highly expressed in heart, pancreas and lung, Moderately expressed in placenta, liver and muscle |
| CD27 | Interacts with CD70 (It is a surface antigen on activated, but not on resting, T and B lymphocytes.), SIVA1 and TRAF2. | This receptor is required for generation and long-term maintenance of T cell immunity. It binds to ligand CD70, and plays a key role in regulating B-cell activation and immunoglobulin synthesis. This receptor transduces signals that lead to the activation of NF-kappaB and MAPK8/JNK. Adaptor proteins TRAF2 and TRAF5 have been shown to mediate the signaling process of this receptor. CD27-binding protein (SIVA), a proapoptotic protein, can bind to this receptor and is thought to play an important role in the apoptosis induced by this receptor. | Found in most T-lymphocytes. |
| CD80 | binding to CD28, CTLA-4 | Involved in the co stimulatory signal essential for T-lymphocyte activation. T-cell proliferation and cytokine production is induced by the binding of CD28, binding to CTLA-4 has opposite effects and inhibits T-cell activation. | Expressed on activated B-cells, macrophages and dendritic cells. |

TABLE 1-continued component 1 protein interactions, function and tissue specificity

| Gene | Binding and interaction | Function | Tissue specificity |
| --- | --- | --- | --- |
| CD86 | binding CD28 or CTLA-4. | Receptor involved in the costimulatory signal essential for T-lymphocyte proliferation and interleukin-2 production, by binding CD28 or CTLA-4. May play a critical role in the early events of T-cell activation and costimulation of naive T-cells, such as deciding between immunity and anergy that is made by T-cells within 24 hours after activation. Isoform 2 interferes with the formation of CD86 clusters, and thus acts as a negative regulator of T-cell activation. | Expressed by activated B-lymphocytes and monocytes |
| ENG | It is able to bind TGF-beta 1, and 3 efficiently and TGF-beta 2 less efficiently. Interacts with TCTEX1D4. Interacts with ARRB2. Interacts with GDF2. | Major glycoprotein of vascular endothelium. Involved in the regulation of angiogenesis. May play a critical role in the binding of endothelial cells to integrins and/or other RGD receptors. Acts as TGF-beta coreceptor and is involved in the TGF-beta/BMP signaling cascade. Required for GDF2/BMP9 signaling through SMAD1 in endothelial cells and modulates TGF-beta 1 signaling through SMAD3. | Endoglin is restricted to endothelial cells in all tissues except bone marrow. |
| NLGN4X | Interacts with NRXN1 in a calcium-dependent manner. Interacts through its C-terminus with DLG4/PSD-95 third PDZ domain. | Putative neuronal cell surface protein involved in cell-cell-interactions. | Expressed at highest levels in heart. Expressed at lower levels in liver, skeletal muscle and pancreas and at very low levels in brain. |
| CD84 | Forms a head to tail dimer with a CD48 molecule from another cell. Interacts with SH2 domain-containing proteins SH2D1A/SAP and SH2D1B/hEAT-2. Interacts with tyrosine-protein phosphatases PTPN6 and PTPN11 via its phosphorylated cytoplasmic domain, and this interaction is blocked by SH2D1A. | Plays a role as adhesion receptor functioning by homophilic interactions and by clustering. Recruits SH2 domain-containing proteins SH2D1A/SAP. Increases proliferative responses of activated T-cells and SH2D1A/SAP does not seen be required for this process. Homophilic interactions enhance interferon gamma/IFNG secretion in lymphocytes and induce platelet stimulation via a SH2D1A/SAP-dependent pathway. May serve as a marker for hematopoietic progenitor cells | Predominantly expressed in hematopoietic tissues, such as lymph node, spleen and peripheral leukocytes. Expressed in macrophages, B-cells, monocytes, platelets, thymocytes, T-cells and dendritic cells. Highly expressed in memory T-cells. |
| TIGIT | binds with high affinity to PVR, forming a heterotetrameric assembly of two TIGIT and two PVR molecules. Binds with lower affinity to PVRL2 and PVRL3. | Binds with high affinity to the poliovirus receptor (PVR) which causes increased secretion of IL10 and decreased secretion of IL12B and suppresses T-cell activation by promoting the generation of mature immunoregulatory dendritic cells. | Expressed at low levels on peripheral memory and regulatory CD4+ T-cells and NK cells and is up-regulated following activation of these cells (at protein level). |
| CD40 | CD40L | This receptor has been found to be essential in mediating a broad variety of immune and inflammatory responses including T cell-dependent immunoglobulin class switching, memory B cell development, and germinal center formation. | B-cells and in primary carcinomas. |
| IL-8 | | IL-8 is a chemotactic factor that attracts neutrophils, basophils, and T-cells, but not monocytes. It is also involved in neutrophil activation. It is released from several cell types in response to an inflammatory stimulus. IL- | |

TABLE 1-continued

| | component 1 protein interactions, function and tissue specificity | | |
|---|---|---|---|
| Gene | Binding and interaction | Function | Tissue specificity |
| | | 8(6-77) has a 5-10-fold higher activity on neutrophil activation, IL-8(5-77) has increased activity on neutrophil activation and IL-8(7-77) has a higher affinity to receptors CXCR1 and CXCR2 as compared to IL-8(1-77), respectively. | |
| IL-10 | | This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production. This cytokine can block NF-kappa B activity, and is involved in the regulation of the JAK-STAT signaling pathway. Inhibits the synthesis of a number of cytokines, including IFN-gamma, IL-2, IL-3, TNF and GM-CSF produced by activated macrophages and by helper T-cells | Produced by a variety of cell lines, including T-cells, macrophages, mast cells and other cell types. |
| CD164 | Interacts with CXCR4 | Sialomucin that may play a key role in hematopoiesis by facilitating the adhesion of CD34$^+$ cells to the stroma and by negatively regulating CD34$^+$CD38(lo/−) cell proliferation. Modulates the migration of umbilical cord blood CD133+ cells and this is mediated through the CXCL12/CXCR4 axis. May play an important role in prostate cancer metastasis and the infiltration of bone marrow by cancer cells. Promotes myogenesis by enhancing CXCR4-dependent cell motility. Positively regulates myoblast migration and promotes myoblast fusion into myotubes | Isoform 1 and isoform 3 are expressed in hematopoietic and non-hematopoietic tissues. Isoform 1 is expressed by prostate cancer tumors and prostate cancer cell lines. The expression is greater in bone metastases than in primary tumors. Expression in osseous metastasis is greater than that in soft tissue metastasis. Isoform 2 is expressed in the small intestine, colon, lung, thyroid and in colorectal and pancreatic adenocarcinoma. Isoform 4 is expressed by both hematopoietic progenitor cells and bone marrow stromal cells. |
| CD84 | Forms a head to tail dimer with a CD48 molecule from another cell. Interacts with SH2 domain-containing proteins SH2D1A/SAP and SH2D1B/hEAT-2. Interacts with tyrosine-protein phosphatases PTPN6 and PTPN11 via its phosphorylated cytoplasmic domain, and this interaction is blocked by SH2D1A | Plays a role as adhesion receptor functioning by homophilic interactions and by clustering. Recruits SH2 domain-containing proteins SH2D1A/SAP. Increases proliferative responses of activated T-cells and SH2D1A/SAP does not seem be required for this process. Homophilic interactions enhance interferon gamma/IFNG secretion in lymphocytes and induce platelet stimulation via a SH2D1A/SAP-dependent pathway. May serve as a marker for hematopoietic progenitor cells. | Predominantly expressed in hematopoietic tissues, such as lymph node, spleen and peripheral leukocytes. Expressed in macrophages, B-cells, monocytes, platelets, thymocytes, T-cells and dendritic cells. Highly expressed in memory T-cells |
| LY6G6F | Interacts with GRB2 and GRB7 in a phosphorylation-dependent manner. | May play a role in the downstream signal transduction pathways involving GRB2 and GRB7. | |

TABLE 2 component 2 protein interactions, function and tissue specificity

| Gene | Binding and interaction | Function | Tissue specificity |
| --- | --- | --- | --- |
| FASL | Binds to TNFRSF6/FAS. Interacts with ARHGAP9, BAIAP2L1, BTK, CACNB3, CACNB4, CRK, DLG2, DNMBP, DOCK4, EPS8L3, FGR, FYB, FYN, HCK, ITK, ITSN2, KALRN, LYN, MACC1, MIA, MPP4, MYO15A, NCF1, NCK1, NCK2, NCKIPSD, OSTF1, PIK3R1, PSTPIP1, RIMBP3C, SAMSN1, SH3GL3, SH3PXD2B, SH3PXD2A, SH3RF2, SKAP2, SNX33, SNX9, SORBS3, SPTA1, SRC, SRGAP1, SRGAP2, SRGAP3, TEC, TJP3 and YES1. | Cytokine that binds to TNFRSF6/FAS, a receptor that transduces the apoptotic signal into cells. May be involved in cytotoxic T-cell mediated apoptosis and in T-cell development. TNFRSF6/FAS-mediated apoptosis may have a role in the induction of peripheral tolerance, in the antigen-stimulated suicide of mature T-cells, or both. Binding to the decoy receptor TNFRSF6B/DcR3 modulates its effects. | |
| TRAIL | Cytokine that binds to TNFRSF10A/TRAILR1, TNFRSF10B/TRAILR2, TNFRSF10C/TRAILR3, TNFRSF10D/TRAILR4 and possibly also to TNFRSF11B/OPG. | Induces apoptosis. | Widespread; most predominant in spleen, lung and prostate. |
| TNF | Cytokine that binds to TNFRSF1A/TNFR1 and TNFRSF1B/TNFBR. | It is mainly secreted by macrophages and can induce cell death of certain tumor cell lines. It is potent pyrogen causing fever by direct action or by stimulation of interleukin-1 secretion and is implicated in the induction of cachexia, Under certain conditions it can stimulate cell proliferation and induce cell differentiation. | |
| OX40L | Cytokine that binds to TNFRSF4 (OX40/CD134) | Co-stimulates T-cell proliferation and cytokine production. | OX40 (CD134) is a potent co stimulatory molecule found on the surface of activated CD4(+) and CD8(+) T cells. Specifically expressed on activated CD4+ T-lymphocytes. |
| CD40L | CD40 on B cells | The protein encoded by this gene is expressed on the surface of T cells. It regulates B cell function by engaging CD40 on the B cell surface. Mediates B-cell proliferation in the absence of co-stimulus as well as IgE production in the presence of IL-4. Involved in immunoglobulin class switching | |
| CD27L | Cytokine that binds to CD27 (Found in most T-lymphocytes.) | Cytokine that binds to CD27. Plays a role in T-cell activation. Induces the proliferation of costimulated T-cells and enhances the generation of cytolytic T-cells. | It is a surface antigen on activated, but not on resting, T and B lymphocytes. |
| CD30L | Binds to CD30 which expressed by activated, but not by resting, T and B cells. | The protein encoded by this gene is a cytokine that belongs to the tumor necrosis factor (TNF) ligand family. This cytokine is a ligand for TNFRSF8/CD30, which is a cell surface antigen and a marker for Hodgkin lymphoma and related hematologic malignancies. The engagement of this cytokine expressed on B cell surface plays an inhibitory role in modulating Ig class switch. This cytokine was shown to enhance cell proliferation of some lymphoma cell lines, while to induce cell death and reduce cell proliferation of other lymphoma cell lines. Induces proliferation of T-cells. | CD30 expressed by activated, but not by resting, T and B cells. |
| 4-1 BBL | Cytokine that binds to TNFRSF9. | Induces the proliferation of activated peripheral blood T-cells. May have a role in activation-induced cell death (AICD). May play a role in cognate interactions between T-cells and B-cells/macrophages | Expressed in brain, placenta, lung, skeletal muscle and kidney. TNFRSF9 Expressed on the surface of activated T-cells. |
| RANKL | Cytokine that binds to TNFRSF11B/OPG and to TNFRSF11A/RANK | Osteoclast differentiation and activation factor. Augments the ability of dendritic cells to stimulate naive T-cell proliferation. May be an important regulator of interactions between T-cells and dendritic cells and may play a role in the regulation of the T-cell-dependent immune response. May also play an important role in enhanced bone-resorption in humoral hypercalcemia of malignancy. | Highest in the peripheral lymph nodes, weak in spleen, peripheral blood Leukocytes, bone marrow, heart, placenta, skeletal muscle, stomach and thyroid. |

TABLE 2-continued component 2 protein interactions, function and tissue specificity

| Gene | Binding and interaction | Function | Tissue specificity |
| --- | --- | --- | --- |
| TWEAK | This protein is a ligand for the FN14/TWEAKR receptor. Interacts with the angiogenic factor AGGF1/VG5Q. | Binds to FN14 and possibly also to TNRFSF12/APO3. Weak inducer of apoptosis in some cell types. Mediates NF-kappa-B activation. Promotes angiogenesis and the proliferation of endothelial cells. Also involved in induction of inflammatory cytokines. Promotes IL8 secretion. | TWEAK is highly expressed in adult heart, pancreas, skeletal muscle, brain, colon, small intestine, lung, ovary, prostate, spleen, lymph node, appendix and peripheral blood lymphocytes. Low expression in kidney, testis, liver, placenta, thymus and bone marrow. Also detected in fetal kidney, liver, lung and brain. FN14 Highly expressed in heart, placenta and kidney. Intermediate expression in lung, skeletal muscle and pancreas. |
| APRIL | Cytokine that binds to TNFRSF13B/TACI and to TNFRSF17/BCMA. | This protein is a ligand for TNFRSF17/BCMA, a member of the TNF receptor family. This protein and its receptor are both found to be important for B cell development. In vitro experiments suggested that this protein may be able to induce apoptosis through its interaction with other TNF receptor family proteins such as TNFRSF6/FAS and TNFRSF14/HVEM. Plays a role in the regulation of tumor cell growth. May be involved in monocyte/macrophage-mediated immunological processes | Expressed at high levels in transformed cell lines, cancers of colon, thyroid, lymphoid tissues and specifically expressed in monocytes and macrophages. APRIL receptor Expressed in mature B-cells, but not in T-cells or monocytes. |
| BAFF | Binds to BAFF receptor | Cytokine that binds to TNFRSF13B/TACI and TNFRSF17/BCMA. TNFSF13/APRIL binds to the same 2 receptors. Together, they form a 2 ligands -2 receptors pathway involved in the stimulation of B-and T-cell function and the regulation of humoral immunity. A third B-cell specific BAFF-receptor (BAFFR/BR3) promotes the survival of mature B-cells and the B-cell response. | Abundantly expressed in peripheral blood Leukocytes and is specifically expressed in monocytes and macrophages. Also found in the spleen, lymph node, bone marrow, T-cells and dendritic cells. A lower expression seen in placenta, heart, lung, fetal liver, thymus, and pancreas. BAFF receptor Highly expressed in spleen and lymph node, and in resting B-cells. Detected at lower levels in activated B-cells, resting CD4+ T-cells, in thymus and peripheral blood leukocytes. |
| LIGHT (TNFSF14) | | The protein encoded by this gene is a member of the tumor necrosis factor (TNF) ligand family. This protein is a ligand for TNFRSF14, which is a member of the tumor necrosis factor receptor superfamily, and which is also known as a herpesvirus entry mediator (HVEM). This protein may function as a co stimulatory factor for the activation of lymphoid cells and as a deterrent to infection by herpesvirus. This protein has been shown to stimulate the proliferation of T cells, and trigger apoptosis of various tumor cells. This protein is also reported to prevent tumor necrosis factor alpha mediated apoptosis in primary hepatocyte. Two alternatively spliced transcript variant encoding distinct isoforms have been report | |
| VEGI | Ligand of TNFRSF25 and TNFRSF6B | The protein encoded by this gene is a cytokine that belongs to the tumor necrosis factor (TNF) ligand family. This protein is abundantly expressed in endothelial cells, but is not expressed in either B or T cells. The expression of this protein is inducible by TNF and IL-1 alpha. This cytokine is a ligand for receptor TNFRSF25 and decoy receptor TNFRSF21/DR6. It can activate NF-kappaB and MAP kinases, and acts as an autocrine factor to induce apoptosis in endothelial cells. This cytokine is also | Specifically expressed in endothelial cells. Detected in monocytes, placenta, lung, liver, kidney, skeletal muscle, pancreas, spleen, prostate, small intestine and colon. VEGI receptor Abundantly expressed in thymocytes and lymphocytes. Detected in lymphocyte-rich tissues such as thymus, colon, intestine, and spleen. Also found in the |

TABLE 2-continued component 2 protein interactions, function and tissue specificity

| Gene | Binding and interaction | Function | Tissue specificity |
|---|---|---|---|
| | | found to inhibit endothelial cell proliferation, and thus may function as an angiogenesis inhibitor | prostate. |
| GITRL | Cytokine that binds to TNFRSF18/AITR/GITR | Regulates T-cell responses. Can function as costimulator and lower the threshold for T-cell activation and T-cell proliferation. Important for interactions between activated T-lymphocytes and endothelial cells. Mediates activation of NF-kappa-B. Receptor for TNFSF18. Seems to be involved in interactions between activated T-lymphocytes and endothelial cells and in the regulation of T-cell receptor-mediated cell death. Mediated NF-kappa-B activation via the TRAF2/NIK pathway. | Expressed at high levels in the small intestine, ovary, testis, kidney and endothelial cells. GITR receptor expressed in lymph node, peripheral blood leukocytes and weakly in spleen. |
| EDA1 | | The protein encoded by this gene is a type II membrane protein that can be cleaved by furin to produce a secreted form. The encoded protein, which belongs to the tumor necrosis factor family, acts as a homotrimer and may be involved in cell-cell signaling during the development of ectodermal organs. Defects in this gene are a cause of ectodermal dysplasia, anhidrotic, which is also known as X-linked hypohidrotic ectodermal dysplasia. Several transcript variants encoding many different isoforms have been found for this gene | |
| TNF alpha | Cytokine that binds to TNFRSF1A/TNFR1 and TNFRSF1B/TNFBR. | It is mainly secreted by macrophages and can induce cell death of certain tumor cell lines. It is potent pyrogen causing fever by direct action or by stimulation of interleukin-1 secretion and is implicated in the induction of cachexia, Under certain conditions it can stimulate cell proliferation and induce cell differentiation. Receptor for TNFSF2/TNF-alpha and homotrimeric TNFSF1/lymphotoxin-alpha. The adapter molecule FADD recruits caspase-8 to the activated receptor. The resulting death-inducing signaling complex (DISC) performs caspase-8 proteolytic activation which initiates the subsequent cascade of caspases (aspartate-specific cysteine proteases) mediating apoptosis. Contributes to the induction of non-cytocidal TNF effects including anti-viral state and activation of the acid sphingomyelinase. | |
| TNF beta | Cytokine that in its homotrimeric form binds to TNFRSF1A/TNFR1, TNFRSF1B/TNFBR and TNFRSF14/HVEM. In its heterotrimeric form with LTB binds to TNFRSF3/LTBR. | The protein is highly inducible, secreted, and forms heterotrimers with lymphotoxin-beta which anchor lymphotoxin-alpha to the cell surface. This protein also mediates a large variety of inflammatory, immunostimulatory, and antiviral responses, is involved in the formation of secondary lymphoid organs during development and plays a role in apoptosis. Genetic variations in this gene are associated with susceptibility to leprosy type 4, myocardial infarction, non-Hodgkin's lymphoma, and psoriatic arthritis. Alternatively spliced transcript variants have been observed for this gene. Receptor for TNFSF2/TNF-alpha and homotrimeric TNFSF1/lymphotoxin-alpha. The adapter molecule FADD recruits caspase-8 to the activated receptor. The resulting death-inducing signaling complex (DISC) performs caspase-8 proteolytic activation which initiates the subsequent cascade of caspases (aspartate-specific cysteine proteases) mediating apoptosis. Contributes to the induction of non- | |

TABLE 2-continued component 2 protein interactions, function and tissue specificity

| Gene | Binding and interaction | Function | Tissue specificity |
|------|------------------------|----------|--------------------|
|      |                        | cytocidal TNF effects including anti-viral state and activation of the acid sphingomyelinase. |  |

Table 3 provides a description for determining which component 1 and component 2 proteins can partner. Specifically, Table 3 lists various disease indications, followed by component 1 activities and then component 1 proteins, followed by component 2 activities and component 2 protein partners for the component 1 proteins.

According to at least some embodiments of the present invention, for each disease indication, any listed component 1 protein in that row can partner with any listed component 2 protein in that row. However, this list is meant for the purposes of illustration only and is not intended to be limiting in any way. Furthermore, the combinations described below may optionally be used to treat other (alternative or additional) diseases, while the diseases below may optionally be treated with other (alternative or additional) combinations.

DNA sequences were codon-optimized for expression in CHO (Cricetulus griseus), negative elements and GC content were adjusted to potentially increase expression in mammalian cells. The selected DNA sequences were then synthesized and cloned into a UCOE containing expression vector (Antoniou at al, Genomics. 2003 September; 82(3): 269-79) by GENEART. Full sequencing and restriction analysis showed the expected DNA sequence and the correct gene orientation in the expression vector.

```
CTLA4-FasL amino-acid sequence
                                        (SEQ ID NO: 1)
AMHVAQPAVVLASSRGIASFVCEYASPGKATEVRVTVLRQADSQVTEVCA

ATYMMGNELTFLDDSICTGTSSGNQVNLTIQGLRAMDTGLYICKVELMYP
```

TABLE 3

| | Indications | Component 1 activities | Component 1 proteins | Component 2 activities | Component 2 proteins |
|---|---|---|---|---|---|
| 1 | immune induction (e.g., for treatment of cancer) | immune-targeting or immune-induction activities | CD28, CSF1, LY96, CD96, BTN3A1, TIGIT, IL8, IL10, CD80, CD86, LY96 | induce the immune system and induce growth | TNF, OX40L, CD40L, CD27L, CD30L, 4-1BBL, TWEAK, APRIL, BAFF, LIGHT, GITRL |
| 2 | immune suppression and cancer cell apoptosis | immune-targeting or immune-inhibitory activities | CTLA4, CD40, TYROBP, CD27, ENG | activate apoptosis or suppress growth | FasL, TRAIL, VEGI |
| 3 | induction of angiogenesis | angiogenic activities | VEGFA | activate angiogenesis or activate growth | TWEAK, APRIL |
| 4 | inhibition of angiogenesis | anti-angiogenic activities | ENG | suppress angiogenesis or activate apoptosis | FasL, TRAIL, VEGI |
| 5 | induction of bone formation | bone formation activities | BMP2 | activate cell growth and bone formation | TWEAK, APRIL |
| 6 | inhibition of bone formation | inhibitory bone formation activities | BMP3 | activities activate bone resorption, apoptosis or suppress growth | RNAKL, FasL, TRAIL, VEGI |
| 7 | liver regeneration | liver regeneration activities | GFER | activate angiogenesis or activate growth | TWEAK, APRIL |

CTLA4-FasL as Non-Limiting Example of Homo-Hexamer SCP Fusion Protein

As described herein, many different component 1 and component 2 proteins, as well as functional portions thereof, may optionally form fusion proteins that have stable homo-hexamer forms. CTLA4-FasL fusion protein is a non-limiting example of such a fusion protein, for which detailed experimental methods and results are described below. However, the present inventors believe that the other component 1 and component 2 proteins (and functional portions thereof) would form SCP fusion proteins showing at least similar behavior.

Materials and Methods

Construction and Isolation of a CHO-S Production Clone

The CTLA4-FasL amino acid sequence of FIG. 1A (including the signal peptide, SEQ ID NO:2) was 'back translated' into DNA by using Invitrogen's VectorNTI software. The DNA sequence for the Human Urokinase Signal peptide (NM_002658) together with a 5' untranslated sequence was added and a signal peptide-cleave prediction program (SignalP-HMM) was used to confirm correct cleavage-site. The

```
         -continued
PPYYLGIGNGTQIYVIDPEPCPDSG SLEKQIGHPSPPPEKKELRKVAHL

TGKSNSRSMPLEWEDTYGIVLLSGVKYKKGGLVINETGLYFVYSKVYFRG

QSCNNLPLSHKVYMRNSKYPQDLVMMEGKMMSYCTTGQMWARSSYLGAVF

NLTSADHLYVNVSELSLVNFEESQTFFGLYKL
```

Figure 1B:
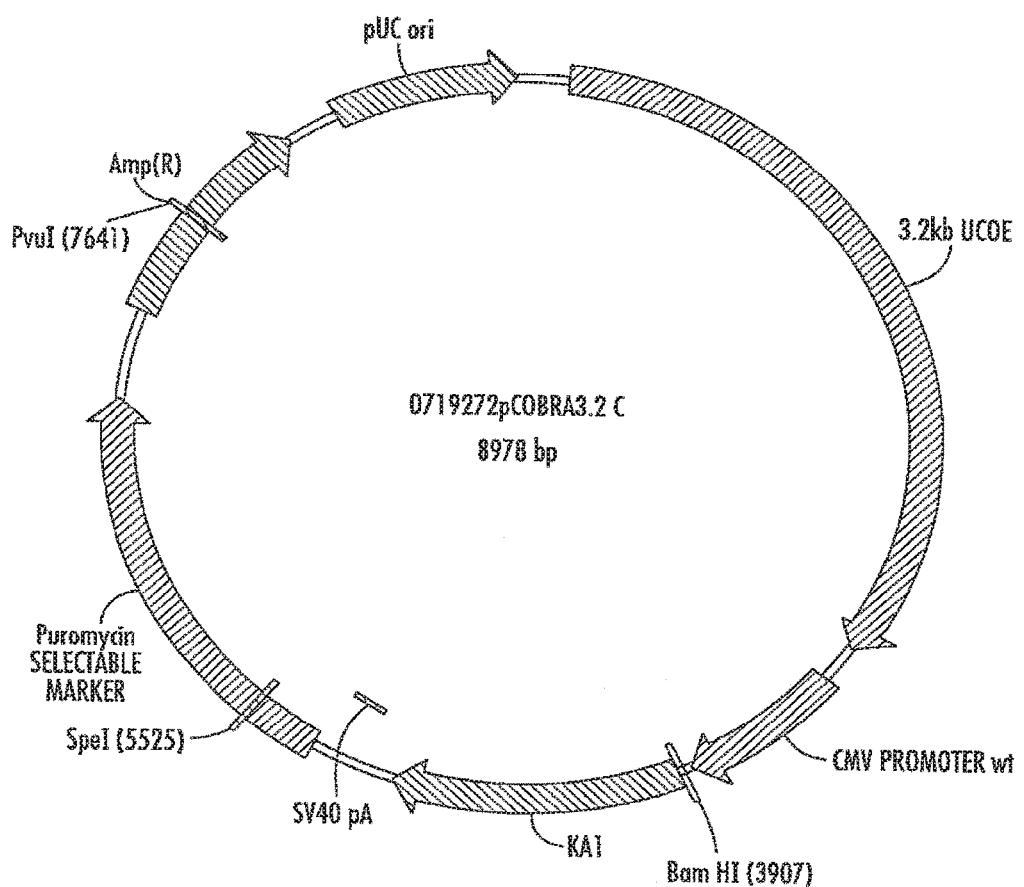

CHO-S cells were transfected with the UCOE/CTLA4-FasL expression vector, shown in FIG. 1B, linearized with the restriction enzyme PvuI and purified using Amersham GFX columns before re suspending in sterile water. CHO-S cells were grown in CD-CHO medium and transfected with 30 micrograms of linearized DNA using DMRIE-C as the transfection agent. Twenty-four hours after transfection, cell pools were harvested and re suspended in 20 mL of Mix6 medium (CD-CHO/Medium 5 mix) with puromycin at 12.5 micrograms/mL. Cells were then maintained on puromycin selection at approximately 1×10⁶/mL with periodic changes of media until the viability had recovered to greater than 95% and sufficient cells were available to generate a number of frozen vials for each culture (frozen at 1×10⁷/mL). After 1 week growth, supernatant samples were removed and CTLA4-FasL was quantified by a commercial FasL ELISA kit.

Clones with the highest expression were then expanded into 10 ml Mix6 in 125 ml shaker flasks at 50 rpm and maintained on puromycin selection. After 4 days the shaker speed was increased to 100 rpm and cells were counted for viability at regular intervals and expanded as necessary. Expression analysis was performed on clones under standard non-supplemented media conditions at small scale in 125 ml shaker flasks. Cultures were maintained until cell viability approached 80% and expression levels were then estimated by FasL ELISA. The protein product was analyzed by SDS-PAGE and Western blots showing that all clones produce a protein product of similar size and one clone, showing the highest levels of expression, was selected for limiting dilution. Limiting dilutions were carried out in two different occasions with 7 days in between; in the first seeding occasion, cells were seeded in 96 well plates in 50% conditioned media at cells/well ratios of 800, 400, 200, 100, 50, 25, and 10 cells per well. Based on FasL ELISA analysis of the first seeding ratios, cells were diluted to lower seeding densities of; 50, 25, 12.5, 6.25, 3.13, 1.56, and 0.78 cells per well. The 96-well plates were incubated in a HeraCell incubator for 2-3 weeks at which point all plates were assessed visually for growth. Clones with the lowest seeding cell density were selected from the 96-well plates and transferred to 24-well plates and diluted 1:10 in cell culture media. After 7 days of culture the cell suspension was harvested and analyzed by ELISA and the ten highest producing clones were transferred from 24-well plates to 6-well plates by a dilution of 1:4 in cell culture media. When sufficient cells had been received in 6-well plates, the ten clones were transferred from 6-well plates to 125 mL shake flasks and their growth profile and CTLA4-FasL expression investigated. One clone was selected as the final clone based on that analysis.

SDS-PAGE and Western Blotting

Sodium dodecyl sulfate polyacrylamide gel electrophoresis (SDS-PAGE) was performed by using 4-12% Bis-Tris gel (1 mm, 12 wells, NP0322BOX, Life Technologies) and "See Blue Plus 2" MW markers (LC5925, Life Technologies). Proteins were transferred to a PVDF-membrane and the membrane blocked using dried milk. The primary antibodies were either goat anti-human CTLA4 antibody (AF-386-PB, RandD Systems, 1:300 dilution) or goat anti-human Fas Ligand (AB 126, RandD Systems, 1:100 dilution). The secondary antibody was a donkey anti-Sheep/Goat Immunoglobulins (HRP, AP360, The Binding Site, 1:10,000 dilution), detected by HRP substrate 3,3', 5,5'-Tetramethylbenzidine (TMB, Liquid Substrate System for Membranes, T0565, Sigma).

For Western blot analysis of intracellular proteins, whole cell lysates were separated on 10% SDS-PAGE and blotted according to standard procedures.

Membranes were incubated with the following primary antibodies: anti Caspase-3, anti Caspase-8, anti Caspase-9, PARP, Bcl-2, IAP-1,2, pNFkB, pJNK, pERK1/2 (1:1000), (Cell Signaling Technology, Danvers, Mass., USA); XIAP (1:100) (Santa Cruz Biotechnology, Santa Cruz, Calif., USA); FLIP (1:500) (Enzo, Calif., USA); BID (1:4000), IkB (1:20,000) (RandD, Minneapolis, Minn., USA); Bcl-x (1:1000) (BD Biosciences, NJ, USA); GAPDH (1:500; Millipore, Billerica, Mass., USA). Secondary detection was performed with HRP-conjugated antibodies (1:10,000; Biorad, Hercules, Calif., USA).

Native-PAGE analysis was performed with NativePAGE™ Novex® 4-16% Bis-Tris Gel (Invitrogen), according to the manufacturer protocol. Samples were prepared with and without G-250 sample additive. 10uL of the CTLA4-FasL sample and of the NativeMark were loaded to each gel lane. Coomassie G-250 was added to the cathode buffer and to the samples, resulting in staining of the proteins during gel electrophoresis.

Con-A/SEC Purification Process

Thawed production harvest was centrifuged at 5000×g, followed by 0.2 µm filtration (10 kDa cut-off cellulose centrifugal filters; Sartorius-Stedim, Goettingen, Germany) and loaded onto the Concavalin-A (Con A) (GE Healthcare, Little Chalfont, UK) at 7 mg/mL resin. The Con-A eluate was loaded onto a Size-Exclusion-Chromatography (SEC) Sephacryl S-200 column (GE Healthcare). The SEC eluate was 0.2 µm filtered (Minisart syringe filter) (Sartorius-Stedim) and frozen at −70° C.

Table 4 lists some non-limiting materials and Table 5 lists some non-limiting equipment. Tables 6-8 provide more chromatographic details.

TABLE 4

Materials

| Name | Supplier | Cat. No |
|---|---|---|
| Con A Sepharose | GE Healthcare | 17-0440-01 |
| Sephacryl S-200 HR HiPrep XK16/60 | GE Healthcare | 17-1166-01 |
| Polyclonal anti-Human CTLA-4 antibody | RandD systems | AF-386-PB |
| Monoclonal anti-Human Fas Ligand antibody | RandD systems | MAB-126 |
| Alexa Fluor ™ 647 Monoclonal Antibody Labelling Kit | Invitrogen | A20186 |
| EZ-link Sulfo-NHS-LC-Biotin | Pierce | 21335 |
| Gyros Bioaffy CD microlaboratory 20 HC | Gyros | P0004424 |
| Microplate PCR Skirted, low profile | Gyros | P0000170 |
| Microplate Foil | Gyros | P0003313 |
| Rexxip CCS | Gyros | P0004824 |
| Rexxip F | Gyros | P0004825 |

TABLE 5

Equipment

| Name | Supplier | Inv. No. |
|---|---|---|
| Äkta Explorer | GE Healthcare | 300953 |
| Äkta Explorer | GE Healthcare | 300954 |
| Gyrolab Workstation | Gyros | D115038 |
| ND-1000 spectrophotometer | NanoDrop | D113731 |

TABLE 5-continued

Equipment

| Name | Supplier | Inv. No. |
|---|---|---|
| Centrifuge 5415R | Eppendorf | N/A |
| Thermomixer comfort | Eppendorf | D114581 |
| Cary 300 Bio | Varian | D105070 |

TABLE 6

Exemplary Resins and column dimensions

| Resin | Column diameter (cm) | Bed height (cm) | Column volume (mL) |
|---|---|---|---|
| Con A Sepharose, HiTrap | 1.6 | 2.5 | 5 |
| Sephacryl S-200 HR | 1.6 | 60 | 120 |

TABLE 7

Exemplary Con A chromatography method

| Step | Buffer | CV | Flow (mL/min) |
|---|---|---|---|
| Equilibration | 25 mM Tris, 0.5M NaCl, pH 7.4 | 4 | 1 |
| Load | Conc. clarified harvest, pH 7.1, conductivity 6.2 mS/cm | — | 1 |
| Wash | 25 mM Tris, 0.5M NaCl, pH 7.4 | 5 | 1 |
| Elution | 25 mM Tris, 0.2M α-D-Metylmannoside | 8 | 1 |
| Regeneration 1 | 25 mM Tris, 0.5M NaCl, pH 8.5 | 3 | 1 |
| Regeneration 2 | 25 mM NaCitrate, 0.5M NaCl, pH 4.5 | 3 | 1 |
| Re-eq | 25 mM Tris, 0.5M NaCl, pH 7.4 | 3 | 1 |
| Storage | 0.2M NaAc, 20% EtOH, 1 mM CaCl2, 1 mM MnCl2, 1 mM MgCl2 | 5 | 1 |

TABLE 8

Exemplary Sephacryl S-200 HR chromatography method

| Step | Buffer | CV | Flow (cm/h) |
|---|---|---|---|
| Equilibration | PBS, pH 7.3 | 1 | 30 |
| Load | Concentrated Con A Eluate | — | 30 |
| Elution | PBS, pH 7.3 | 1.2 | 30 |
| CIP | 0.5M NaOH | 0.25 | 10 |
| Re-equilibration | PBS, pH 7.3 | 2 | 30 |

Analytical SE-HPLC

Analytical size-exclusion (SE) was performed using a Dionex HPLC instrument (Pump P580, Auto sampler ASI-100/ASI-100T Injector, UV/VIS Detector UVD340U, Chromeleon 6.80 Software) with Tosoh Bioscience TSK-Gel G3000SWXL 7.8×300 mm column. Phosphate Buffered Saline (PBS) was used as the mobile phase and samples of <50 μg or 100 μg injected. Reference standards and 25% GFS (gastric fluid simulant) were run before and after the samples. The column was equilibrated by running with mobile phase (PBS) at flow rate 0.1 ml/min. The separation was performed using an isocratic separation method with a runtime of 20 min and a flow rate of 1 ml/min. The column oven was set at 25° C. and the sample holder at 8° C.

Iso Electric Focusing (IEF): CTLA4-FasL was separated on IEF gels (Novex, Life technologies, NY, USA), pH3-7 and pH3-10 according to the manufacturer's instructions.

His6-tagged protein: In-vitro experiments were performed with a His6 tagged version of CTLA4-FasL24. The activity of the tagged His6CTLA4-FasL was compared to that of the purified non-tagged CTLA4-FasL and found to be identical (not shown).

Cell lines. Liver adenocarcinoma SK-HEP-1 cell line, A498 Renal Carcinoma Cell line and Raji B cell lymphoma cell line were purchased from ATCC (Manassas, Va., USA). Other lymphatic cell lines were a kind gift from the Gene Therapy institute and Hepatology Unit, Hadassah Hebrew University Medical Center in Jerusalem, Israel. Attached cells were grown in DMEM (Gibco) supplemented with 10% FBS, 2 mM glutamine, 100 IU/mL penicillin and 100 μg/mL streptomycin, and were detached using Trypsin-EDTA solution. Suspended cells were grown in RPMI (Gibco) with the same additives. All cell lines were cultured at 37° C., 6% CO2.

Immuno-Histo-Chemistry

B cell lymphoma tissue microarray (TMA) (US Biomax; # LM801a, lymphoma tissue array with adjacent normal lymph node and spleen tissue as control, 80 cases) paraffin sections were deparaffinized in xylene (3×3') and rehydrated in graded alcohol (3×1' 100% ethanol; 3×1' 96% ethanol). Following 5' incubation in 3% $H_2O_2$ for endogenous peroxidase inactivation, slides were incubated in Citrate buffer (pH6; #005000; Invitrogen) and boiled in electric pressure cooker (DC2000; BioCare Medical) for antigen retrieval. Samples were blocked for 20' in CAS-BLOCK (#00-8120; Invitrogen) prior to overnight incubation with the primary antibodies at 4c in humidified box (see below table).

Following washing (3×2' in Super Sensitive wash buffer, #HK583-5K; BioGenex), samples were incubated for 30' in RT with the relevant secondary antibody (see below table). Diaminobenzidine (DAB; UltraVision Detection System, TA-125-HDX, Thermo scientific) was used as the chromogen according to manufacturer instructions, and 20" incubation in hematoxylin (MHS 16, SIGMA-Aldrich) was used as the nuclear counter-stain. Following dehydration steps (2' 80% ethanol, 2' 96% ethanol, 2' 100% ethanol, 2' xylene) and mounting (Histomount mounting solution, #0080-30; Invitrogen), Staining intensity was quantified using the Ariol SL50 automated robotic image analysis system, according to manufacturer instructions.

TABLE 9A primary antibody

| Primary Antibody | catalog No. | company | Final dilution |
|---|---|---|---|
| Rabbit anti human CD95 | SC-715 | Santa Cruz | 1:400 |
| Goat anti Human CD86 | AF-141-NA | RandD | 1:50 |

TABLE 9A-continued

| | primary antibody | | |
|---|---|---|---|
| Primary Antibody | catalog No. | company | Final dilution |
| Rabbit anti Human CD80 | Ab53003 | Abcam | 1:100 |

TABLE 9B

| | secondary antibody | |
|---|---|---|
| Secondary Antibody | company | dilution |
| Simple stain MAX PO (MULTI), universal immune-peroxidase polymer, anti mouse and rabbit | NICHIREI BIOSCIENCES INC. | Ready to use |
| Simple stain MAX PO (G), universal immune-peroxidase polymer, anti goat | NICHIREI BIOSCIENCES INC. | Ready to use |

FACS Analysis

Approximately $1\times10^6$ cells were washed with PBS in a FACS tube and re-suspended in 95 ul of staining buffer (1% BSA, 0.1% azide in PBS) and 5 ul of human Fc blocker (#422302; e-Bioscience), and incubate for 5' on ice. The appropriate antibody/isotype (see below Tables 10A and 10B) were added and incubated in the dark on ice for 30'. Cells were washed with PBS, re-suspended in 350 ul staining buffer, and filtered into a clean FACS tube via a 40 uM filter and kept in the dark on ice until analyzed by a BD™ LSR II Flow Cytometer, according to the manufacturer instructions; 20,000 events per sample were counted. Data were analyzed using CellQuest software (Becton Dickinson).

TABLE 10A

| | antibody list | |
|---|---|---|
| Antibody | catalog No. | company |
| PE-anti hCD95 | 12-0959-73 | eBioscience |
| APC-anti hCD86 | 555660 | BD |
| FITC-anti hCD80 | 557226 | BD |

TABLE 10B

| | isotype antibody list | |
|---|---|---|
| Isotype Antibody | catalog No. | company |
| PE-mouse IgG1 kappa | 12-4714-42 | eBioscience |
| APC-mouse IgG1 kappa | 17-4714-42 | eBioscience |
| FITC-mouse IgG1 kappa | 11-4719-73 | eBioscience |

CTLA4-FasL Quantification by Gyrolab

To efficiently quantify CTLA4-FasL, a Gyrolab platform immunoassay (Gyrolab Workstation, Gyros) was developed. This immunoassay utilizes capture and detection by two different antibodies specific to different regions of CTLA4-FasL. The assayed sample was transferred by centrifugal force through Streptavidin beads coated with anti-CTLA4 antibodies, that were packed in minute columns (15 nL) and quantification was performed by the detection of an anti-FasL antibody that was bound to the product in the column, by laser induced fluorescence.

An anti-Human CTLA-4 polyclonal goat antibody (AF-386PB, RandD systems) was selected as capture antibody. The polyclonal antibody was generated using recombinant human CTLA4 Ala37-Phe162 (Accession # Q6GR94) expressed in S. frugiperda insect ovarian cell line Sf 21. The polyclonal antibody was biotinylated using EZ-link Sulfo-NHS-LC-Biotin as described in the instructions supplied with the kit. The biotinylated material was purified by a size-exclusion spin column and the material kept in PBS.

An anti-Human Fas Ligand monoclonal mouse IgG2B antibody (MAB-126, RandD systems) was selected as detection antibody. The monoclonal antibody was generated using recombinant human Fas Ligand/TNFSF6, Pro134-Leu281 (Accession # P48023) expressed in Chinese hamster ovary cell line CHO. The monoclonal antibody was Alexa labeled using the Alexa Fluor™ 647 Monoclonal Antibody Labelling Kit as described in the instructions supplied with the kit. The labeled material was purified by using a size-exclusion spin column included in the kit. The Alexa labeling was measured to be 6.9 Alexa/Ab and the material diluted to 1 µM with 1% BSA in PBS and kept in the freezer.

CTLA4-FasL sample was transferred by centrifugal force through Streptavidin beads coated with anti-CTLA4 antibodies, that were packed in minute columns (15 nL) and quantification was performed by the detection of an anti-FasL antibodies that were bound to the CTLA4-FasL in the column, by laser induced fluorescence.

In-Vitro Activity Bioassay

For in vitro examination of the CTLA4-FasL cytotoxic effect on different human cell lines, 32,000 cells per well (suspended cultures) or 8000 cells per well (attached cells) in 50 ul of complete RPMI (suspended cultures) or DMEM (attached cells) medium without Phenol Red, were seeded in triplicates, in a flat 96-wells plate (Nunc or similar), and 50 ul of CTLA-4•FasL (or $his_6$CTLA-4•FasL) dilutions (in growth media; 3000ng/ml-0.1 ng/ml, triplicates), or dilution media as negative control were added. Calibration curve wells contained serial dilution from 64,000 to 2000 cells per well for suspended cultures or 16,000 to-2000 cells for attached cells in triplicates. Plates were incubated for 24 hours at 37 c in 5% CO2 humidified incubator. Cell viability was quantified by a MTS kit (Promega, CellTiter 96® Aqueous Non-Radioactive Cell Proliferation Assay) according to manufacturer instructions.

Mouse Disease Models

Xenograft lymphoma model: Athymic-NUDE female mice (Harlan, Israel), 4-6 weeks of age, were maintained under defined flora conditions at the Hebrew University Pathogen-Free Animal Facility. All experiments were approved by the Animal Care Committee of the Hebrew University. The JY cells used in this study were harvested from subcutaneous JY xenograft tumor, and expanded in culture. Mice were irradiated (300R), and two days later JY cells in exponential growth were harvested, washed with PBS, and injected subcutaneously (7-10×106/mouse) into the right flanks of mice. When tumors were palpable, at day 5, treatment was started. Mice were treated for 4 days with two 100 micro-liter subcutaneous injections per day of CTLA4-FasL or the vehicle buffer (PBS). Tumor size was measured by a micro caliber and volume was calculated by the equation: (w 2*length/2). Mice bearing tumor of >1000 mm3 or necrotic tumors were sacrificed. In some experiments, and to further assess CTLA4-FasL effect on JYderived tumors, mice were sacrificed one hour post the 1st injection, at the 4th injection day (20 micro-gram CTLA4-FasL per day). SC tumors were removed and fixated for in 4% formaldehyde, routinely processed, and embedded in paraffin. Transverse sections (5 µm) were stained with hematoxylin and eosin (HandE).

A mouse/mouse model for lymphatic cancer: Balb/c mice were injected intravenously with $1×10^6$ Bcl-1 cells in 200 ul PBS (murine B cell leukemia splenocytes; Ref: Slavin S, Nature, v 272, p 624, 1978). From the next day, mice were treated for 3.5 days with two 100 ul subcutaneous injections per day of CTLA4-FasL or the vehicle buffer (PBS). Disease parameters were monitored by measuring mouse weight, spleen weight and blood counts.

Pharmacokinetics: For analysis of pharmacokinetics, CTLA4-FasL at different doses was subcutaneously injected to mice at a total volume of 150 microliter per mouse. Mice were sacrificed at various time points post injection. Blood was collected in heparin, kept on ice, centrifuged at 1000 g (~3000 rpm) for 10', plasma was kept at −70 c. CTLA4-FasL was quantified by LEGEND MAX™ Human Soluble CTLA-4 ELISA kit (Biolegend #437407), according to the manufacturer instructions.

Results and Discussion—Purification

As shown in the previous results, CTLA4-FasL was found to be most stable in a form which is described herein as either a homo-hexamer or a multimer of approximately 250 kD. Without wishing to be limited by a single hypothesis, it is believed that this highly stable form of CTLA4-FasL is in fact a homo-hexamer in solution, based upon the data; however, it should be noted that the data definitively supports the concept that the protein is a multimer of approximately 250 kD molecular weight.

Such results are surprising, because previous authors did not realize that CTLA4-FasL would actually preferentially form such a stable homo-hexamer upon secretion to cell media, and that this preferential form would maintain its configuration during purification in solution. Furthermore, previous authors did not realize that this form would be a highly stable form of CTLA4-FasL in solution, and that purification peaks which preferentially contain the homo-hexamer form would contain the majority of in vitro functional activity for the CTL4-FasL fusion protein.

As noted previously, in order to produce the fusion protein CTLA4-FasL, a gene coding for the human sequence of CTLA4-FasL, linked to the human Urokinase signal peptide, was cloned into an expression vector (FIG. 1) and transfected to CHO-S cells. An isolated production clone expressed and secreted CTLA4-FasL to the growth medium.

Figure 2:
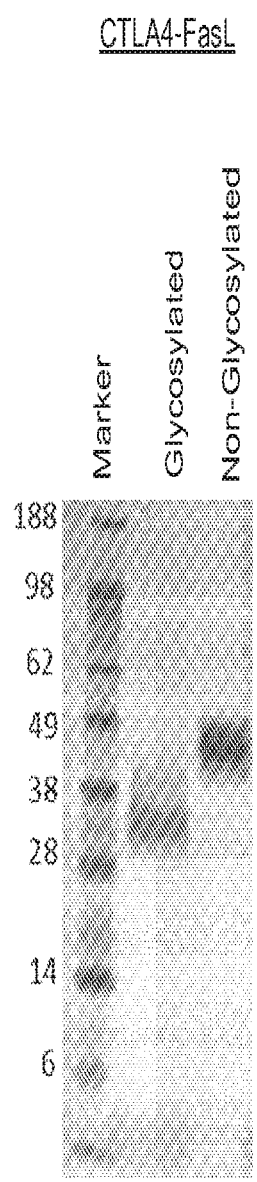

Western blot analysis of the production media, using monoclonal antibodies to both human CTLA-4 and FasL (not shown), showed a band that specifically reacted with both anti-CTLA4 and anti-FasL. Although the predicted molecular weight of CTLA4-FasL is approximately 31 kD, the CTL4-FasL fusion protein migrated in a reduced SDS-PAGE as a protein of approximately 43 kD. The difference between the calculated and observed molecular weight of CTLA4-FasL was not investigated in the past and by treating production media samples with the "Peptide N-Glycosidase F" enzyme, that removes N-glycan chains from the protein followed by Western blot analysis, it was found that treatment with the enzyme caused a shift in molecular weight from ~45 kDa to ~33 kDa, which appears to suggest that the apparent difference in MW is due to protein glycosylation (FIG. 2).

Initial attempts to purify this protein were not successful. As shown in Table 11 (included within the figures), attempts to purify the protein from host-cell proteins, using art-known chromatographic methods, such as cation-exchange, anion-exchange and hydrophobic-interactions chromatography for example, which had proved reliable and successful for other proteins in the past, failed to be successful for purifying CTLA4-FasL at its expected molecular weight and PI.

Figure 3A:
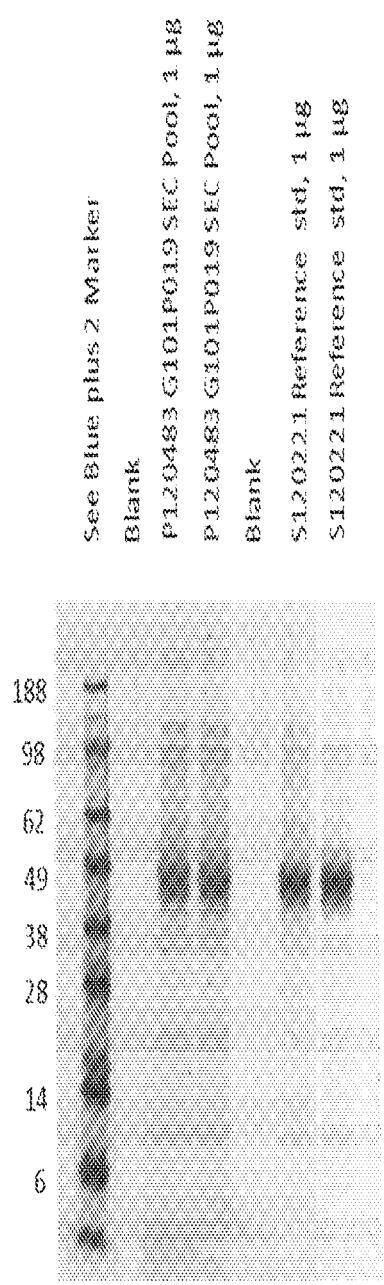
Figure 3B:
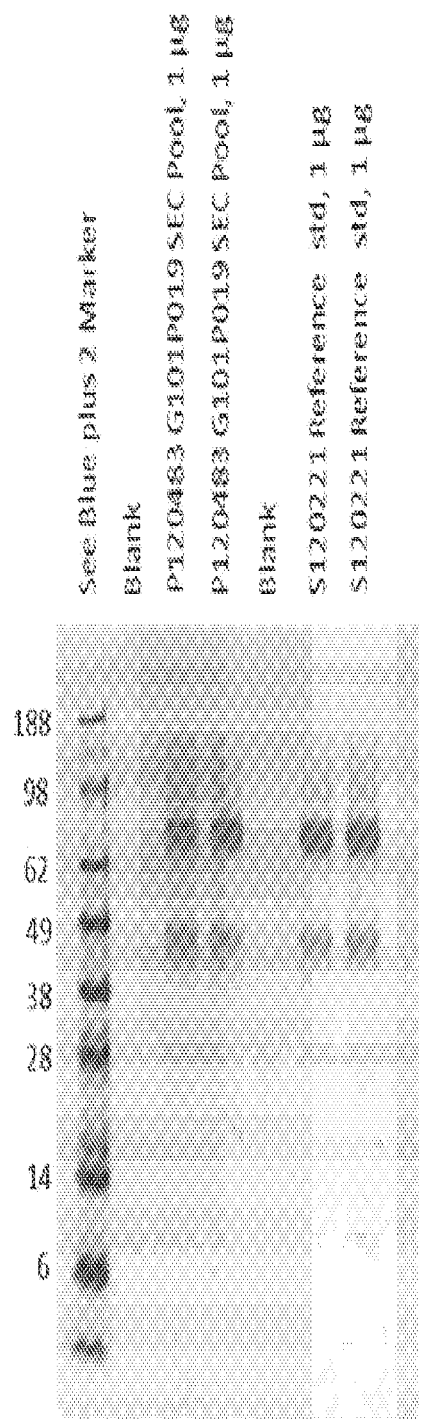

Utilizing the glycosylation of CTLA4-FasL, a preliminary purification process was developed, in which Concanavalin-A (Con-A) chromatography was used as the main capture step, followed by size-exclusion chromatography (SEC), yielding CTLA4-FasL at over 90% purity as measured by SDS-PAGE (FIG. 3).

Figure 4A:
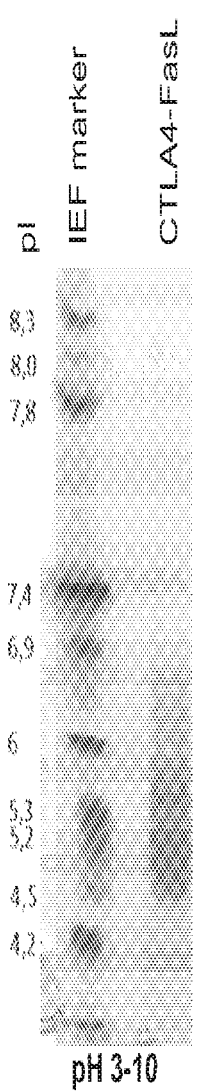
Figure 4B:
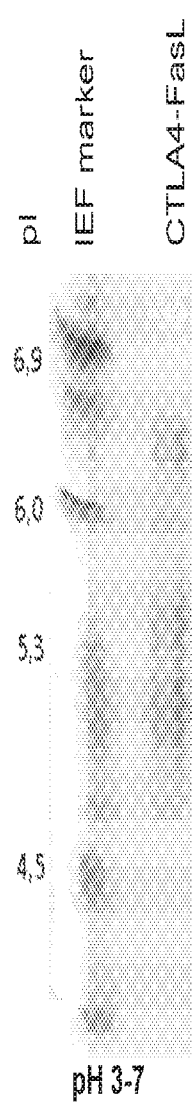

The theoretical iso-electric point (pI) of CTLA4-FasL is 6.59. To measure the actual protein pI, the purified CTLA4-FasL was analyzed by Iso-Electric-Focusing. Surprisingly, the actual pI of the protein is approximately 4.5, significantly different from the theoretical one. FIG. 4A shows iso-electric focusing at pH 3-10, while FIG. 4B shows iso-electric focusing at pH 3-7.

The in-vitro killing activity of the purified CTLA4-FasL was measured on both malignant and non-malignant human cell-lines and, as can be seen in FIG. 5, the protein has almost no effect on non-malignant cell-lines, while significant killing effect was shown on specific cancer cells, with an unanticipated enhanced effect on lymphatic cancer lines (see for example U.S. patent application Ser. No. 13/824,423, filed on Mar. 18 2013, having at least one common inventor and owned in common with the present application). Some of the experiments summarized in FIG. 5 were performed with an early tagged version of CTLA4-FasL (Dranitzki Elhalel et al, International Immunology, vol 19, 2007, pp 355-363; and Orbach et al, American J of Pathology, vol 177, 2010, pp 3159-3168). A further discussion of the specificity of anti-cancer activity by CTLA4-FasL is provided below.

Figure 6:
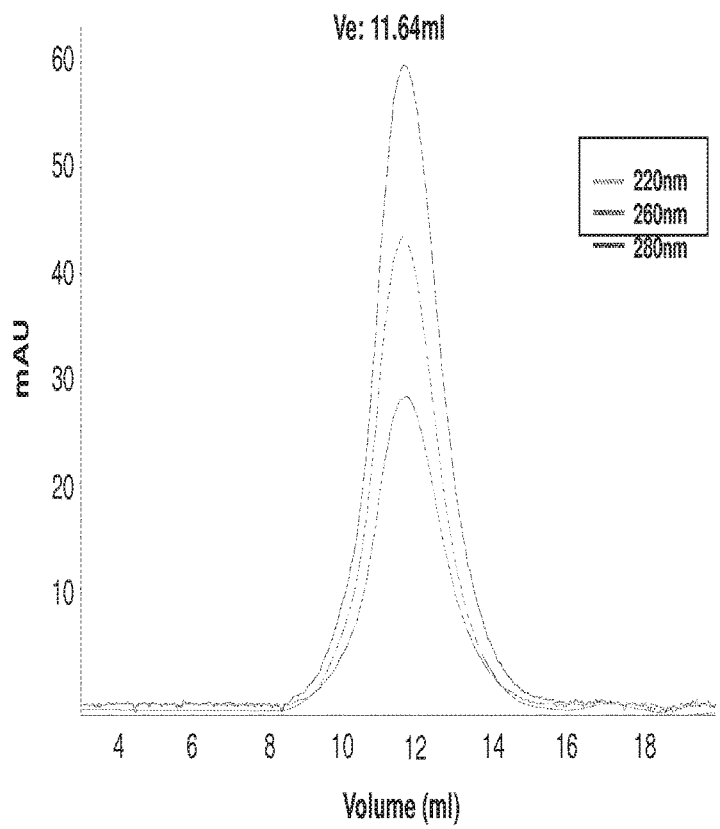

To further study the actual structure of CTLA4-FasL, purified CTLA4-FasL was initially analyzed by gel-filtration chromatography (specifically by running purified CTLA4-FasL (after ConA/SEC chromatography) on a Seperose-12 column (GE Healthcare, 100×1.6 cm ~200 ml). As can be seen in FIG. 6 the protein peak of CTLA4-FasL fractionates at approximately 87 ml, similar to that of Catalase, with MW of 232 kD; thus, these results indicate that most of the CTLA4-FasL protein migrates as a peak of approximately 250 kD.

Figures 1, 7A:
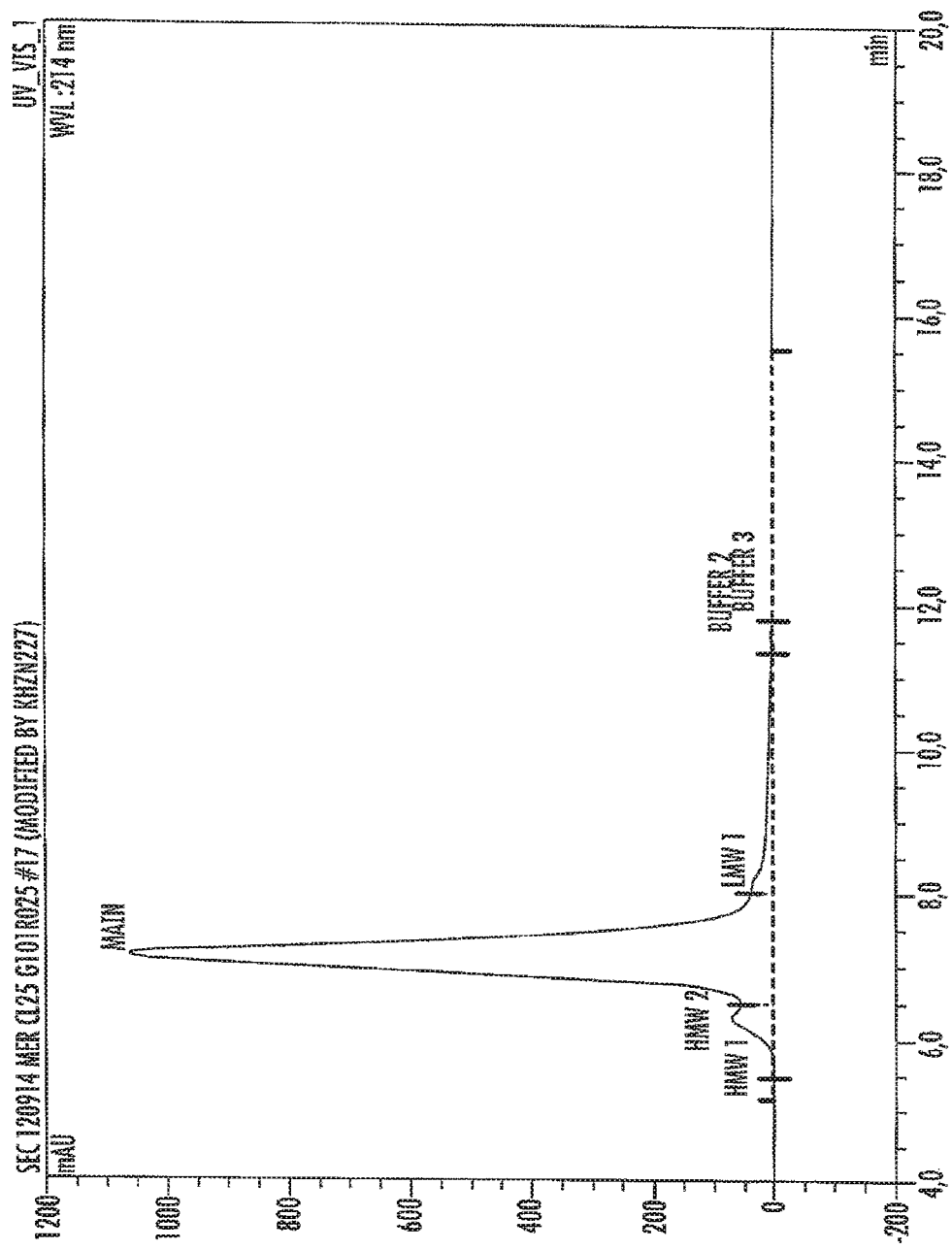
Figures 2, 7A:
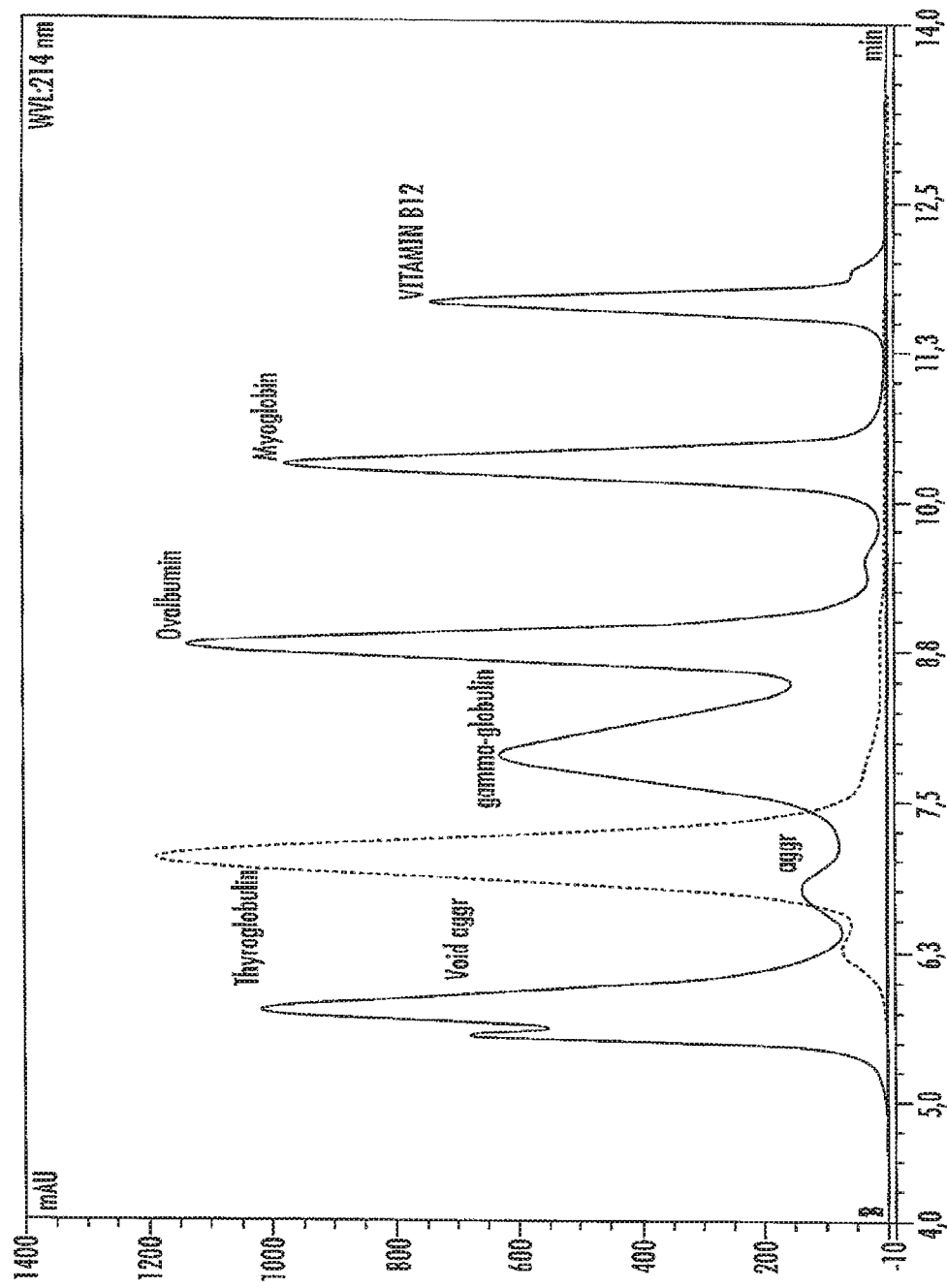
Figure 7B:
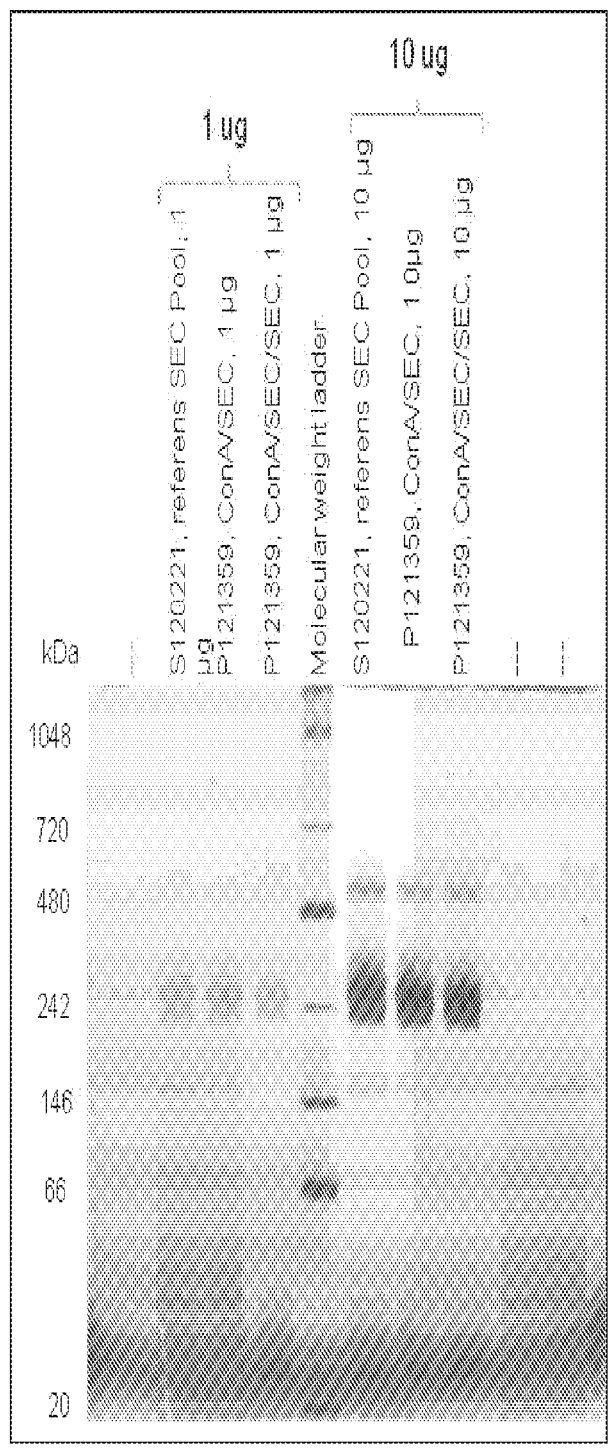

Since this observed product size of about 250 kD was significantly larger than the predicted homo-trimer (e.g., ~130 kD) suggested by others, analytical Size-Exclusion High-performance Liquid Chromatography (SE-HPLC) and native-PAGE were used to study the actual product size at higher resolution, as shown in FIG. 7A. Surprisingly, it was found that roughly 90% of the CTL4-FasL fusion protein migrates as a peak of approximately 250 kD in SE-HPLC, which is consistent with the size of a homo-hexamer, while the rest of the protein (~10%) was found mostly as a higher-molecular-weight (HMW) peak. When the samples were analyzed by a second high-resolution technique, namely Native-PAGE, an identical pattern was found; with most of the protein migrating as a 250 kD band and a minor band of approximately twice that size, i.e., 500 kD (FIG. 7B), which is consistent with a dodecamer form as described herein.

Figure 8A:
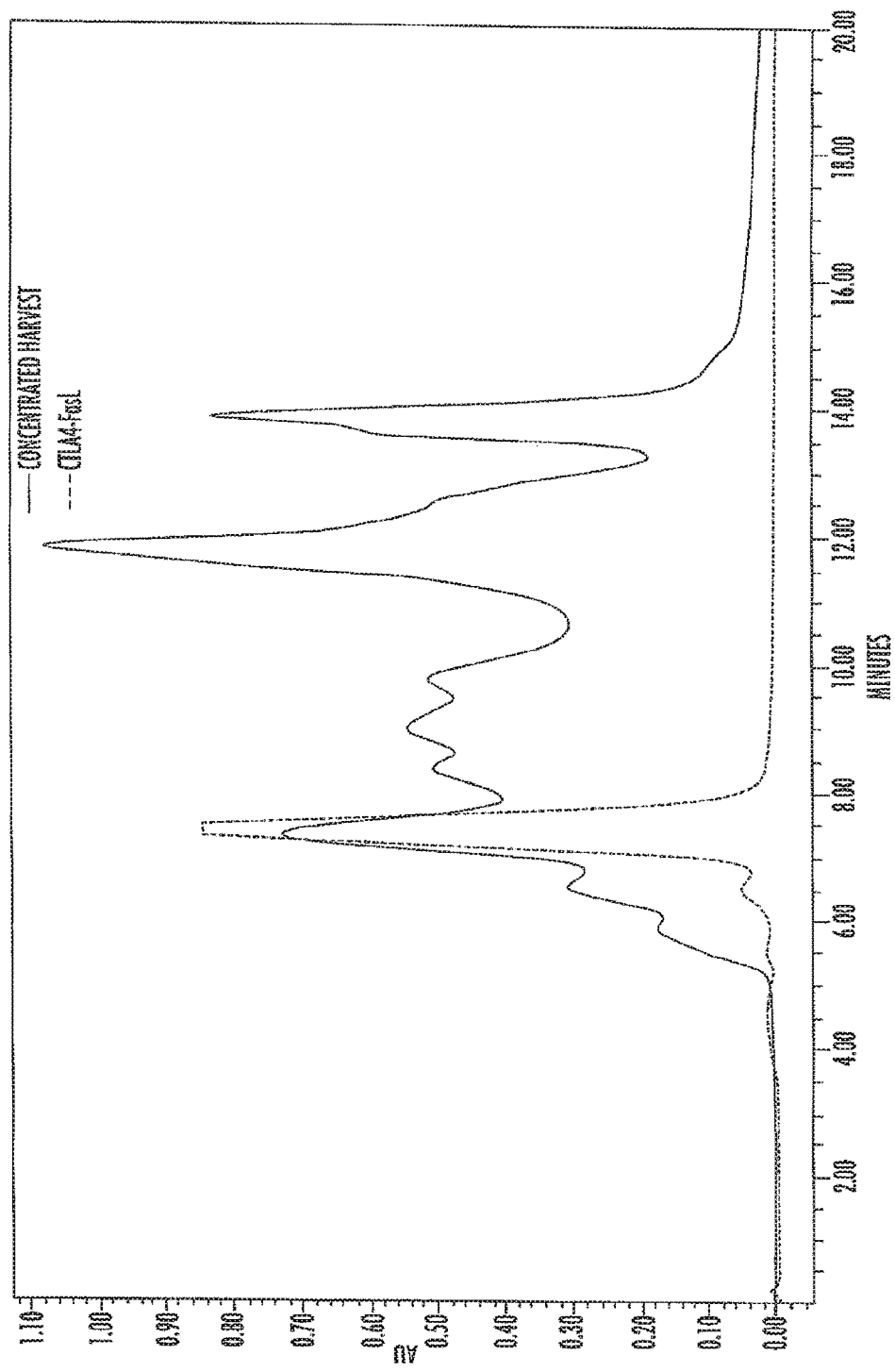
Figure 8B:
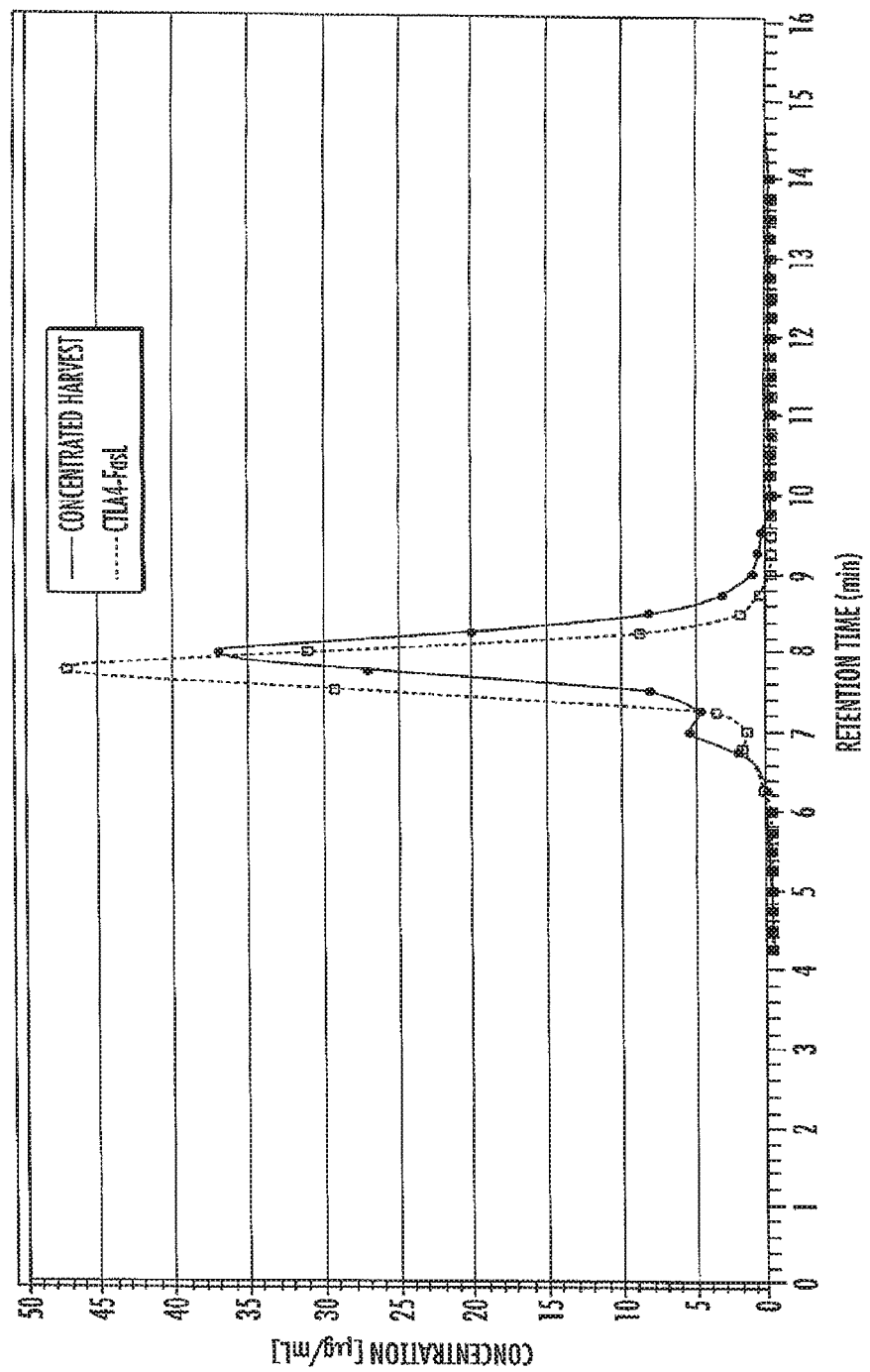

To test if the CTLA4-FasL homo-hexamer structure is formed only at high-concentrations of pure preparations of the protein, a similar SE-HPLC analysis was performed on harvested production media, before any purification was carried out, and the amount of CTLA4-FasL in the SE-HPLC fractions was quantified by CTLA4-FasL Gyrolab analysis. As can be seen in FIG. 8, most of the CTLA4-FasL in the harvest media corresponds to a large SE-HPLC peak with retention-time identical to that of the CTLA4-FasL homo-hexamer, indicating that the vast majority of the CTLA4-FasL fusion protein is in a homo-hexamer structure already at the harvest media, before any purification took place; however even before purification, as can be seen, about 5% of the CTL4-FasL fusion protein is in the dodecamer form, as determined by retention time.

The natural stochiometry of CTLA4-FasL is of great functional significance to its activity since the optimal functionality of FasL-related apoptosis is predicted to be linked to the formation of two FasL trimers, namely a homo-hexamer, which activates two FasR trimers at the target cell membrane (Holler et-al, MOLECULAR AND CELLULAR BIOLOGY, Feb. 2003, p. 1428-1440. Eisele et-al, Neuro-Oncology 13(2):155-164, 2011). Thus, a homo-hexamer of CTLA4-FasL is predicted to be more competent than other oligomeric forms. To test that theory, a preparative SEC of CTLA4-FasL was performed and the bioactivity of fractions representing the homo-hexamer were compared to fractions representing lower and larger CTLA4-FasL oligomer forms. Concentrated clarified harvest was partially purified by Con-A chromatography followed by SEC fractionation on a Superdex 200 column. The SEC fractions were then analyzed by SEC-HPLC and the relative percentage of different product types [250 kD product (Main Peak), Low Molecular Weight (LMW) and High Molecular Weight (HMW, presumably the dodecamer form)] are indicated in Table 12.

TABLE 12

SEC-HPLC analysis results of the different SEC fractions

| Sample | SE-HPLC (%) | | |
|---|---|---|---|
| | HMW | Main | LMW |
| SEC run 1 A12 | 22.5 | 71.7 | 5.9 |
| SEC run 1 B1 | 9.9 | 85.3 | 4.8 |
| SEC run 1 B2 | 4.4 | 91.6 | 4.1 |
| SEC run 1 B3 | 3.1 | 93.1 | 3.8 |
| SEC run 1 B4 | 3.2 | 92.3 | 4.5 |
| SEC run 1 B5 | 2.8 | 90.7 | 6.4 |
| SEC run 1 B6 | 2.2 | 86.8 | 11.0 |
| SEC run 1 B7 | 1.5 | 81.4 | 17.1 |
| SEC run 2 A7 | 89.0 | 5.7 | 5.4 |
| SEC run 2 B10 | 0.3 | 2.3 | 97.5 |
| SEC run 2 C5 | 0.3 | 0.7 | 99.0 |
| SEC run 3 A3 | 2.7 | 96.2 | 1.1 |
| SEC run 3 A5 | 1.3 | 98.0 | 0.7 |
| SEC run 3 A7 | 1.5 | 97.1 | 1.4 |
| SEC run 3 A9 | 1.4 | 96.1 | 2.5 |
| SEC run 3 A11 | 1.1 | 92.1 | 6.8 |
| SEC run 3 A12 | 0.9 | 87.7 | 11.4 |

Figure 9A:
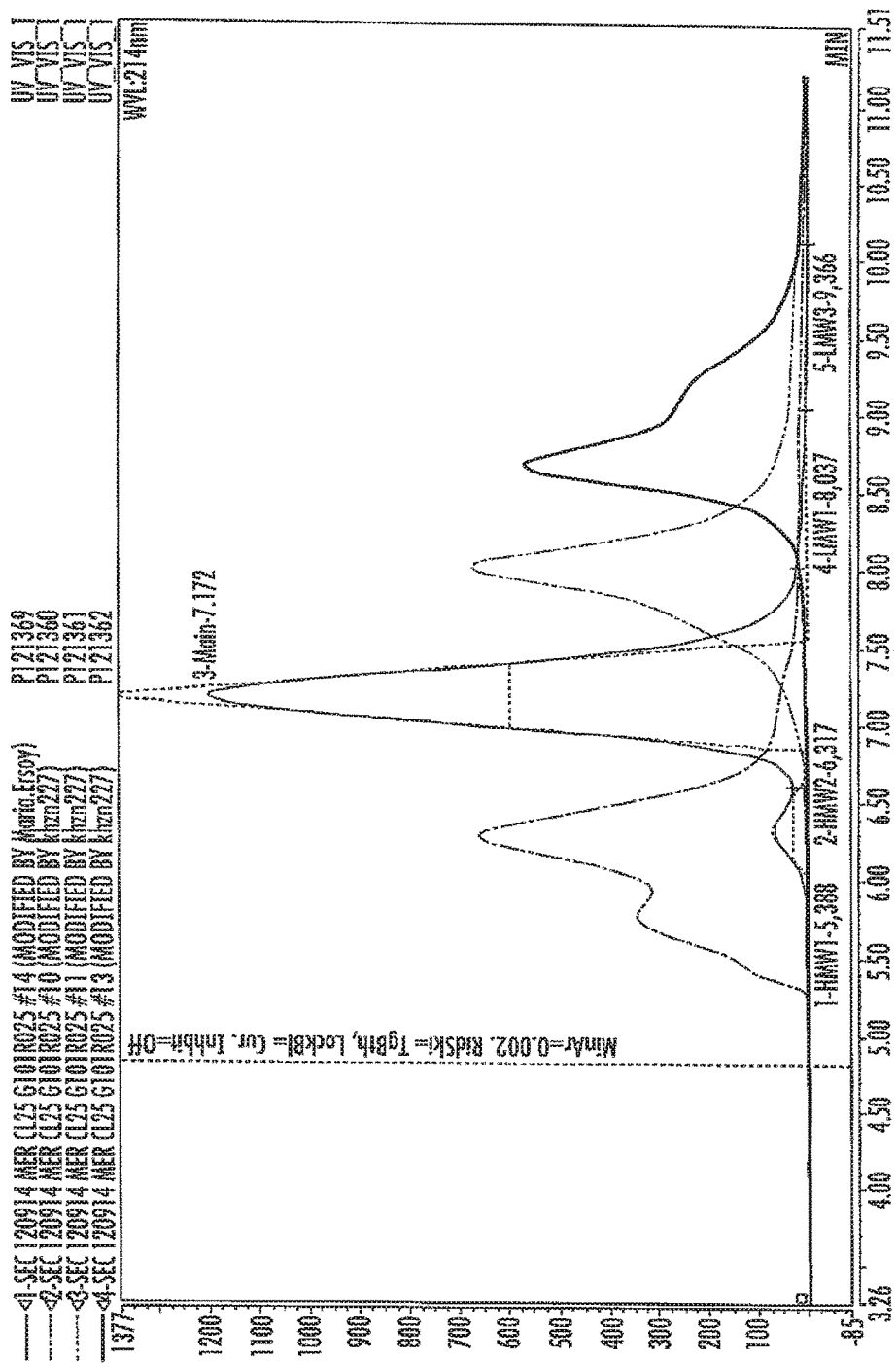

Specific fractions were then pooled to represent four different product types (250 kD, HMW (dodecamer), LMW1, LMW2) and an overlay of the pools can be seen in FIG. 9A. The bioactivity of the four pools were studied and, as can be seen in FIG. 9B, comparable protein quantities of the fractions do show differences in bioactivity, with the fraction of the homo-hexamer showing the highest killing activity. Interestingly, the fractions containing the dodecamer also show high in-vitro activity.

Figure 12A:
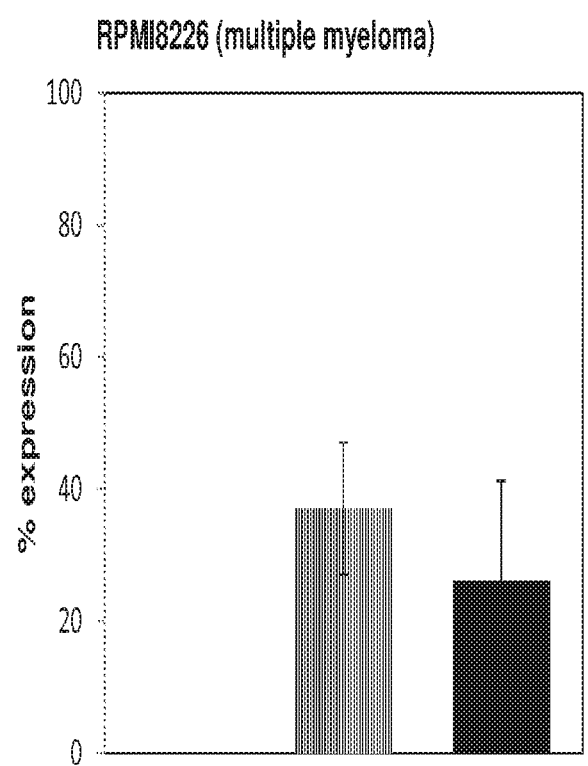
Figure 12B:
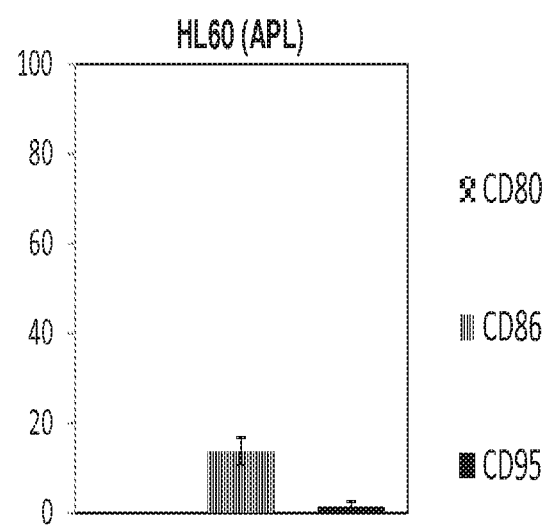
Figure 12C:
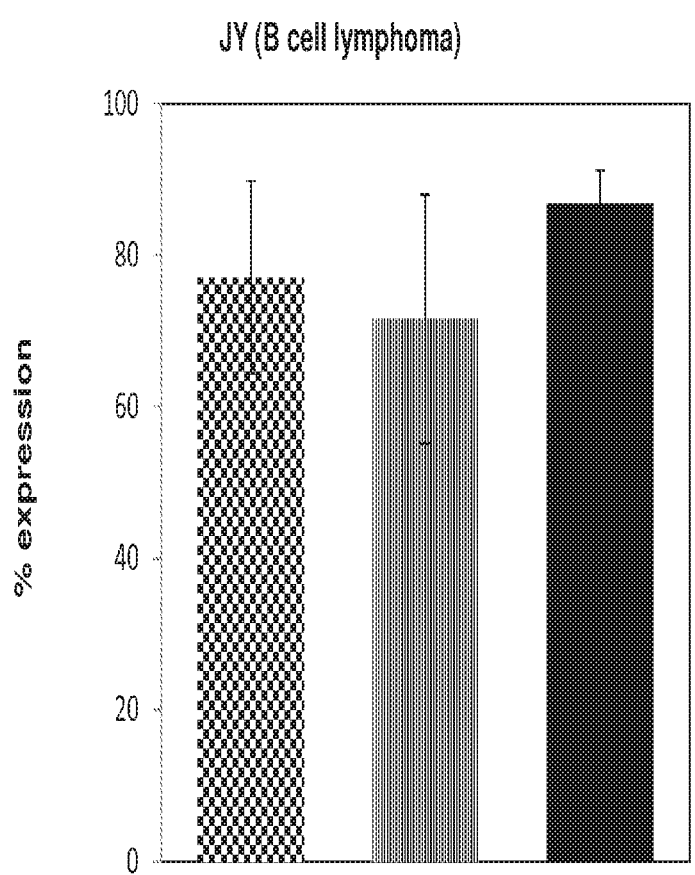
Figure 12D:
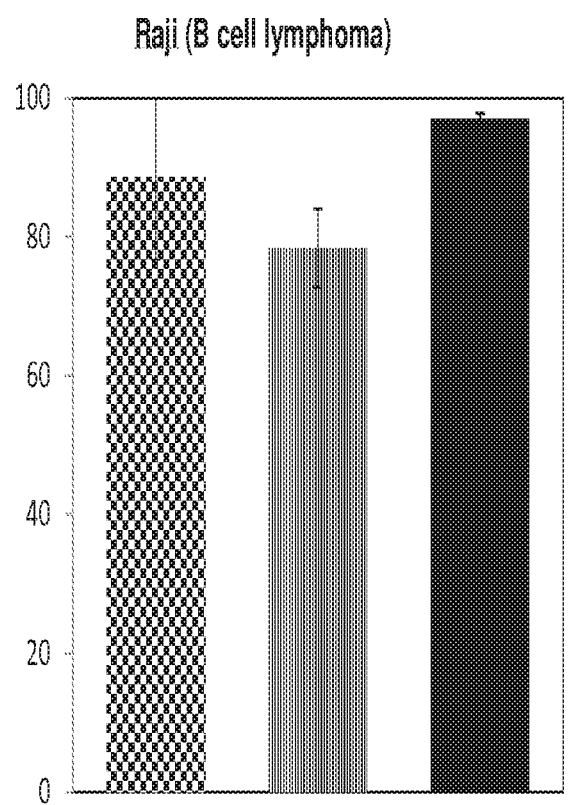
Figure 12E:
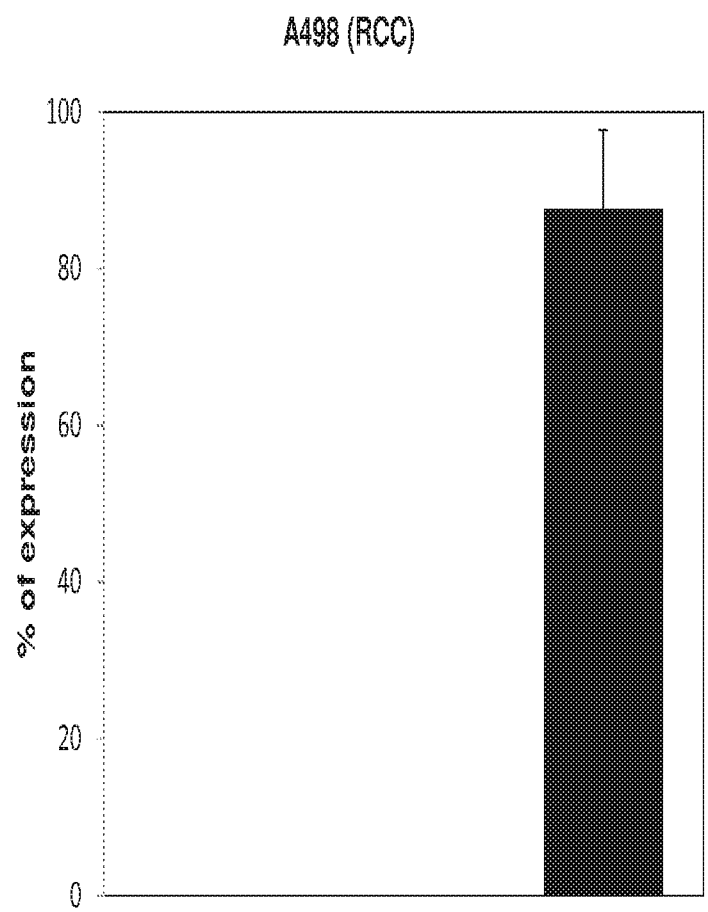
Figure 12F:
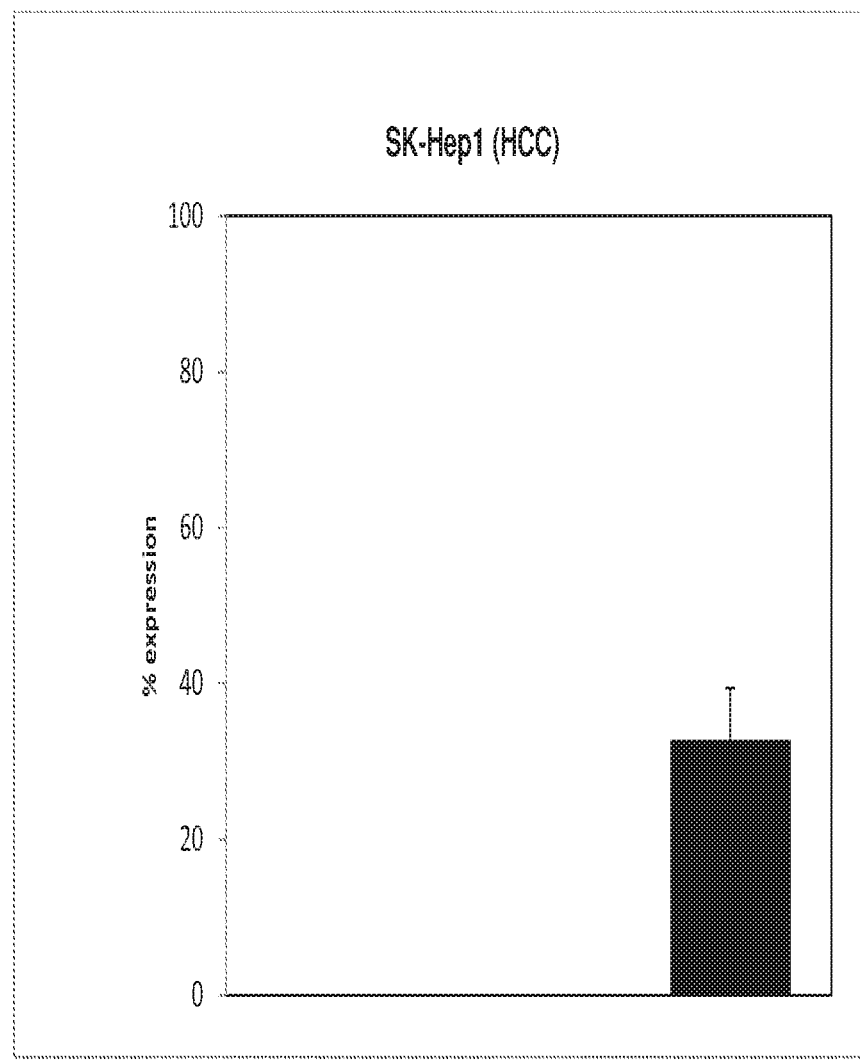

To assess the natural stability of the CTLA4-FasL homo-hexamer, purified CTLA4-FasL was subjected to different chemical and physical conditions, and their effects were studied by SE-HPLC analysis to determine whether the homo-hexamer form was maintained:

Freeze/thaw cycles: Purified CTLA4-FasL went through repeated freeze/thaw (FT) cycles. 1×FT, 3×FT and 5×FT were performed when in each cycle samples were moved from −80° C. to RT until the samples were completely thawed. As can be seen in FIG. 10, although a minor decrease in hexamer peak and increase in HMW (dodecamer) peak was observed, repeated freeze/thaw cycles had little effect on homo-hexamer stability.

Reduction and oxidation: Since disulfide-bonds between CTLA-4 domains are thought to play a major role in the formation of the CTLA4-FasL homo-hexamer, the effects of reduction and oxidation on hexamer stability were assessed via incubation (2-8° C. for ~24 h) in increasing amounts of glutathione (GSH; 2.5, 5, 7.5 and 10 mM) or copper sulfate ($CuSO4$; 5, 50, 100 and 200 mM). Surprisingly, both reduction and oxidation leads to a dramatic shift from CTLA4-FasL homo-hexamer to dodocamers with no observed formation of lower MW oligomers (FIG. 11).

An additional detailed purification process was performed to determine yield but also the ratio of CTLA4-FasL homo-hexamer to dodocamers. This process was performed as follows. The medium harvest to be purified (including CTLA4-FasL with other proteins) was applied to a 300 kDa UF/DF retentate membrane system. UF stands for ultrafiltration while DF stands for diafiltration. In this case, the membrane pore size had a MW (molecular weight) cut-off of 300 kDa. Proteins and other molecules that have a lower MW than 300 kDa pass through the membrane and are collected as filtrate. Molecules with a MW greater than 300 kDa are retained by the membrane and collected as retentate. The process enables concentration and buffer exchange. Even though CTLA4-FasL homo-hexamer has 250kDa MW, it is retained by the membrane and collected as retentate.

Next, the material was applied to at least a phenyl sepharose column (additional columns could also be used at this point). Viral inactivation may also optionally be performed after application of the material to one or more columns and was in fact performed in this example. Optionally, a 30 kDa UF/DF retentate membrane system could be used and was in fact used in this example. After that a Superdex column was used for chromatography, which included the Superdex material from GE Healthcare Life Sciences (made from dextran covalently attached to cross-linked agarose). Again one or more other columns could also optionally be applied.

The resultant fractions after application to the Superdex column were analyzed as shown in FIG. 23 and two fractions clearly appeared; the second fraction contained the homo-hexamer form of CTLA4-FasL, while the first fraction contained the higher molecular weight dodecamer form. As can be seen, large amounts of the dodecamer form are present during purification; even if not quite 50% of the total, still a significant amount of dodecamer form fusion protein is present.

Results and Discussion—Anti-Cancer Activity

As previously described, the in-vitro killing activity of the purified CTLA4-FasL was measured on both malignant and non-malignant human cell-lines and, as can be seen in FIG. 5, the protein has almost no effect on non-malignant cell-lines, while significant killing effect was shown on specific cancer cells, with an unanticipated enhanced effect on lymphatic cancer lines.

The exceptional cancer killing activity of CTLA4-FasL, observed on lymphatic cancer cells (e.g., EC50 of 0.02 nM) as compared to other cell types, might be related to high expression of B7 receptors on these cells. To investigate possible correlation between drug activity and receptor expression, FACS was used to quantify the expression of the three target receptors of CTLA4-FasL, namely CD80 (B7.1), CD86 (B7.2) and CD95 (FasR), on the different human cancer cell lines. Results shown in FIGS. 12A-F. As can be seen in FIG. 12B, the APL HL60 Human Promyelocytic Leukemia cell line, found to be CTLA4-FasL resistant by the bioassay, expresses very low levels of surface CD86 and undetectable CD80 and FasR levels. Similarly, the multiple myeloma cell line, RPMI8226, also found to be CTLA4-FasL resistant, expresses only low surface levels of FasR and CD86, with no CD80 (FIG. 12A). In contrast, the JY and Raji B cell lymphoma cell lines, shown to be highly sensitive to CTLA4-FasL, express high levels of CD80, CD86 and CD95 (FIGS. 12C and 12D, respectively). Cell lines expressing only FasR (A498 and SK-HEP1, FIGS. 12E and 12F, respectively) were moderately sensitive to CTLA4-FasL. These findings suggest that malignant cells expressing both receptors are highly sensitive to CTLA4-FasL, cells expressing just FasR, are moderately sensitive, while cells that express none of the receptors are resistant to the CTL4-FasL fusion protein's apoptotic effect.

Figures 1, 13A:
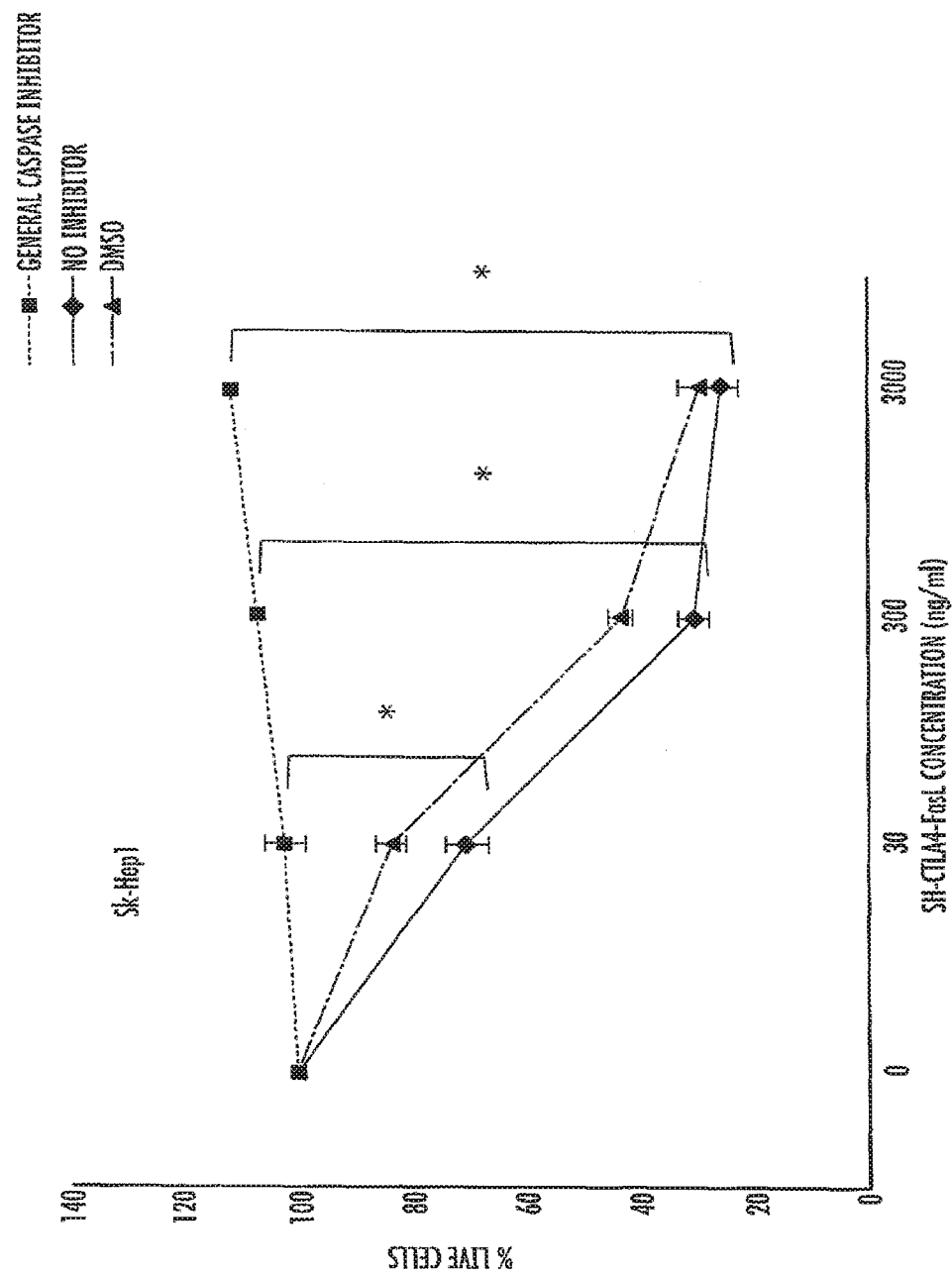
Figures 2, 13A:
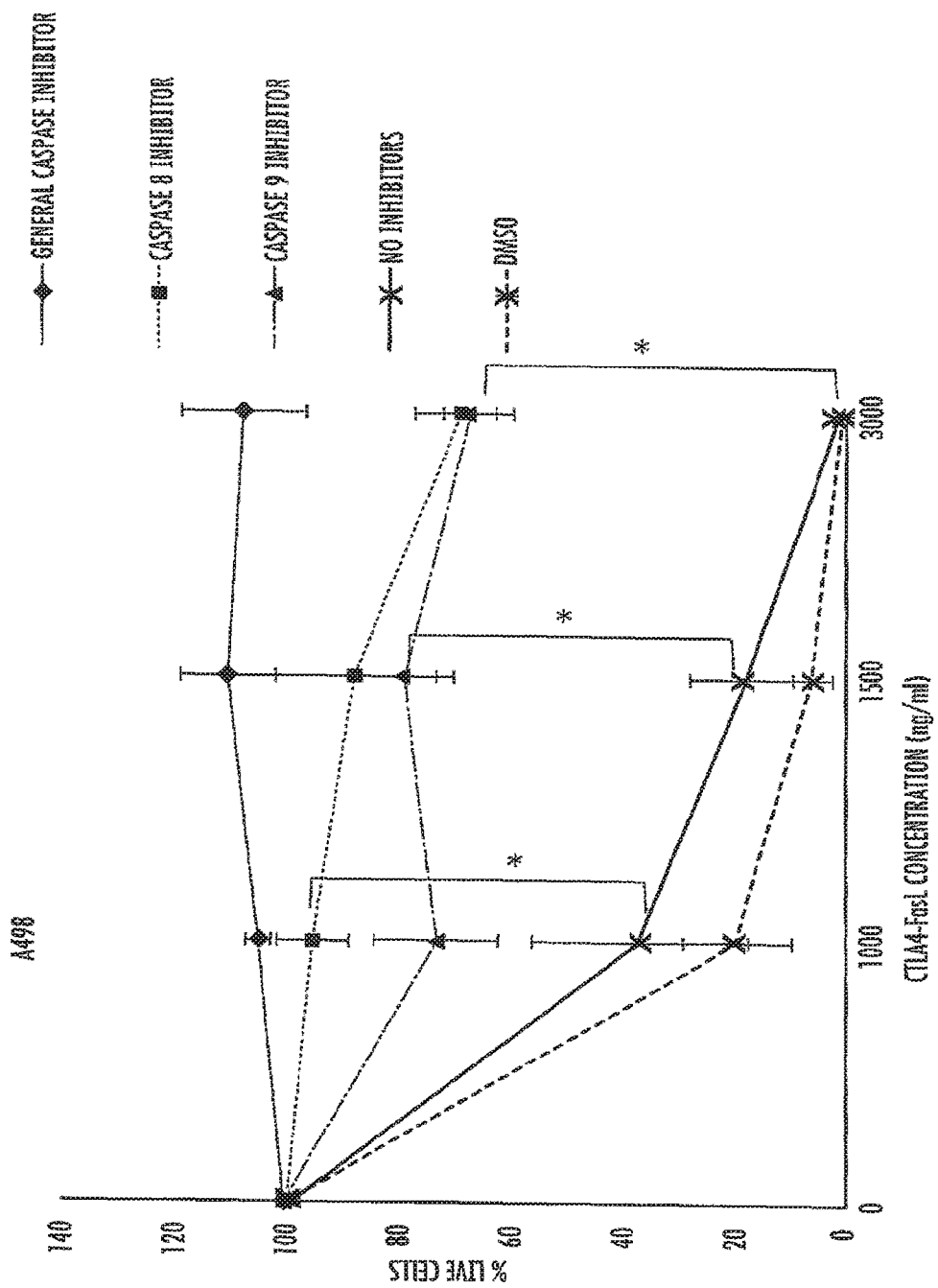

CTLA4-FasL Killing Activity is Apoptosis-Based and is Superior to its Two Subunits or Their Combination It was previously shown that his6-CTLA4-FasL induces efficient apoptosis of lymphatic cancer cells by utilizing a dual signaling pathway that includes Fas-mediated apoptosis of CD95 expressing cells, coupled to the abrogation of cFLIP expression in B7 expressing cells (Orbach A, Rachmilewitz J, Shani N, Isenberg Y, Parnas M, Huang J H, Tykocinski M L, Dranitzki-Elhalel M., Am J Pathol. 2010 December; 177(6):3159-68). It was also previously shown that CTLA4-FasL inhibitory effect on T lymphocyte activation is mediated by apoptosis induction, through the cascade of caspases (Orbach A, Rachmilewitz J, Parnas M, Huang J H, Tykocinski M L, Dranitzki-Elhalel M., J Immunol. 2007 Dec. 1; 179(11):7287-94). To further investigate CTLA4-FasL mode-of-action in cancer cell line, an experiment was performed to determine whether CTLA4-FasL killing effect can be abrogated by the pan-caspase inhibitor, Z-VAD, caspase 8 inhibitor (Z-IETD-FMK) and caspase 9 inhibitor (Z-LEHD-FMK) on malignant cell lines positive for FasR only. As can be seen in FIGS. 13A-1 and 13A-2, the pan caspase-inhibitor resulted in full inhibition of CTLA4-FasL killing effect of the Sk-Hep1 and A498 cell lines. The inhibitors of caspase 8 and 9 resulted in partial inhibition, supporting the assumption that CTLA4-FasL activity is mediated by both the intrinsic and the extrinsic apoptotic pathways, without wishing to be limited by a single hypothesis. Caspase 8 inhibitor was more potent than the caspase 9 inhibitor.

Figure 13B:
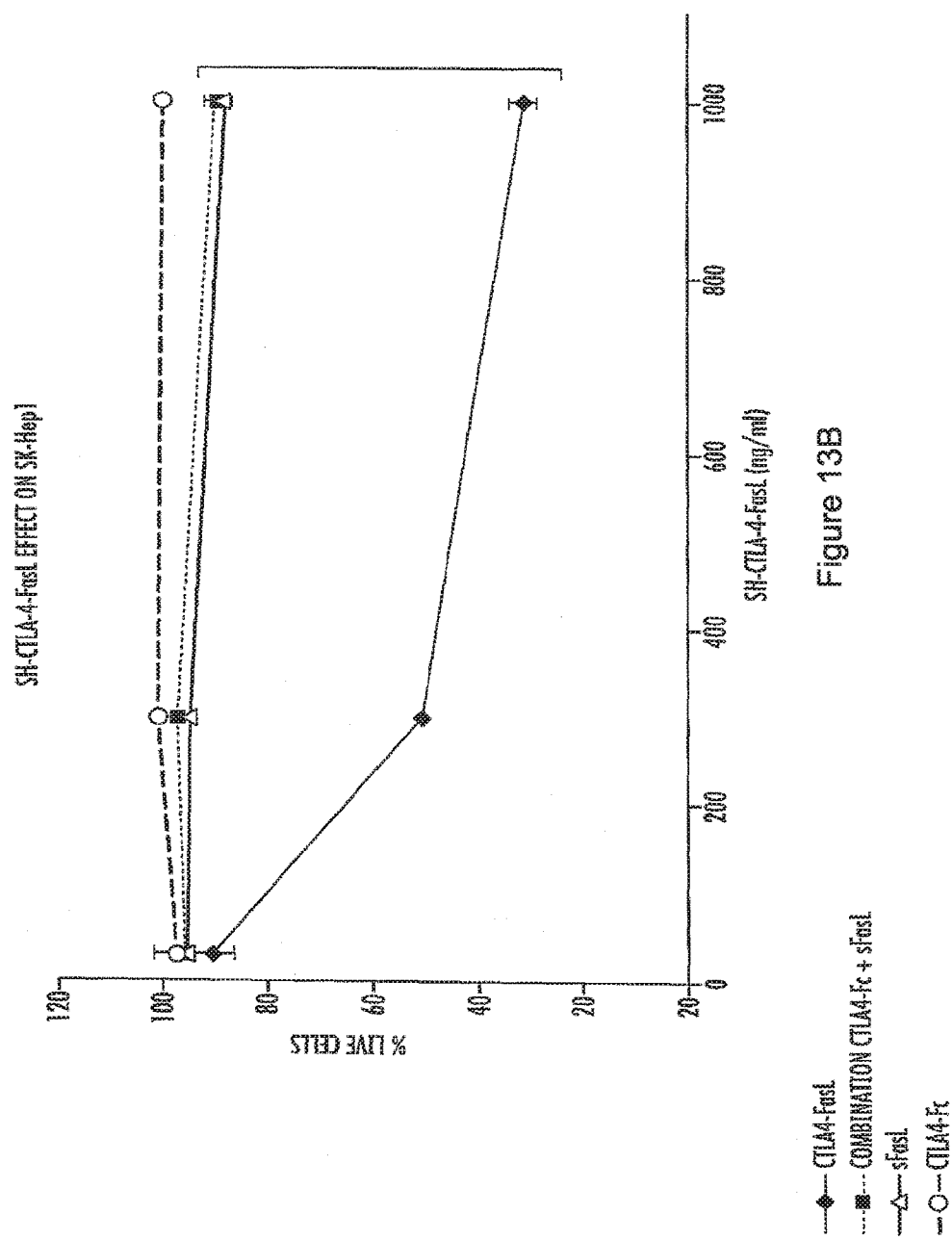

SCP chimeras have been shown to confer superior activity over their parts, separately or in combination. However, this was tested previously only in target cells that express binding molecules to both SCP sides. As the hepatocellular carcinoma (HCC) cell line SK-HEP1 does not express B7 molecules (FIG. 12), and therefore can bind to the FasL only, its activity was specifically tested. For that, SK-HEP1 cells were incubated in the presence or absence of soluble CTLA4 (CTLA4-Fc), soluble FasL (FLAG-FasL) or the combination of the latter two for 24 h, and cell viability was measured by MTS. As seen in FIG. 13B, the effect of the CTLA4-FasL fusion protein, and specifically its cytotoxic effect, is significantly more potent than that of the individual components, even when administered simultaneously. Thus, CTLA4-FasL is superior to the individual fusion protein components even in non-B7 expressing cells, suggesting its FasL domain is presented to the FasR in an exceptionally effective way (without wishing to be limited by a single hypothesis).

Figure 13C:
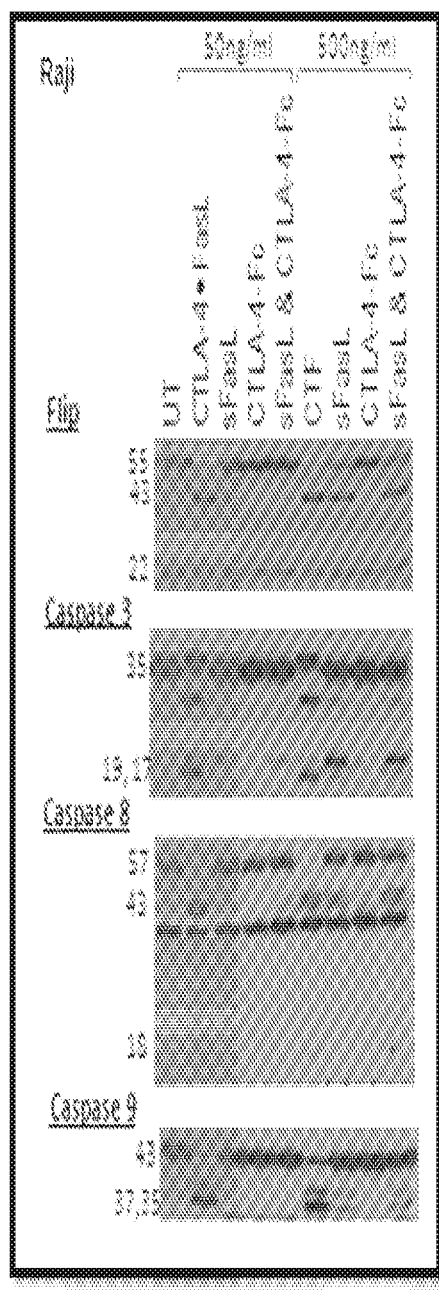
Figure 13D:
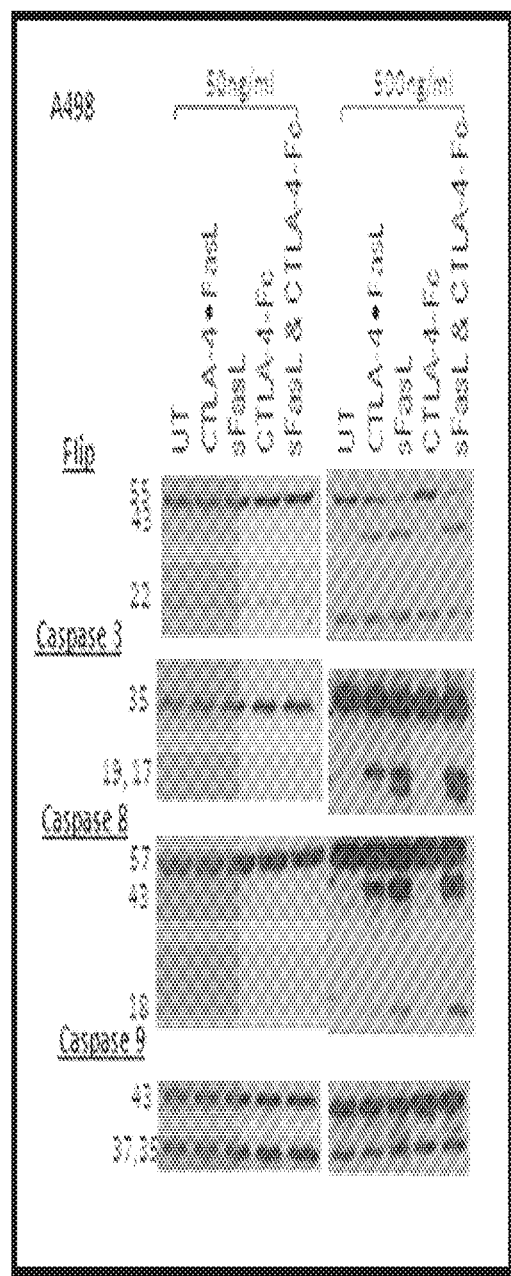
Figure 13E:
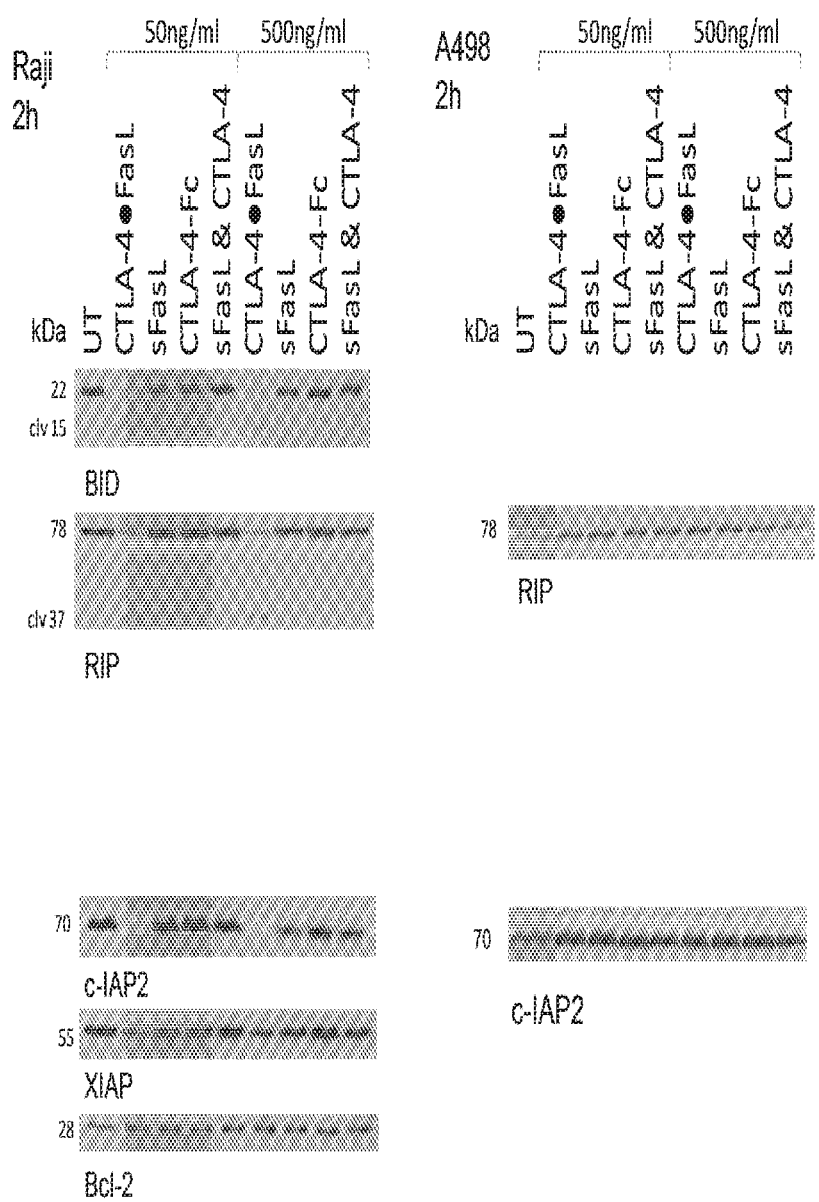

FIGS. 13C-13E are Western blots of whole cell lysates that show that CTLA4-FasL at low doses abrogates anti-apoptotic signals and activates the pro-apoptotic signals in B7 expressing cells (Raji cells (B-cell lymphoma)), but not in B7 negative cells A498 cells (renal cancer). At higher doses CTL4-FasL effectively activated pro-apoptotic signals in both cell lines.

FIGS. 13C-13E show that intracellular signaling induced by CTLA-4-FasL differs between the B7 positive B cell lymphoma cells and the B7 negative renal cell carcinoma cells.

Raji (B7+) and A498 (B7−) cells were incubated with 50 or 500 ng/ml CTLA-4•FasL, sFasL, CTLA-4-Fc or the combination of the last for 2 h. Cell lysates were subjected to immunoblotting with the following antibodies: caspase 3, caspase 8, caspase 9, FLIP and GAPDH. As could be seen from the activation of caspase 3, 8 and 9, in the A498 cell line, CTLA-4•FasL induces effective apoptosis only at high concentrations of 500 ng/ml (FIG. 13D), while in Raji cells this effect is reached already at 50 ng/ml and the distinction from sFasL is well seen in favor of CTLA-4•FasL (FIG. 13C). Flip is known as anti-apoptotic protein that interferes with caspase 8 activation. Its N-terminal form p43 indicates that the FLIP-L is cleaved and loses its anti-apoptotic activity. Interestingly, at a low dose of CTLA-4•FasL, 50 ng/ml, rapid abrogation of FLIP-L expression and increase in p43 expression was evident only in B7 positive cells. These observations suggest that CTLA-4•FasL induces activation of apoptotic signals and abrogates the anti-apoptotic ones at low concentrations only in B7 positive cells, while the B7 negative cells are resistant to the effect of the CTLA-4•FasL fusion protein at these concentrations. Of note, this difference was not observed when the cell lines were incubated in the presence of sFasL, CTLA4-Fc or the combination of the latter two.

FIG. 13E shows additional data after the above described doses of the various proteins were applied, followed by immunoblotting with antibodies against BID, RIP, c-IAP2, XIAP and Bcl-2 (for proteins from Raji cells, left hand side of the figure) or with antibodies against RIP and −IAP2 (for proteins from A498 cells, right hand side of the figure). For most of the proteins tested, CTLA-4•FasL fusion protein treatment significant reduces, or even eliminates, expression of the protein in question, in B7 expressing cells (Raji), and not in B7 negative cells (A498). Also, in the case of the proteins tested in FIG. 13E, the effect induced by CTLA4-FasL could not be seen when sFasL was tested, even at higher doses.

Figure 14A:
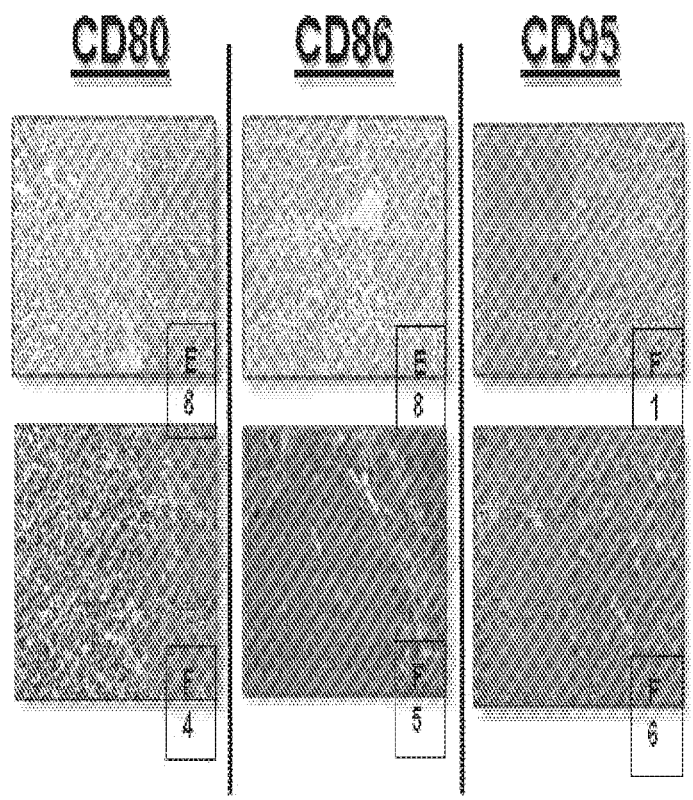
FIG. 14A shows immunohistochemistry analysis of B7 (CD80 and CD86) and Fas (CD96) receptor expression on lymphatic tissues; the top and bottom panels show results from two patients.
Figure 14B:
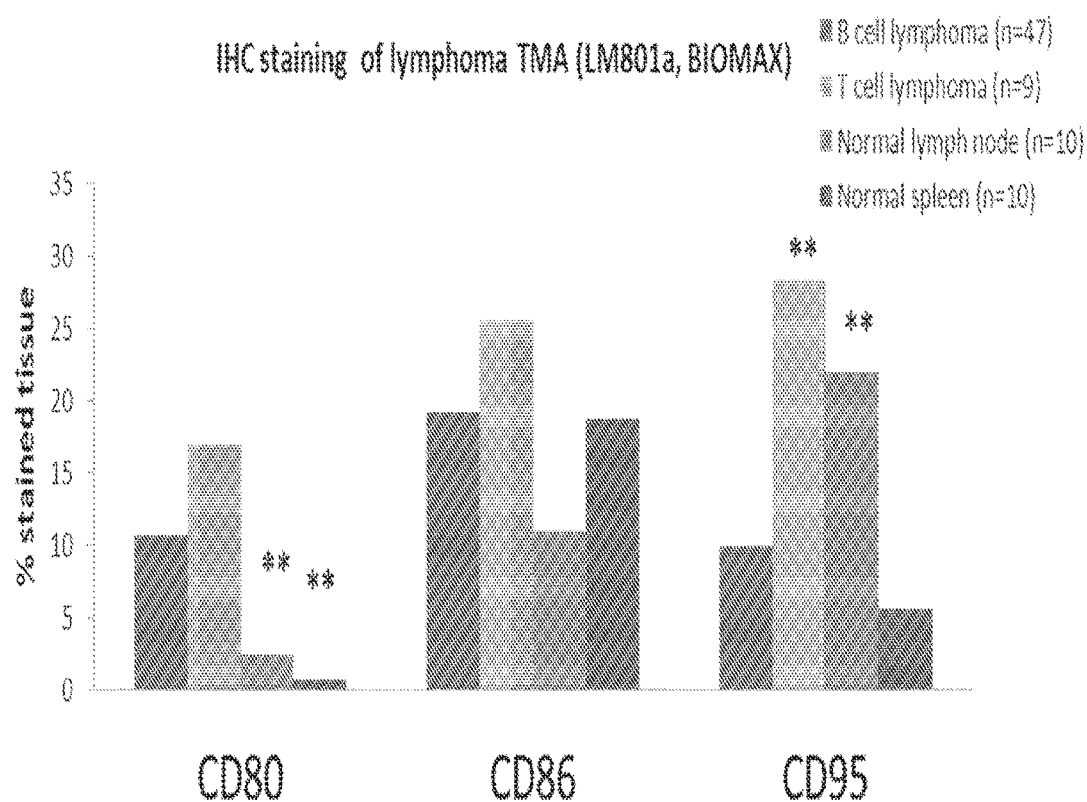
FIG. 14B shows quantification of a commercial tissue micro-array.

Immuno-histo-chemistry (IHC) was then used to analyze the expression of these receptors on tissue arrays of lymphoma and normal human tissues. It was found that the three receptors can be quantified by IHC on human tissues and that these receptors show high expression levels in a significant fraction of patients (FIG. 14). The identified correlation between the expression of these three receptors and drug activity could be used as powerful biomarker for drug activity and patient-treatment selection.

Figure 15:
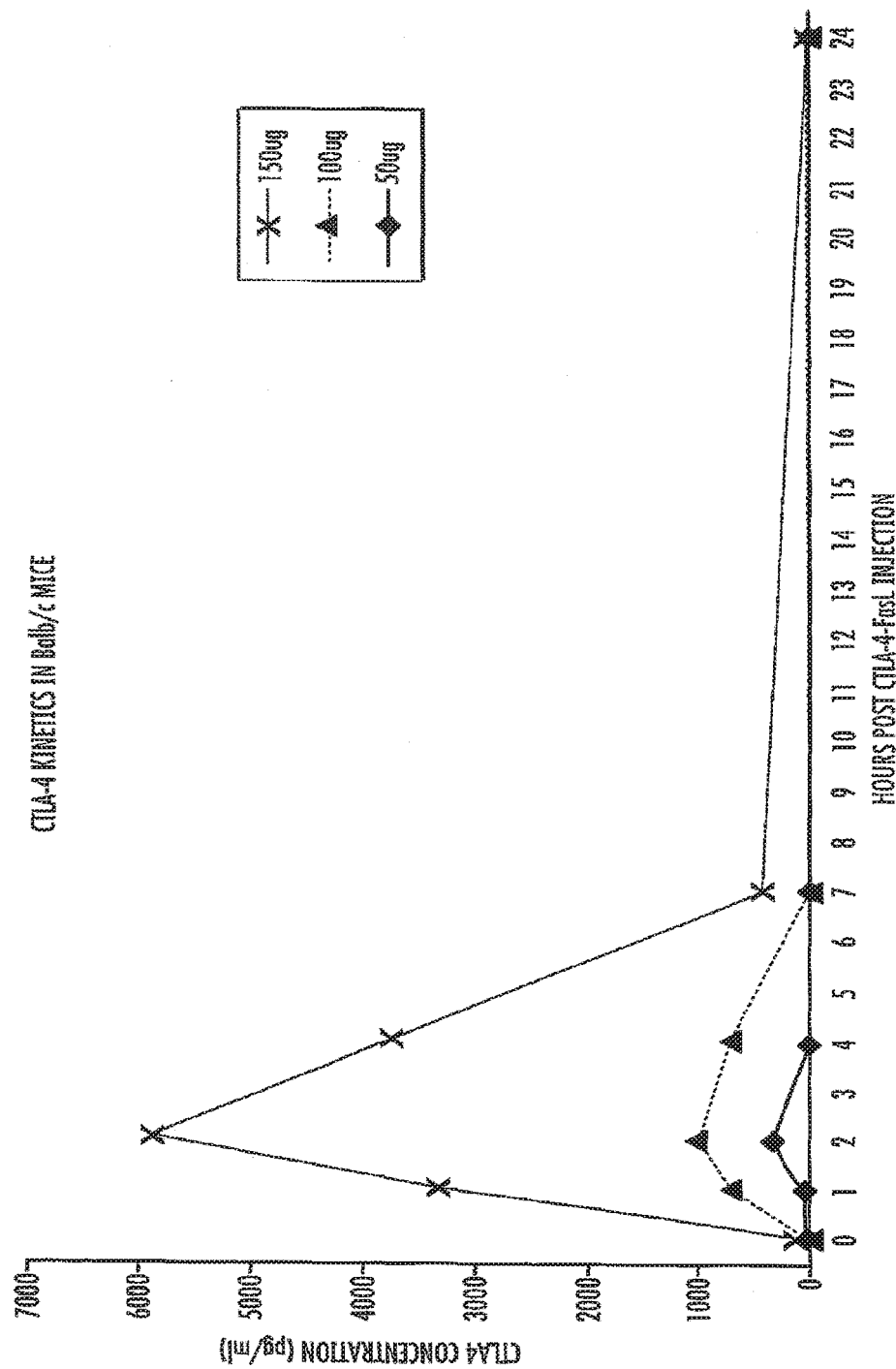
FIG. 15 shows the basic pharmacokinetic (PK) parameters of CTLA4-FasL in mice.

CTLA4-FasL Reduces Tumor Size in a Dose-Dependent Manner and Increases Survival in a B-Cell Lymphoma Xenograft Model Prior to initiation of studies in a mouse disease model, the basic pharmacokinetic (PK) parameters of CTLA4-FasL in mice were measured. The protein levels in the peripheral blood of Balb/c mice were quantified by a CTLA4 commercial ELISA at specific time points following subcutaneous injections. CTLA4-FasL levels were shown to reach the highest values approximately 2 hours post injection with T1/2 of approximately 4-5 hours post injection (FIG. 15). Similar results were obtained in both normal and NUDE mice (not shown).

The in-vivo activity of the purified CTLA4-FasL protein was assessed in two mouse cancer disease models; the first, human lymphoma in mouse model, measures the effect of CTLA4-FasL treatment on growth of a xenograft human lymphatic tumor within immune-compromised mice. In this model, mice were treated with twice-daily subcutaneous injections of CTLA4-FasL for several days. As illustrated in FIG. 16, treatment with both 50 ug and 20 ug daily dosages of CTLA4-FasL for 4 days, significantly inhibited the long-term growth of human JY xenograft tumors (16A), and significantly improved the survival of the treated mice (16B). Since the 20 ug/day dose was found to be as effective as the 50 ug dose, the effect of lower dosages was tested. In a second experiment five days administration of 10 ug/day was found to significantly inhibit tumor growth, with a significant effect lasting to ~20 days, while a low dose treatment of 4 ug/day for 4 consecutive days, which was repeated for 4 weeks, seems to keep tumor volumes at a stable reduced state (FIG. 17A). Survival analysis also revealed a positive effect of this treatment, although not to the same extent as seen with the 20 ug/day treatment. (FIG. 17B).

In agreement with tumor volume and the survival indexes, the high efficacy of CTLA4-FasL treatment of JY xenograft tumors was further illustrated by the histological analysis of JY tumors removed from the mice, showing clear atrophy of tumor tissue in mice treated with CTLA4-FasL injections. Immunostaining with anti-cleaved casapase 3 demonstrated that tumor cells in CTLA4-FasL treated mice undergo apoptosis (FIG. 18).

FIG. 19 shows the effect of CTLA4-FasL treatment on the survival of normal mice pre-injected with mouse BCL-1 mouse lymphatic cancer cells, showing that two doses per day of 5 ug or 2 ug of the CTL4-FasL fusion protein significantly increased mouse survival.

Results and Discussion—Dodecamer

As previously described, one of the forms of the CTLA4-FasL fusion protein is a dodecamer (12 monomers); both before and following purification, it is typically a very minor component of the total fusion protein (approximately 5%) but during purification it can become a major component of the fusion protein.

Without wishing to be limited by a single hypothesis, the hexamer may optionally be formed in two different ways, as a dimer of trimers or as a trimer of dimers. The "Dimer of Trimers" model assumes that FasL trimerization is stronger or forms quicker than CTLA4 dimerization. In this model the hexamer forms via dimerization of two FasL trimers. This type of hexamer is very stable since all CTLA4 domains are dimerized and all FasL domains are trimerized.

In the "Trimer of Dimers" model, it is assumed that CTLA4 dimerization is stronger or forms quicker than FasL trimerization. In this model the hexamer will form by trimerization of three CTLA4 dimers. This hexamer is only partially stable since, although all CTLA4 are dimerized, three of the FasL are not trimerized. This latter type of hexamer could break apart, forming free CTLA4 dimer subunits, which could then join a "Trimer of Dimers" hexamer to form a stable dodecamer. This dodecamer is predicted to be very stable since, as with the "Dimer of Trimers" hexamer model, here also all CTLA4 domains are dimerized and all FasL domains are trimerized.

FIG. 24 shows a model of the fusion protein in various combinations. Briefly, on the far left, a monomer is shown. In this context, the term "monomer" refers to a single fusion protein as described herein (in this non-limiting example, CTLA4-FasL fusion protein).

The next panel shows a dimer, which are two bonded fusion proteins. Next the trimer panel shows three bonded fusion proteins. The two different homo-hexamer structures are shown, followed by the dodecamer structure on the far right.

Unfortunately, as shown by the data below, the resultant dodecamer is quite toxic to mice. Injecting mice with very high dosages of the purified CTLA4-FasL preparation (10-20 times the therapeutic dose) was found to cause toxic effects, and investigation of these effects shown liver toxicity alongside a sharp increase in cytokine levels (data not shown). Since both SEC-HPLC and Native-PAGE analysis have shown that over 90% of the purified protein preparation is a homo-hexamer structure (250 kD), while the remaining 5-10% is a higher molecular weight (HMW) form, consisting with a homo-dodecamer structure (500 kD), experiments were performed to determine whether the efficacy and/or toxicity associated with this preparation is a result of the homo-hexamer or the dodecamer.

FIG. 20 shows the effect of the dodecamer as opposed to the hexamer on tumors in mice in-vivo. Briefly, 3 groups of Athymic-NUDE mice with subcutaneous JY xenograft tumors were treated twice a day, for 4 days, with 2.5ug of the purified CTLA4-FASL preparation (>90% homo-hexamer), 0.25 ug purified HMW fraction (representing 10% of the mixed preparation) and PBS as control. The HMW #11 fraction is the dodecamer, while the line marked "CTF-RT" is the purified (containing at least 90%) homo-hexamer preparation. The results indicate that the decrease in tumor size shown by the CTLA4-FasL preparation is a result of the homo-hexameric structure and not the 5-10% dodecamer contaminant.

To study toxicity, experiments were performed to determine the levels of ALT/AST enzymes, which are released to the serum as a result of liver dysfunction (FIG. 21, each number represents a single injected mouse), and immune involvement as characterized by cytokine levels in mice serum (FIG. 22, each number represents a single injected mouse).

Figure 22A:
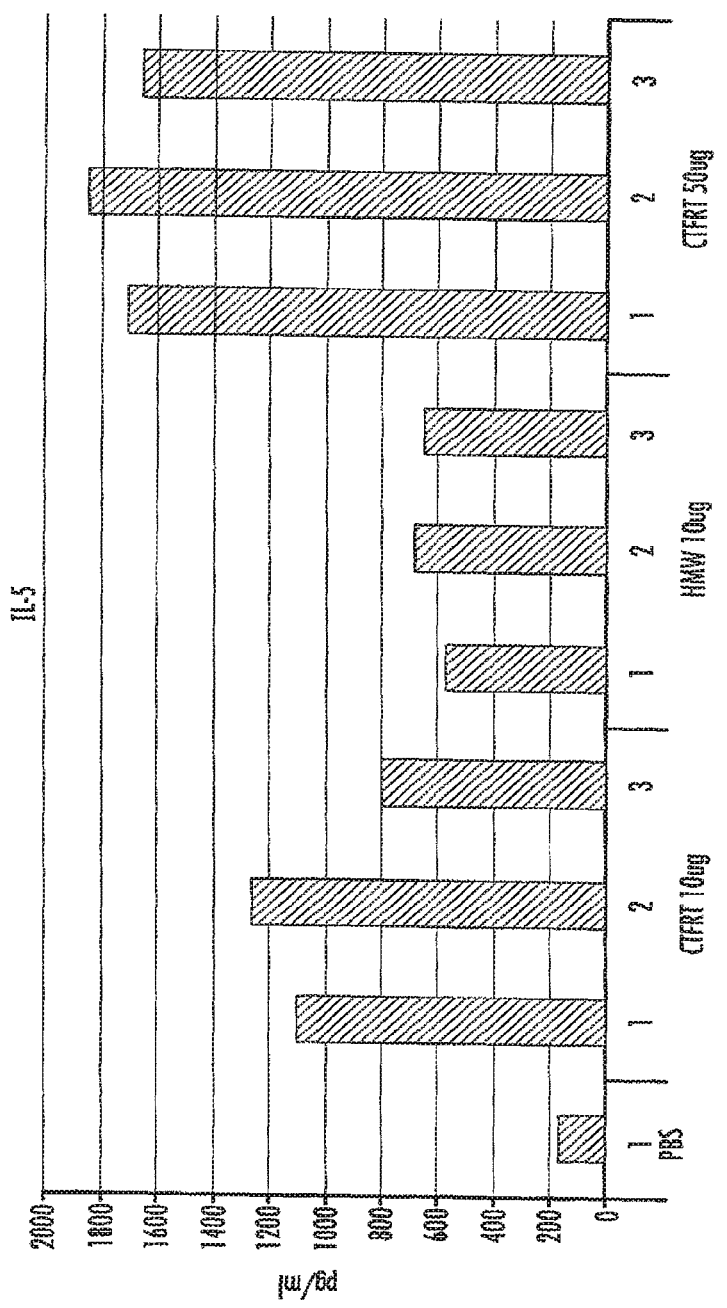
Figure 22B:
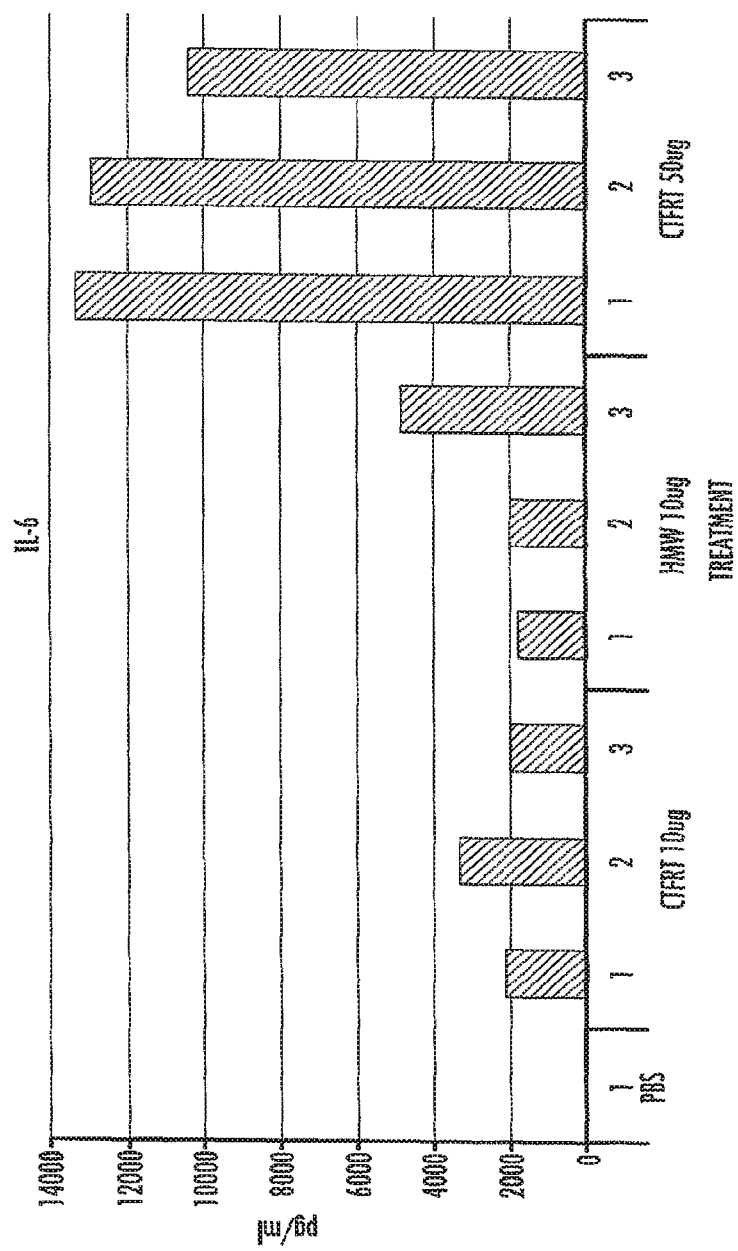
Figure 22C:
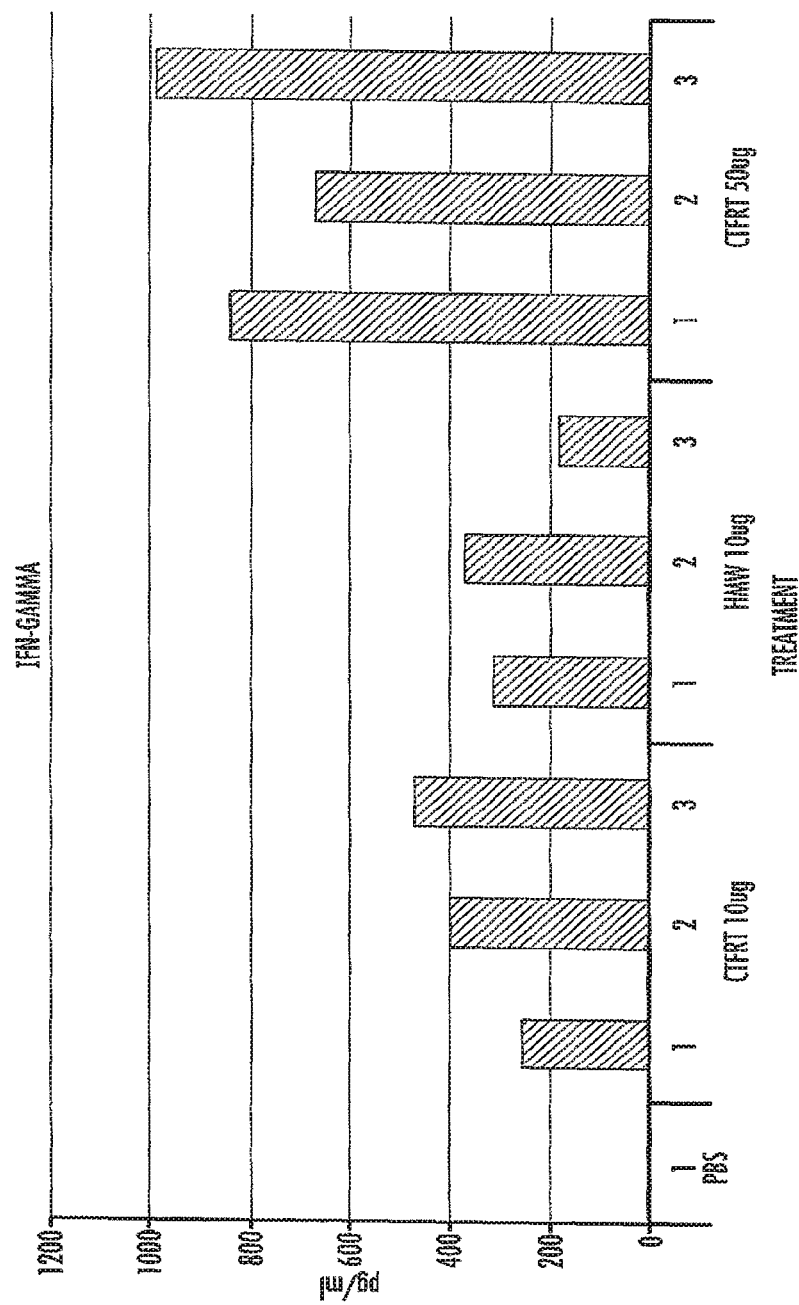
Figure 22D:
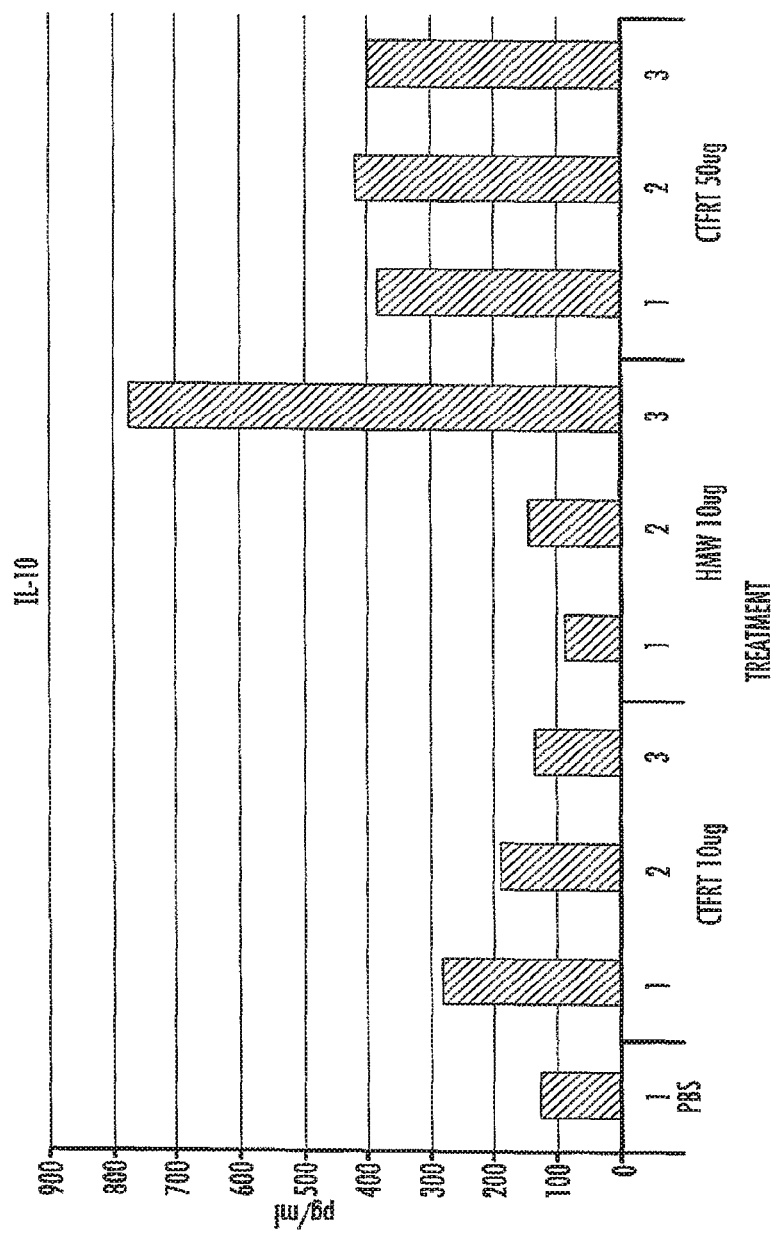
Figure 22E:
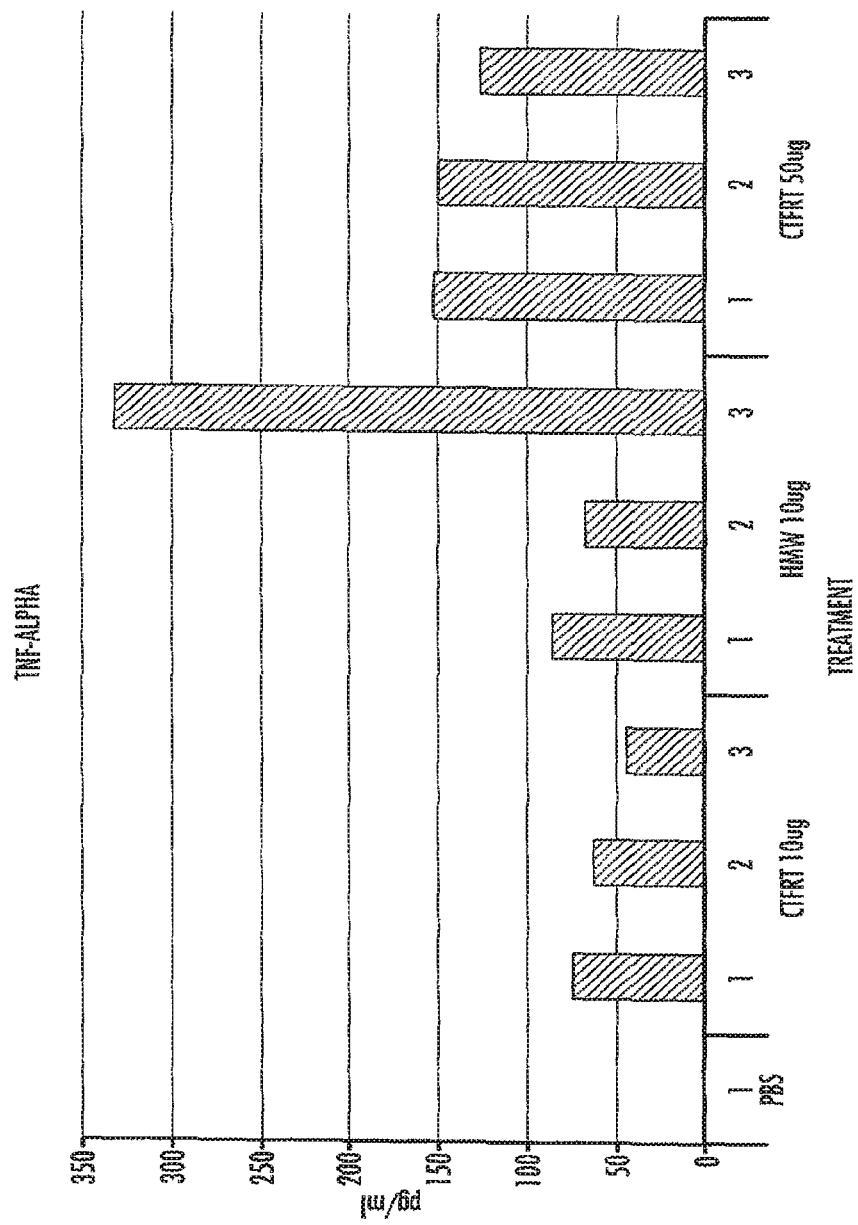

Mice were injected with 10 ug or 50 ug of the CTLA4-FASL preparation, 10 ug of the purified HMW (dodecamer) fraction and PBS as control. Blood was collected 5 hours post injection. Quantitative determinations of ALT/AST from serum were performed using Reflotron test strip (Roche). Detection of Cytokines in serum was measured by flow cytometry (FACS) using FlowCytomix Kit (eBioscience). The cytokines detected were as follows: IL-5 (FIG. 22A); IL-6 (FIG. 22B); IFN-gamma (FIG. 22C); IL-10 (FIG. 22D); and TNF-alpha (FIG. 22E).

As can be seen in FIG. 21, the HMW dodecamer fraction causes significantly higher liver toxicity as compared to the CTLA4-FASL preparation (>90% hexamer). Surprisingly, that was not the case with cytokine serum levels (shown in FIG. 22), which shows a similar rise following injection of both hexamer and dodecamer preparations.

Overall Discussion

In the present study the unique properties of the signal converter protein CTLA4-FasL as a potent apoptosis inducer of malignant cells were investigated. Without wishing to be limited by a closed list, at least some of the findings include the following: 1. CTLA4-FasL naturally forms a stable homo-hexamer; 2. CTLA4-FasL induces robust apoptosis of malignant cell lines while relatively sparing non-malignant ones; 3. The CTLA4-FasL killing effect is more efficient when both relevant receptors (e.g. B7 and FasR) are expressed on target cells; 4. Even in non-B7 expressing cells, CTLA4-FasL exhibited significantly higher apoptotic activity than its parts, alone or in combination; 5. CTLA4-FasL efficiently inhibited the growth of human B cell lineage tumors in a xenograft model.

Bi-specific and multi-specific biological drugs are believed to develop into the "next generation" of protein-based drugs. Mostly combining functional units of two known biological targets, this drug-development field is currently lead by bi-specific antibodies, while other bi-specific technologies, such as Signal Convertor Proteins, are being assessed as well. Without being limited by a closed list, among the many advantages of bi-specific biological drugs over existing biological drugs, that comprise only one target, is a significant synergistic effect which cannot be obtained by simply administering the functional activity units alone or in combination. These synergistic effects have been mainly suggested to stem from the ability of bi-functional molecules to influence two or more biological pathways concomitantly. Notably, the efficient apoptotic activity induced by CTLA4-FasL can be seen in human B cell lymphoma cells that express both a functional Fas receptor and B7 receptors, supporting the notion that more than one biological signaling pathway is involved. Indeed, in B7 expressing cells, CTLA4-FasL provoked activation of the cascade of caspases and abrogated anti-apoptotic signals at very low concentrations, a phenomenon that could not be mimicked by CTLA4-Fc, sFasL or their combination. Importantly, this also suggests that measuring the expression of FasR, CD80 and CD86 in patient tumor samples may be used as a biomarker for patient treatment selection.

Intriguingly, CTLA4-FasL potency was higher than that of FasL, CTLA4-Fc or the combination of the latter two when incubated with non-B7 expressing cells as well, making other explanations for its robust potency plausible. The above presented data suggests higher-order structures may play a significant role in the activity and potency of these novel bi-specific drugs, as for example the homo-hexamer structures described herein.

As reported for other TNF-super family members, activation of the Fas apoptosis pathway requires trimerization of Fas receptors upon binding of FasL trimers. Moreover, it was previously shown that efficient Fas activation requires two adjacent such trimerization events. Therefore, the finding that the natural stochiometry of soluble CTLA4-FasL is a homo-hexamer is of great significance for understanding its unique, robust apoptotic capabilities. Being a hexamer, CTLA4-FasL is capable of presenting two functional trimers of FasL to their relevant receptors, resulting in optimal initiation of the apoptosis signaling pathway to the malignant cells.

Figure 10:
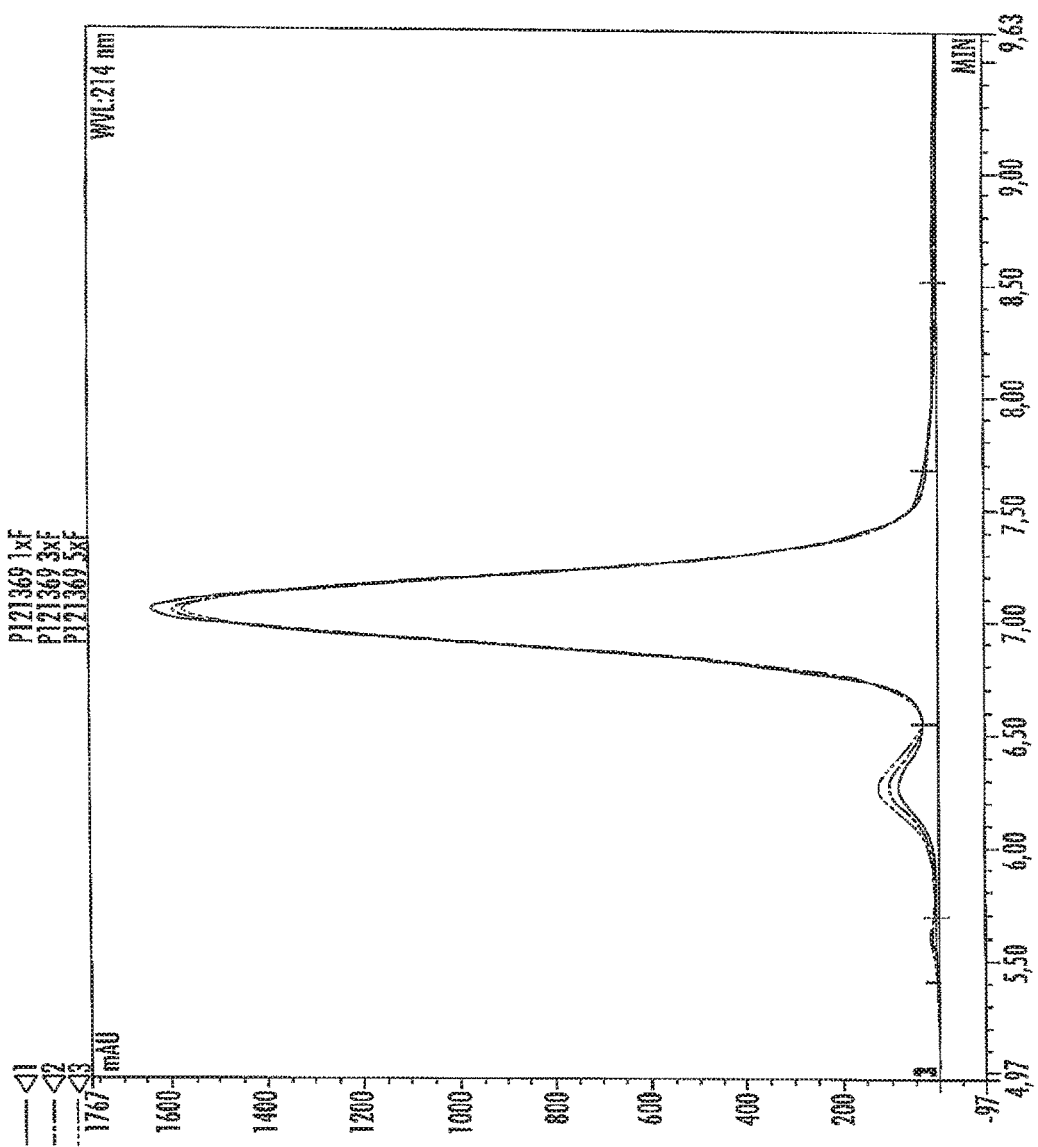
Figure 11A:
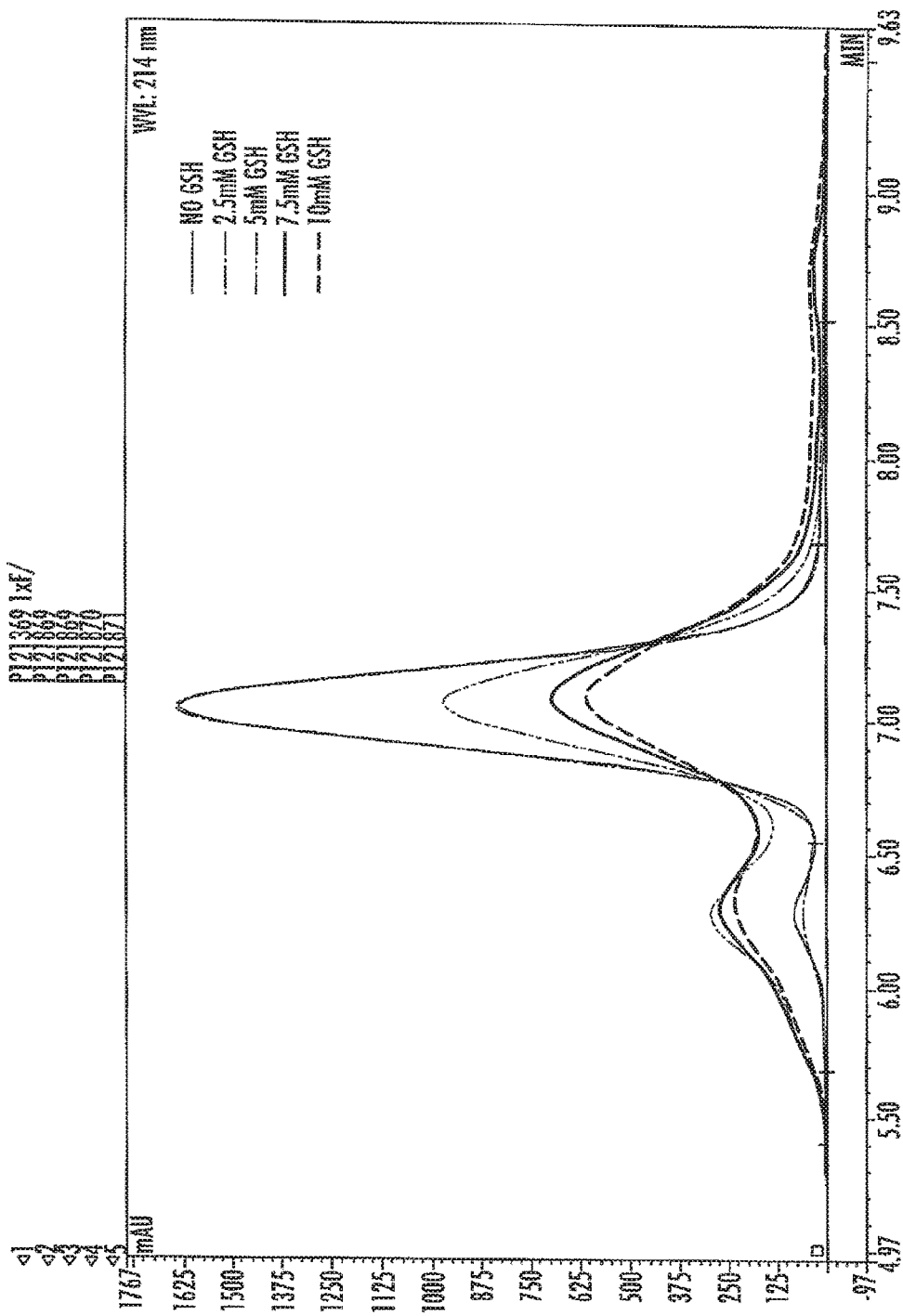
Figure 11B:
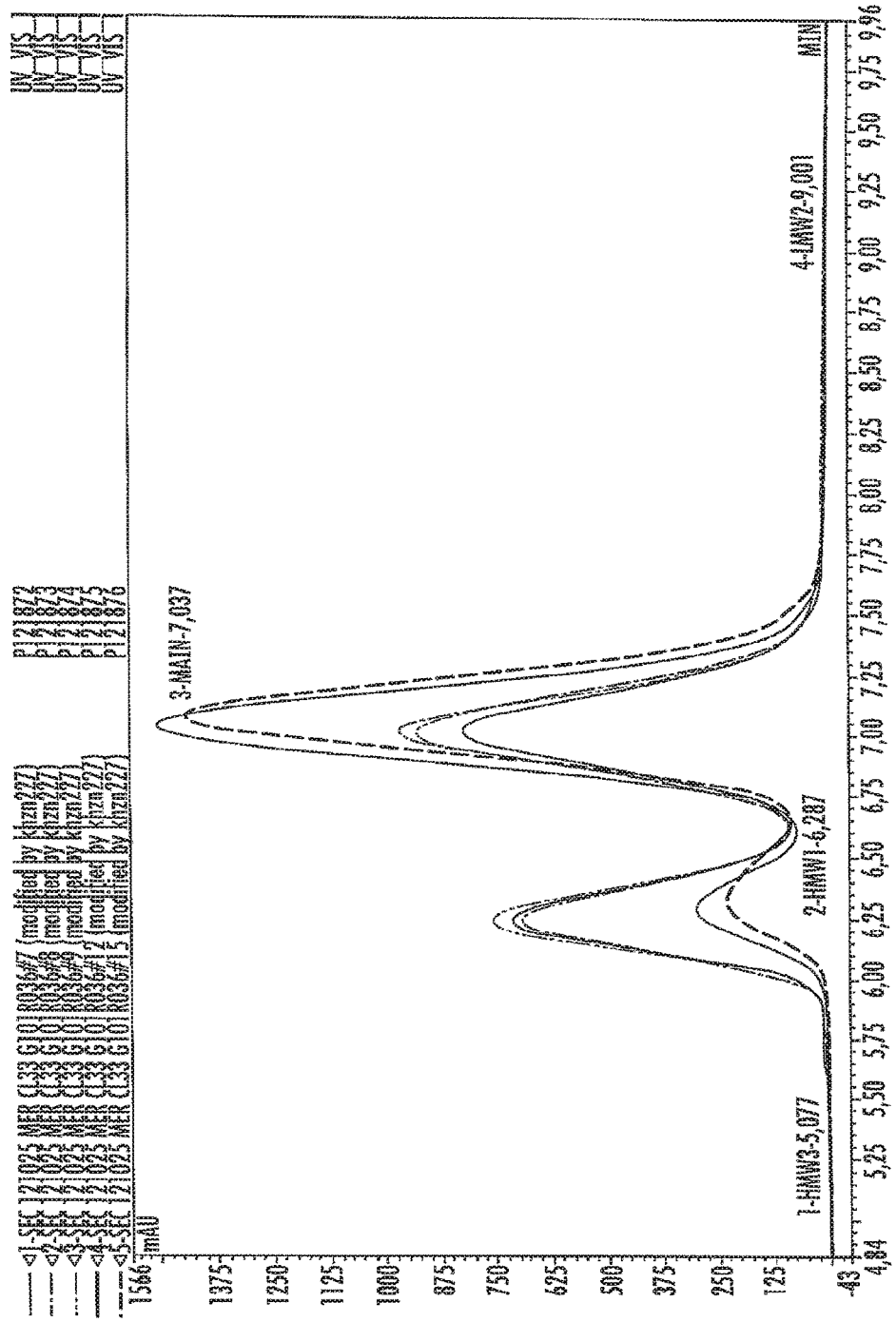

The formation of a membrane bound CTLA4-FasL homo-hexamer was suggested previously. Since only homo-trimers were identified at that earlier study, the authors suggested that two CTLA4-FasL trimers may form a homo-hexamer on target cell's surface when anchored to B7 molecules, thereby inducing an extremely efficient apoptotic effect that would explain the high efficacy of CTLA4-FasL observed in that report. Here data is presented suggesting that CTLA4-FasL naturally form a soluble and stable homo-hexamer as early as it is produced and that this structure maintains its stability through a purification process that includes harsh conditions and multiple freeze/thaw cycles (FIG. 10, previously described). The hexameric structure can be explained by the fact that CTLA4 naturally forms a disulfide-linked dimer, while FasL naturally forms a stable trimer, thus, as suggested in FIG. 24, a CTLA4-FasL trimer would possess an "open cysteine" that could link one such trimer to a second trimer, forming a stable CTLA4-FasL homo-hexamer.

As described above, one possibility of dodecamer formation may optionally occur through a less stable "trimer of dimers" hexamer. Such a dodecamer has been shown to cause liver toxicity in mice. Therefore according to at least some embodiments, preferably the CTLA4-FasL fusion protein has less than 10% dodecamer, less than 7.5% dodecamer, less than 5% dodecamer, less than 2.5% dodecamer or less than 1% dodecamer.

Using a xenograft human-mouse disease model it was shown that CTLA4-FasL has the ability to inhibit the growth of tumors originating from B lymphocytes lineage, and to provide a significant beneficial effect on mice survival, in a dose dependent manner and at very low dosages. It was shown that this in-vivo effect is mediated by activation of the caspases cascade, as can be seen by the increased cleaved caspase 3 in immunohistochemistry of the tumors.

In summary, data is presented that the fusion protein, CTLA4-FasL induces effective apoptosis of B lymphoblastoid cells, in-vitro and in-vivo, in a highly efficient way. Also, in the case of B7 expressing cells, its potency stems from the combination of its synergistic effect of activating the cascade of caspases while abrogating the anti-apoptotic signaling, with its unique natural hexameric structure. Without wishing to be limited by a single hypothesis, it appears that that this combination of properties makes CTLA4-FasL an extremely potent apoptosis inducer of at least B7 expressing tumors, such as B cell lymphomas.

While the invention has been described with respect to a limited number of embodiments, it will be appreciated that many variations, modifications and other applications of the invention may be made, and that various combinations and subcombinations of embodiments are also possible and encompassed within the scope of this application.

What is claimed is:

1. A CTLA4-Fasl fusion protein preparation, wherein the fusion protein is purified such that at least 90% is in the form of a homo-hexamer of approximately 250 kD in molecular weight.

2. The CTLA4-Fasl fusion protein preparation of claim 1, wherein the fusion protein is purified such that at least 95% is in the form of the homo-hexamer of approximately 250 kD in molecular weight.

3. The CTLA4-Fasl fusion protein preparation of claim 1, comprising no more than 5% of CTLA4-Fasl fusion protein as a multi-mer of approximately 500 kD in molecular weight.

4. The CTLA4-Fasl fusion protein preparation of claim 3, comprising no more than 5% of CTLA4-Fasl fusion protein in the form of a dodecamer.

5. A pharmaceutical composition comprising the CTLA4-Fasl fusion protein preparation of claim 1 and a pharmaceutically acceptable carrier.

6. The CTLA4-Fasl fusion protein preparation of claim 1, being soluble.

7. The CTLA4-Fasl fusion protein preparation of claim 1, being purified from host-cell proteins.

8. The CTLA4-Fasl fusion protein preparation of claim 1, wherein said fusion protein is purified from CHO cells.

9. The stable soluble CTLA4-FasL fusion protein preparation of claim 1, wherein said homo-hexamer is approximately 250 kD in molecular weight as detected by Native-PAGE or Size-Exclusion High-performance Liquid Chromatography (SE-HPLC).

10. The CTLA4-Fasl fusion protein preparation of claim 1, being obtainable by a method comprising separating a cell media from cells expressing said CTLA4-Fasl fusion protein, and applying the cell media to a Concavalin-A (Con A) column followed by Size-Exclusion-Chromatography (SEC) column.

* * * * *

SEQUENCE LISTING

<160> NUMBER OF SEQ ID NOS: 2

<210> SEQ ID NO 1
<211> LENGTH: 281
<212> TYPE: PRT
<213> ORGANISM: artificial
<220> FEATURE:
<223> OTHER INFORMATION: Synthetic fusion protein construct

<400> SEQUENCE: 1

```
Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
            35                  40                  45

Cys Ala Ala Thr Tyr Met Met Gly Asn Glu Leu Thr Phe Leu Asp Asp
50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Gly Ser Leu Glu
            115                 120                 125

Lys Gln Ile Gly His Pro Ser Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280

<210> SEQ ID NO 2
<211> LENGTH: 301
<212> TYPE: PRT
<213> ORGANISM: artificial
<220> FEATURE:
<223> OTHER INFORMATION: synthetic fusion protein construct with signal
      peptide

<400> SEQUENCE: 2

Met Arg Ala Leu Leu Ala Arg Leu Leu Leu Cys Val Leu Val Val Ser
1               5                   10                  15

Asp Ser Lys Gly Ala Met His Val Ala Gln Pro Ala Val Val Leu Ala
            20                  25                  30

Ser Ser Arg Gly Ile Ala Ser Phe Val Cys Glu Tyr Ala Ser Pro Gly
            35                  40                  45

Lys Ala Thr Glu Val Arg Val Thr Val Leu Arg Gln Ala Asp Ser Gln
50                  55                  60

Val Thr Glu Val Cys Ala Ala Thr Tyr Met Met Gly Asn Glu Leu Thr
```

-continued

```
65                  70                  75                  80

Phe Leu Asp Asp Ser Ile Cys Thr Gly Thr Ser Ser Gly Asn Gln Val
                85                  90                  95

Asn Leu Thr Ile Gln Gly Leu Arg Ala Met Asp Thr Gly Leu Tyr Ile
            100                 105                 110

Cys Lys Val Glu Leu Met Tyr Pro Pro Pro Tyr Tyr Leu Gly Ile Gly
        115                 120                 125

Asn Gly Thr Gln Ile Tyr Val Ile Asp Pro Glu Pro Cys Pro Asp Ser
    130                 135                 140

Gly Ser Leu Glu Lys Gln Ile Gly His Pro Ser Pro Pro Pro Glu Lys
145                 150                 155                 160

Lys Glu Leu Arg Lys Val Ala His Leu Thr Gly Lys Ser Asn Ser Arg
                165                 170                 175

Ser Met Pro Leu Glu Trp Glu Asp Thr Tyr Gly Ile Val Leu Leu Ser
            180                 185                 190

Gly Val Lys Tyr Lys Lys Gly Gly Leu Val Ile Asn Glu Thr Gly Leu
        195                 200                 205

Tyr Phe Val Tyr Ser Lys Val Tyr Phe Arg Gly Gln Ser Cys Asn Asn
    210                 215                 220

Leu Pro Leu Ser His Lys Val Tyr Met Arg Asn Ser Lys Tyr Pro Gln
225                 230                 235                 240

Asp Leu Val Met Met Glu Gly Lys Met Met Ser Tyr Cys Thr Thr Gly
                245                 250                 255

Gln Met Trp Ala Arg Ser Ser Tyr Leu Gly Ala Val Phe Asn Leu Thr
            260                 265                 270

Ser Ala Asp His Leu Tyr Val Asn Val Ser Glu Leu Ser Leu Val Asn
        275                 280                 285

Phe Glu Glu Ser Gln Thr Phe Phe Gly Leu Tyr Lys Leu
    290                 295                 300
```